US010233431B2

(12) United States Patent
Yuzawa et al.

(10) Patent No.: US 10,233,431 B2
(45) Date of Patent: Mar. 19, 2019

(54) PRODUCING 3-HYDROXYCARBOXYLIC ACID AND KETONE USING POLYKETIDE SYNTHASES

(71) Applicant: The Regents of the University of California, Oakland, CA (US)

(72) Inventors: Satoshi Yuzawa, El Cerrito, CA (US); Leonard Katz, Oakland, CA (US); Jay D. Keasling, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 14/633,076

(22) Filed: Feb. 26, 2015

(65) Prior Publication Data

US 2015/0307855 A1 Oct. 29, 2015

Related U.S. Application Data

(60) Provisional application No. 61/945,060, filed on Feb. 26, 2014.

(51) Int. Cl.

| | |
|---|---|
| ***C12P 7/26*** | (2006.01) |
| ***C12P 7/42*** | (2006.01) |
| ***C12N 9/10*** | (2006.01) |
| ***C12N 9/02*** | (2006.01) |
| ***C12N 9/16*** | (2006.01) |
| ***C12N 15/54*** | (2006.01) |
| ***C12N 15/53*** | (2006.01) |
| ***C12N 15/55*** | (2006.01) |
| ***C12N 15/31*** | (2006.01) |
| ***C07K 14/39*** | (2006.01) |
| ***C07K 19/00*** | (2006.01) |
| ***C12N 9/04*** | (2006.01) |
| ***C07K 14/36*** | (2006.01) |

(52) U.S. Cl.

CPC ............ *C12N 9/1029* (2013.01); *C07K 14/36* (2013.01); *C12N 9/0006* (2013.01); *C12N 9/16* (2013.01); *C12P 7/26* (2013.01); *C12P 7/42* (2013.01); *C12Y 203/01* (2013.01); *C07K 2319/00* (2013.01); *C12Y 101/01001* (2013.01); *C12Y 203/01041* (2013.01); *C12Y 301/02001* (2013.01)

(58) Field of Classification Search

None

See application file for complete search history.

(56) References Cited

U.S. PATENT DOCUMENTS

2003/0170725 A1* 9/2003 Khosla ................ C07D 309/36 435/7.1

OTHER PUBLICATIONS

Bohm et al., Engineering of a minimal modular polyketide synthase, and targeted alteration of stereospecificity of polyketide chain extension, Chem. Biol., 1998, 5, 407-412.*

Bihlmaier et al., Biosynthetic gene cluster for the polyenoyltetramic acid alpha-Lipomycin, Antimicrobial Agents Chemotherapy, 2006, 50, 2113-21.*

Zhu et al., Biosynthesis and genetic engineering of polyketides, Acta Botanica Yunnanica, 2008, 30, 249-78.*

Reeves et al., Alteration of the Substrate Specificity of a Modular Polyketide Synthase Acyltransferase Domain through Site-Specific Mutations, Biochemistry, 2001, 40, 15464-70.*

Hans et al, "Mechanistic analysis of Acyl Transferase Domain Exchange in Polyketide Synthase Modules", JACS., 2003, 125, 5366-5374.

Hutchinson, C Richard, "Combinatorial biosynthesis for new drug discovery", Curr.Opin. Microbio., 1998, 319-329.

Jacobsen et al., Spontaneous priming of a downstream module in 6-Deoxyerythronolide B syntase leads to Polyketide biosynthesis, Biochemistry, 1998, No. 37, 4928-4934.

Kao et al, "Gain of function mutagenesis of the erythromycin polyketide synthase. 2. Engineered biosynthesis of an Eight-Member ring tetraketide lactone", J. Am. Chem. Soc, 1997, 119, 11339-11340.

Liou et al., "Quantitative analysis of loading and extender Acyltransferases of modular polyketide synthases", Biochemistry, 2003, V 42, 200-207.

McDaniel et al., "Gain-of-Function Mutagenesis of a Modular Polyketide Synthase", J. Am. Chem. Soc., 1997, 119, 4309-4310.

Murli et al., "Metabolic engineering of *Escherichia coli* for improved 6-deoxyerythronolide B production", J. Ind. Microbiol Biotechnol., 2003, 30, 500-509.

Peiper et al, "Erythromycin Biosynthesis: Kinetic Studies on a Fully Active Modular Polyketide Synthase Using natural and Unnatural Substrates", Biochemistry, 1996, 35, 2054-2060.

Van Draanen et al, "Protocols for Preparation of Each of the Four Possible Steroisomeric a-Alkyl-b-hydroxy Carboxylic Acids from a Single Chiral Aldol Reagent", J. Org. Chem. 1991, 56, 2499-2506.

Weissman et al, "Origin of Starter Units for Erythromycin Biosynthesis", Biochemistry, 1998, 37, 11012-11017.

Weissman et al, "Identification of a Phosphopantetheinyl Transferase for Erythromycin Biosynthesis in Saccharopolyspora erythraea", ChemBioChem, 2005, 5, 116-125.

Yuzawa et al., "Construction of a Part of a 3-Hyrdoxypropionate Cycle for Heterologous Polyketide Biosynthesis in *Escherichia coli*" Biochemistry, 2012, 51, 9779-9781.

Yuzawa et al., "Broad Substrate Specificity of the Loading Didomain of the Lipomycin Polyketide Synthase", Biochemistry, 2013, 52, 3791-3793.

* cited by examiner

*Primary Examiner* — Robert B Mondesi
*Assistant Examiner* — Todd M Epstein
(74) *Attorney, Agent, or Firm* — Robin C. Chiang; Lawrence Berkeley National Laboratory

(57) ABSTRACT

The present invention provides for a polyketide synthase (PKS) capable of synthesizing a 3-hydroxycarboxylic acid or ketone. The present invention also provides for a host cell comprising the PKS and when cultured produces the 3-hydroxycarboxylic acid or ketone.

12 Claims, 18 Drawing Sheets

Specification includes a Sequence Listing.

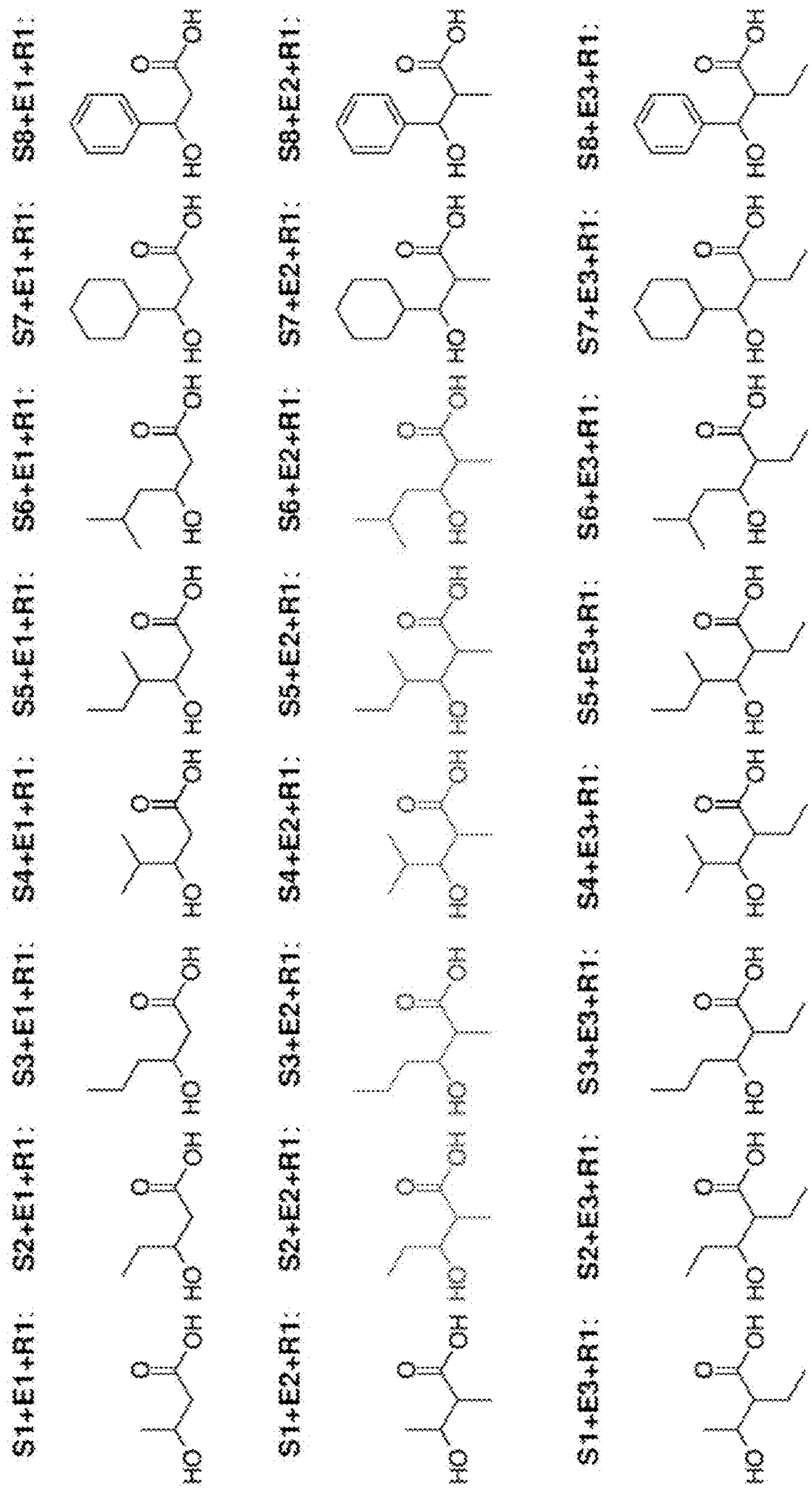
Figure 1-A

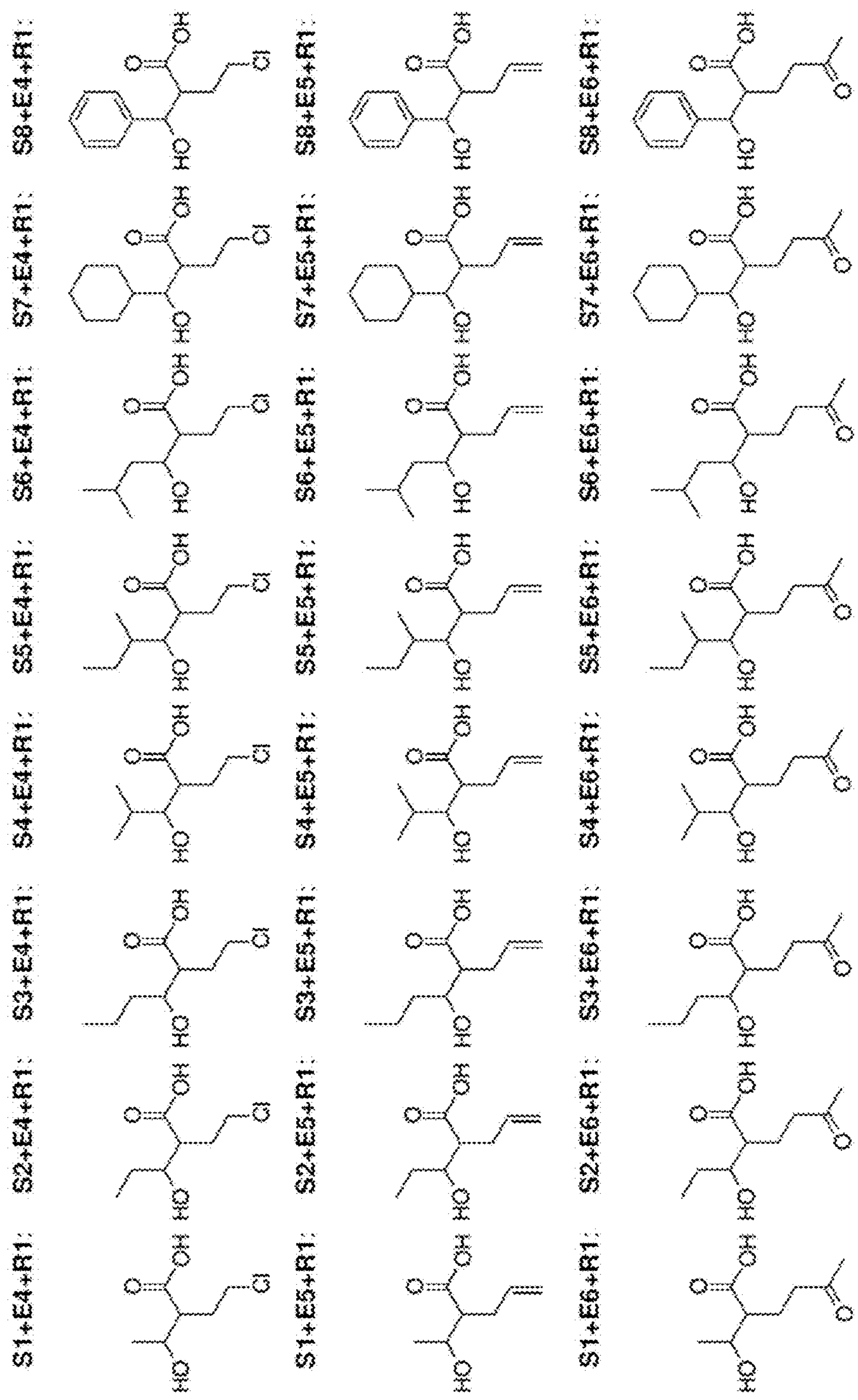
Figure 1-B

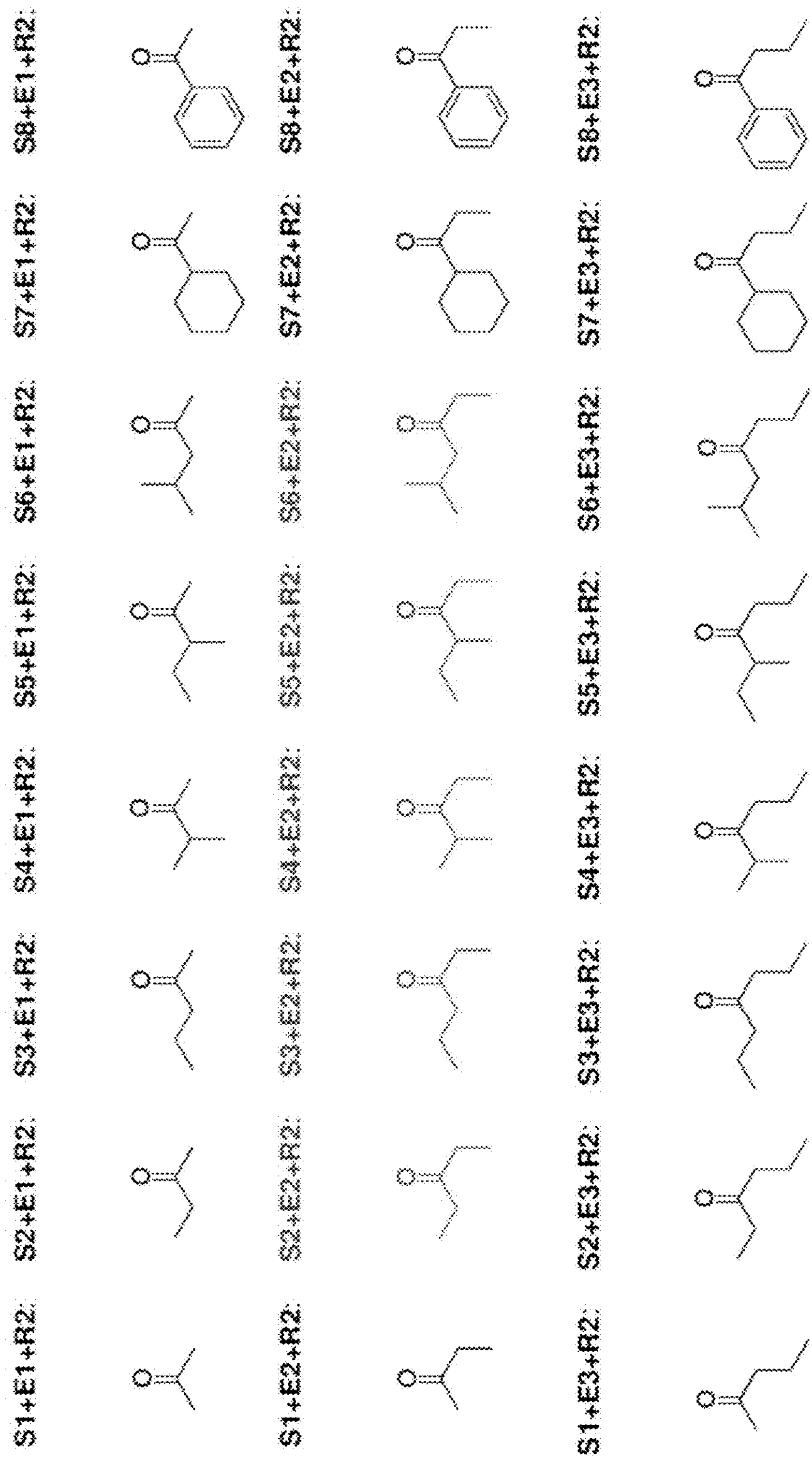
Figure 2-A

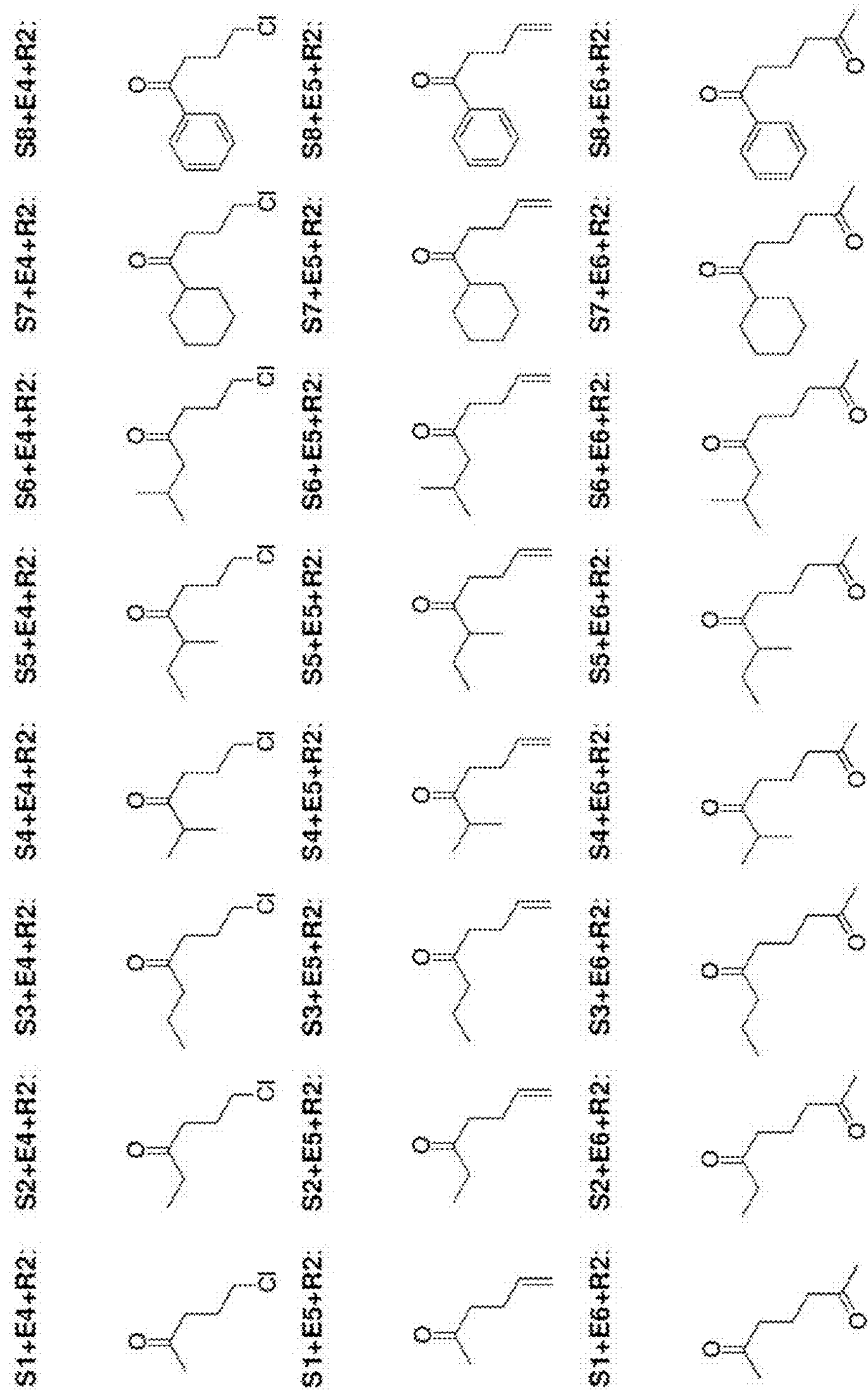
Figure 2-B

AmpKR1 SSTAGMWGSGVHAAYVAGN (SEQ ID NO:1)
NysKR1 SSTAGMWGSGVHAAYVAGN (SEQ ID NO:2)
AmpKR11 SSTAGMWGSGAHAAYVAGN (SEQ ID NO:3)
LipKR1 SSIAGVWGSGDHGAYAAAN (SEQ ID NO:4)

(A)
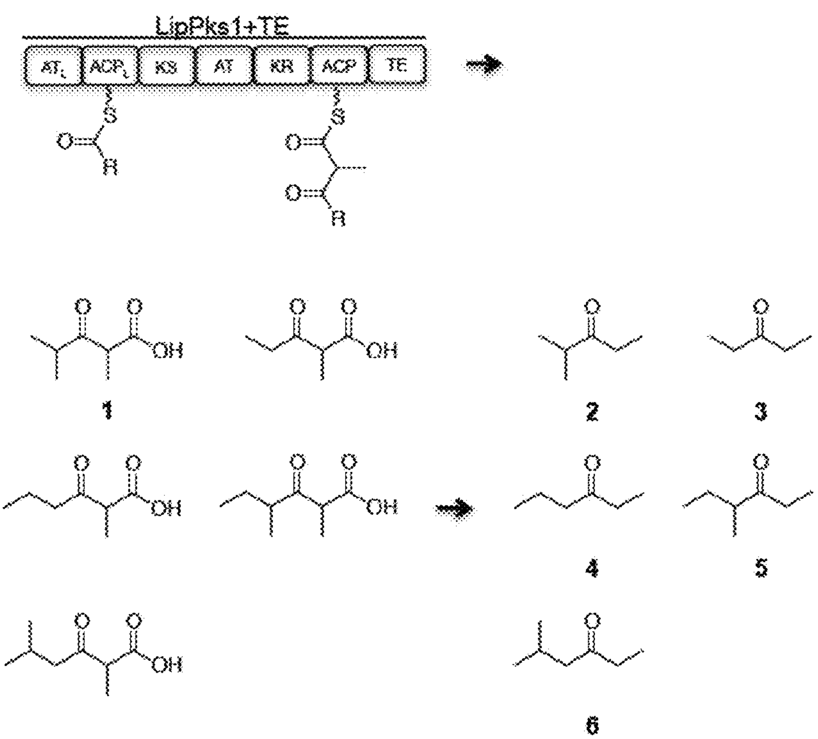
(B)
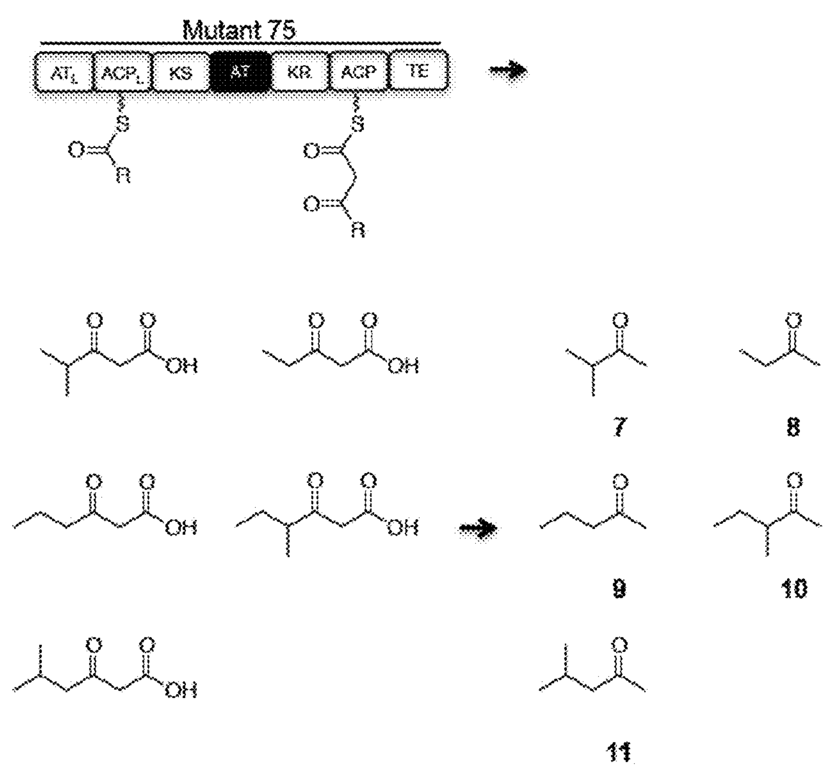
Figure 15

PRODUCING 3-HYDROXYCARBOXYLIC ACID AND KETONE USING POLYKETIDE SYNTHASES

CROSS-REFERENCE TO RELATED APPLICATIONS

This application claims priority to U.S. Provisional Patent Application Ser. No. 61/945,060, filed on Feb. 26, 2014, which is hereby incorporated by reference.

STATEMENT OF GOVERNMENTAL SUPPORT

This invention was made with government support under Contract No. DE-ACO2-05CH11231 awarded by the United States Department of Energy. The government has certain rights in the invention.

FIELD OF THE INVENTION

This invention relates generally to 3-hydroxycarboxylic acid and ketone production using polyketide synthases.

BACKGROUND OF THE INVENTION

Type I polyketide synthases (PKSs) are programmable, multifunctional enzymes capable of possessing all of the catalytic capacity of fatty-acid synthases (FASs). However, unlike the FAS enzyme, which iteratively extends and fully reduces the β-carbonyl generated with each extension of the hydrocarbon backbone, PKS systems utilize a discreet set of enzymatic domains for each extension and reduction of the nascent chain. These sets, commonly referred to as modules, can incorporate a variety of extenders until resulting in different side chains. They also can encode between zero and three of the reducing domains associated with FASs leading to a ketone, hydroxy, double bond, or fully saturated carbon at the beta position of the growing polyketide chain (Hopwood, D. A. and D. H. Sherman. 1990. Molecular genetics of polyketides and its comparison to fatty acid biosynthesis. Annual Review of Genetics 24:37-66).

Due to their modularity, PKS systems have been extensively explored for production of "unnatural" natural products (Weissman, K. J. and P. F. Leadlay. 2005. Combinatorial biosynthesis of reduced polyketides. Nature Reviews Microbiology 3:925-936). Hundreds of these molecules have been produced, ranging from basic lactones to modified versions of well established drugs.

SUMMARY OF THE INVENTION

The present invention provides for a polyketide synthase (PKS) capable of synthesizing a 3-hydroxycarboxylic acid or ketone. The PKS is not a naturally occurring PKS. In some embodiments of the invention, the 3-hydroxycarboxylic acid or ketone is not a compound synthesized by a naturally occurring PKS. In some embodiments of the invention, the PKS is a hybrid PKS comprising modules, modules, and/or portions thereof, or functional variants thereof, from two or more naturally occurring PKSs.

The present invention provides for a recombinant nucleic acid that encodes a polyketide synthase (PKS) of the present invention. The recombinant nucleic acid can be replicon capable of stable maintenance in a host cell. In some embodiments, the replicon is stably integrated into a chromosome of the host cell. In some embodiments, the replicon is a plasmid. The present invention also provides for a vector or expression vector comprising a recombinant nucleic acid of the present invention. The present invention provides for a host cell comprising any of the recombinant nucleic acid and/or PKS of the present invention. In some embodiments, the host cell, when cultured under a suitable condition, is capable of producing the 3-hydroxycarboxylic acid or ketone.

The present invention provides for a host cell comprising any of the recombinant nucleic acid and/or PKS of the present invention. In some embodiments, the host cell, when cultured, is capable of producing a 3-hydroxycarboxylic acid or ketone.

The present invention provides a method of producing a 3-hydroxycarboxylic acid or ketone, comprising: providing a host cell of the present invention, and culturing said host cell in a suitable culture medium such that the 3-hydroxycarboxylic acid or ketone is produced.

The present invention provides for a composition comprising a 3-hydroxycarboxylic acid or ketone isolated from a host cell from which the 3-hydroxycarboxylic acid or ketone was produced, and trace residues and/or contaminants of the host cell. Such trace residues and/or contaminants include cellular material produced by the lysis of the host cell.

BRIEF DESCRIPTION OF THE DRAWINGS

The foregoing aspects and others will be readily appreciated by the skilled artisan from the following description of illustrative embodiments when read in conjunction with the accompanying drawings.

FIG. 1 shows the 3-hydroxycarboxylic acid molecules that can be produced using the invention. The PKS which synthesizes each 3-hydroxycarboxylic acid molecule is shown.

FIG. 2 shows the ketones molecules that can be produced using the invention. The PKS which synthesizes each ketone molecule is shown. The S1+E3+R2 PKS synthesizes the same ketone as S3+E1+R2 PKS. The S2+E3+R2 PKS synthesizes the same ketone as S3+E2+R2 PKS.

FIG. 15 shows structurally diverse ketone production by engineered PKSs. LipPks1 consists of a loading didomain (an $AT_L$ and an $ACP_L$), a KS, an AT, a KR, and an ACP domain. The phosphopantetheine prosthetic arm is shown as a wavy line. The extended polyketide chains tethered to the ACP domain are translocated to the downstream TE to release β-keto-carboxylic acids in the absence of NADPH or when the KR domain is inactivated. The corresponding ketones are accelerated when β-keto-carboxylic acids are heated. (A) Ethyl ketones produced by LipPks1+TE. (B) Methyl ketones produced by the LipPks1+TE mutant (mutant 75) where the native AT domain was replaced with an AT domain from the borrelidin PKS that is specific to malonyl-CoA.

DETAILED DESCRIPTION

Figure 3:
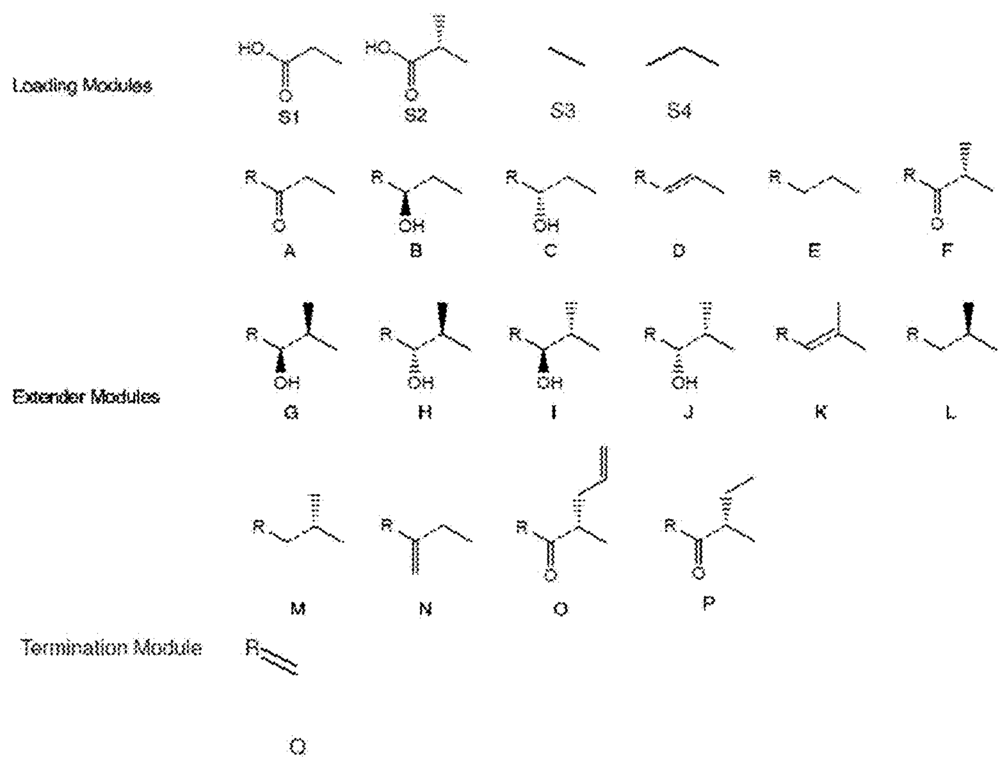
FIG. 3 shows types of modules employed and corresponding precursors utilized for incorporation into polyketide chains. The loading module is designated S. While any suitable loading domain can be used (such as those loading acetate and benzoic acid), only two examples are hereby shown. The remaining compounds represent the structures incorporated into the growing polyketide chain employing extender modules A-P. The dashed line indicates the C—C bond formed through Claisen condensation; atoms to the right of the bond and the C atom at the left of the dashed line represent the structures determined by the module employed. The R group represents the existing acyl chain prior to incorporation determined by the module.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms “a”, “and”, and “the” include plural referents unless the context clearly dictates otherwise. Thus, for example, reference to “a ketone” includes a plurality of such ketones, and so forth.

The term “functional variant” describes an enzyme that has a polypeptide sequence that is at least 70%, 75%, 80%, 85%, 90%, 95% or 99% identical to any one of the enzymes described herein. The “functional variant” enzyme may retain amino acids residues that are recognized as conserved for the enzyme, and may have non-conserved amino acid residues substituted or found to be of a different amino acid, or amino acid(s) inserted or deleted, but which does not affect or has insignificant effect its enzymatic activity as compared to the enzyme described herein. The “functional variant” enzyme has an enzymatic activity that is identical or essentially identical to the enzymatic activity of the enzyme described herein. The “functional variant” enzyme may be found in nature or be an engineered mutant thereof.

These and other objects, advantages, and features of the invention will become apparent to those persons skilled in the art upon reading the details of the invention as more fully described below.

Polyketide Synthases (PKS)

The present invention provides for a polyketide synthase (PKS) capable of synthesizing a 3-hydroxycarboxylic acid or ketone. The PKS is not a naturally occurring PKS. In some embodiments of the invention, the 3-hydroxycarboxylic acid or ketone is not a compound synthesized by a naturally occurring PKS. In some embodiments of the invention, the PKS is a hybrid PKS comprising modules, domains, and/or portions thereof, or functional variants thereof, from two or more PKSs.

In some embodiments of the invention, the 3-hydroxycarboxylic acid has the following chemical structure:

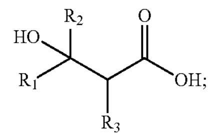

(I)

wherein $R_1$ is —H, each $R_2$ is independently —H, $—CH_3$, $—CH_2CH_3$, $—CH_2CH_2CH_3$, $—CH(CH_3)_2$, $—CH(CH_3)CH_2CH_3$, $—CH_2CH(CH_3)_2$, $—C_6H_{11}$, or $—C_6H_5$, and $R_3$ is independently —H, $—CH_3$, $—CH_2CH_3$, $—CH_2CH_2Cl$, $—CH_2CH{=}CH_2$, or $—CH_2CH_2COCH_3$. In some embodiments of the invention, the 3-hydroxycarboxylic acid is any one of the 3-hydroxycarboxylic acids shown in FIG. 1. The 3-hydroxycarboxylic acids includes the molecules having R and S forms independently at the α and β carbons.

In some embodiments of the invention, the ketone has the following chemical structure:

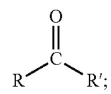

(II)

wherein each R is independently $—CH_3$, $—CH_2CH_3$, $—CH_2CH_2CH_3$, $—CH(CH_3)_2$, $—CH(CH_3)CH_2CH_3$, $—CH_2CH(CH_3)_2$, $—C_6H_{11}$, or $—C_6H_5$, and each R' is independently $—CH_3$, $—CH_2CH_3$, $—CH_2CH_2Cl$, $—CH_2CH{=}CH_2$, or $—CH_2CH_2COCH_3$. In some embodiments of the invention, the ketone is any one of the ketones shown in FIG. 2.

3-Hydroxycarboxylic acids can be polymerized chemically and biologically to produce polyesters with diverse functions. In order to produce 3-hydroxycarboxylic acids in microbes from renewable carbon sources such as sugars, one can engineer LipPks1, a polyketide synthase subunit of the lipomycin synthase. LipPks1 comprises of a loading acyltransferase domain, a loading acyl carrier protein domain, a ketosynthase domain, an acyltransferase (AT) domain, a ketoreductase (KR) domain, and an acyl carrier protein (ACP) domain. A thioesterase (TE) domain from the 6-deoxyriboerythronolide B synthase can be appended to the C-terminus of the ACP domain of LipPks1 (LipPks1+TE) to release the reaction intermediates attached onto the ACP domain as 3-hydroxycarboxylic acids. LipPks1+TE can be incubated with a variety of starter substrates (acyl-CoAs), the extension substrate (methylmalonyl-CoA), and nicotinamide adenine dinucleotide phosphate (NADPH) for the production of 3-hydroxy-2-methylpentanoic acid, 3-hydroxy-2-methylhexanoic acid, 3-hydroxy-2,4-dimethylpentanoic acid, 3-hydroxy-2,4-dimethylhexanoic acid, 3-hydroxy-2,5-dimethylhexanoic acid, and 3-hydroxy-2,4,4-trimethylpentanoic acid. Currently none of these molecules are not commercially available. By swapping the AT domain and the KR domain, and inserting a dehydratase (DH) domain and an enoyl reductase (ER) domain, one can produce over 150 different 3-hydroxycarboxylic acids, almost all of which are not commercially available.

In some embodiments, the PKS comprises (A) a LipPks1, or functional variant thereof, and (B) a thioesterase (TE) domain that catalyzes the same reaction as a TE of 6-deoxyriboerythronolide B synthase, wherein (B) is linked to the C-terminus of the ACP domain of (A).

Ketones can be used as solvents, flavors, and fragrances. For example, 2-butanone and 4-methyl-2-pentanone are industrially important solvents. 2-Pentanone is a food additive for human consumption permitted by U.S. Food and Drug Administration. 3-Ketocarboxylic acids can be converted into ketones by spontaneous decarboxylation. To produce ketones, NADPH can be removed from the above reactions. The following ketones can be produced: 3-pentanone, 3-hexanone, 2-methyl-3-pentanone, 4-methyl-3-hexanone, and 5-methyl-3-hexanone. By swapping the AT domain, one can produce over 50 different ketones, most of which are not commercially available. By further inactivating the KR domain, one can produce these ketones in microbes.

Complex polyketides comprise a large class of natural products that are synthesized in bacteria (mainly members actinomycete family; e.g. *Streptomyces*), fungi and plants. Polyketides form the aglycone component of a large number of clinically important drugs, such as antibiotics (e.g. erythromycin, tylosin), antifungal agents (e.g. nystatin), anticancer agents (e.g. epothilone), immunosuppressives (e.g. rapamycin), etc. Though these compounds do not resemble each other either in their structure or their mode of action, they share a common basis for their biosynthesis, which is carried out by a group of enzymes designated polyketide synthases.

Polyketide synthases (PKS) employ short chain fatty acyl CoAs in Claisen condensation reactions to produce polyketides. Unlike fatty acid synthases which utilize acetyl CoA as the starter and malonyl CoA as the extender units, and use a single module iteratively to produce the nascent acyl chains, PKSs are composed of discrete modules, each catalyzing the chain growth of a single step. Modules can differ from each other in composition so that overall, a number of different starters (e.g. acetyl CoA, propionyl CoA) and extenders, some of which contain stereospecific methyl (or ethyl) side chains can be incorporated. In addition, PKS modules do not always reduce the 3-carbonyl formed from condensation but may leave it either unreduced (ketone), partially reduced (hydroxyl, 2,3-ene) or fully reduced (3-methylene). Many polyketide synthases employ malonyl CoA or [S]-2-methylmalonyl CoA as the starter for polyketide synthesis. In such cases the terminal carboxyl group is usually removed by a decarboxylase domain present at the N-terminus of the corresponding loading domain of the PKS. In summary, the structure (and chirality) of the α-carbon and β-carbonyl is determined by the module of the PKS employed in the synthesis of the growing chain at each particular step. Because of the correspondence between use of modules in the synthesis and the structure of the polyketide produced, it is possible to program the synthesis to produce a compound of desired structure by selection and genetic manipulation of polyketide synthases. Hence, the programming of PKSs to produce dicarboxylic acids can be accomplished by straightforward removal of the N-terminal decarboxylase domain from the loading module. FIG. 3 shows the various modules and the precursor utilized by each module for incorporation into the corresponding nascent acyl (polyketide) chain to give rise to the range of compounds of interest. Table 1 provides a PKS source for each module (see FIG. 3). Each PKS source is well-known to one skilled in the art is readily available. In addition, for each module taught in Table 1, there may be other modules from other PKS that can be used. In addition, other structures can be incorporated in the ketide which are not shown in Table 1 and FIG. 3. For example, a loading module that can be used is the benzoate loading module of soraphen PKS, the isobutyrate loading module of the lipomycin PKS or bafilomycin PKS, or the acrylate loading module from the dificidin pathway. The acrylate loading module from the dificidin pathway is proposed to load lactate and dehydrate it to the arylyl-ACP (Chen, 2006, J. Bact. 188:4024-4036; hereby incorporated by reference).

The present invention includes the use of functional variants of the PKS modules, domains, and portions thereof.

TABLE 1

PKS sources of the various modules.

| Module | PKS Source |
|---|---|
| S1 | Spiramycin PKS Loading Domain (with inactivation or deletion of the $KS^Q$ domain) |
| S2 | Erythromycin PKS Loading Domain (with inactivation or deletion of the $KS^Q$ domain) |
| S3 | Spiramycin PKS Loading Domain |
| S4 | Erythromycin PKS Loading Domain |
| A | Rifamycin PKS Module 2 |
| B | Oligomycin PKS Module 1 |
| C | Spiramycin PKS Module 1 |
| D | Pikromycin PKS Module 2 |
| E | Oligomycin PKS Module 3 |
| F | Erythromycin PKS Module 3 |
| G | Oligomycin PKS Module 5 |
| H | Primaricin PKS Module 7 |
| I | Tylosin PKS Module 1 |
| J | Erythromycin PKS Module 1 |
| K | Avermectin PKS Module 7 |
| L | Rapamycin PKS Module 1 |
| M | Erythromycin PKS Module 4 |
| N | Pederin Module 2 |
| O | Ascomycin Module 4 |
| P | FK506 Module 4 |
| Q | Curacin A Chain Termination Module |

All extender modules carry the β-acyl ACP synthase (commonly called the ketosynthase or KS) domain, which conducts the decarboxylative condensation step between the extender and the growing polyketide chain, and the acyl carrier protein (ACP) domain that carries the growing acyl chain and presents it to the cognate reductive domains for reduction of the β-carbonyl. Modules can differ from each other in composition so that a number of different starter and extender units, some of which contain stereospecific side chains (e.g. methyl, ethyl, propylene) can be incorporated. The acyltransferase (AT) domain of each module determines the extender unit (e.g. malonyl CoA, methylmalonyl CoA, etc.) incorporated. In addition, PKS modules do not always reduce the β-carbonyl formed from condensation but may leave it either unreduced (ketone), partially reduced (hydroxyl, 2,3-ene) or fully reduced (3-methylene). The ketoreductase (KR) domain reduces the ketone to the OH function (stereospecifically); the dehydratase (DH) domain removes water from the α and β carbons leaving an α,β trans-double bond; the enoylreductase (ER) domain reduces the double bond to a β-methylene center; the reductive state of the β-carbonyl, therefore, is determined by the presence of functional reductive domains in the corresponding module. Less commonly, modules are found to contain an additional C-methylation domain (yielding an additional α-methyl side chain, as in epothilone). The makeup of the PKS, therefore, determines the choice of starter and extender acyl units incorporated, the extent of reduction at each condensation step, and the total number of units added to the chain. The wide diversity of structures of polyketides seen in nature is attributed to the diversity in PKS compositions.

A partial list of sources of PKS sequences that can be used in making the PKSs of the present invention, for illustration and not limitation, includes Ambruticin (U.S. Pat. No. 7,332,576); Avermectin (U.S. Pat. No. 5,252,474; MacNeil et al., 1993, Industrial Microorganisms: Basic and Applied Molecular Genetics, Baltz, Hegeman, & Skatrud, eds. (ASM), pp. 245-256; MacNeil et al., 1992, Gene 115: 119-25); Candicidin (FRO008) (Hu et al., 1994, Mol. Microbiol. 14: 163-72); Curacin A (Chang et al., 2004, *J. Nat. Prod*., 67 (8), pp 1356-1367; Gu et al., 2009, *J. Am. Chem. Soc*., 131 (44), pp 16033-16035); Epothilone (U.S. Pat. No. 6,303,342); Erythromycin (WO 93/13663; U.S. Pat. No. 5,824,513; Donadio et al., 1991, Science 252:675-79; Cortes et al., 1990, Nature 348:176-8); FK506 (Motamedi et al., 1998, Eur. J. Biochem. 256:528-34; Motamedi et al., 1997, Eur. J. Biochem. 244:74-80); FK520 or ascomycin (U.S. Pat. No. 6,503,737; see also Nielsen et al., 1991, Biochem. 30:5789-96); Jerangolid (U.S. Pat. No. 7,285,405); Leptomycin (U.S. Pat. No. 7,288,396); Lovastatin (U.S. Pat. No. 5,744,350); Nemadectin (MacNeil et al., 1993, supra); Niddamycin (Kakavas et al., 1997, J. Bacteriol. 179:7515-22); Oleandomycin (Swan et al., 1994, Mol. Gen. Genet. 242: 358-62; U.S. Pat. No. 6,388,099; Olano et al., 1998, Mol. Gen. Genet. 259:299-308); Pederin (PCT publication no. WO 2003/044186); Pikromycin (Xue et al., 2000, Gene 245:203-211); Pimaricin (PCT publication no. WO 2000/077222); Platenolide (EP Pat. App. 791,656); Rapamycin (Schwecke et al., 1995, Proc. Natl. Acad. Sci. USA 92:7839-43); Aparicio et al., 1996, Gene 169:9-16); Rifamycin (August et al., 1998, Chemistry & Biology, 5: 69-79); Soraphen (U.S. Pat. No. 5,716,849; Schupp et al., 1995, J. Bacteriology 177: 3673-79); Spiramycin (U.S. Pat. No. 5,098,837); Tylosin (EP 0 791,655; Kuhstoss et al., 1996, Gene 183: 231-36; U.S. Pat. No. 5,876,991). Additional suitable PKS coding sequences are readily available to one skilled in the art, or remain to be discovered and characterized, but will be available to those of skill (e.g., by reference to GenBank). Each of the references cited is hereby specifically and individually incorporated by reference.

Of the more than thirty PKSs examined, the correspondence between use of modules in the biosynthesis and the structure of the polyketide produced is fully understood both at the level of the protein sequence of the PKS and the DNA sequence of the corresponding genes. The programming of modules into polyketide structure can be identified by sequence determination. It is possible to clone (or synthesize) DNA sequences corresponding to desired modules and transfer them as fully functioning units to heterologous, otherwise non-polyketide producing hosts such as *E. coli* (B. A. Pfeifer, S. J. Admiraal, H. Gramajo, D. E. Cane, C. Khosla, *Science* 291, 1790 (2001); hereby incorporated by reference) and *Streptomyces* (C. M. Kao, L. Katz, C. Khosla, *Science* 265, 509 (1994); hereby incorporated by reference). Additional genes employed for polyketide biosynthesis have also been identified. Genes that determine phosphopantetheine:protein transferase (PPTase) that transfer the 4-phosphopantetheine co-factor of the ACP domains, commonly present in polyketide producing hosts, have been cloned in *E. coli* and other hosts (K. J. Weissman, H. Hong, M. Oliynyk, A. P. Siskos, P. F. Leadlay, *Chembiochem* 5, 116 (2004); hereby incorporated by reference). It is also possible to re-program polyketide biosynthesis to produce a compound of desired structure by either genetic manipulation of a single PKS or by construction of a hybrid PKS composed of modules from two or more sources (K. J. Weissman, H. Hong, M. Oliynyk, A. P. Siskos, P. F. Leadlay, *Chembiochem* 5, 116 (2004); hereby incorporated by reference).

Recombinant methods for manipulating modular PKS genes to make the PKSs of the present invention are described in U.S. Pat. Nos. 5,672,491; 5,843,718; 5,830,750; 5,712,146; and 6,303,342; and in PCT publication nos. WO 98/49315 and WO 97/02358; hereby incorporated by reference. A number of genetic engineering strategies have been used with various PKSs to demonstrate that the structures of polyketides can be manipulated to produce novel polyketides (see the patent publications referenced supra and Hutchinson, 1998, Curr. Opin. Microbiol. 1:319-329, and Baltz, 1998, Trends Microbiol. 6:76-83; hereby incorporated by reference). In some embodiments, the components of the hybrid PKS are arranged onto polypeptides having interpolypeptide linkers that direct the assembly of the polypeptides into the functional PKS protein, such that it is not required that the PKS have the same arrangement of modules in the polypeptides as observed in natural PKSs. Suitable interpolypeptide linkers to join polypeptides and intrapolypeptide linkers to join modules within a polypeptide are described in PCT publication no. WO 00/47724, hereby incorporated by reference.

The vast number of polyketide pathways that have been elucidated provide a host of different options to produce these polyketides as well as the large number of derivatives. While the products can be vastly different in size and functionality, all employ virtually the same strategy for biosynthesis. The exact interfaces between non-cognate enzyme partners will be determined on a case-by-case basis. For example, ACP-linker-KS and ACP-linker-TE regions from the proteins of interest can be aligned to examine the least disruptive fusion point for the hybrid synthase. Genetic constructions will employ sequence and ligation independent cloning (SLIC) so as to eliminate the incorporation of genetic "scarring".

In some embodiments, the PKS capable of producing a 3-hydroxycarboxylic acid or ketone of interest can be produced by feeding or exogenously providing the appropriate starter CoA to the host cell comprising the PKS the various 3-hydroxycarboxylic acid or ketone can be produced. In some embodiments, a precursor molecule is required by the PKS to produce the polyketide of interest. The precursor molecule can be fed or exogenously provided to the host cell comprising the PKS, or the host cell can comprise the enzymes capable of biosynthesizing the precursor molecule from a simpler molecule that can be fed or exogenously provided to the host cell or the host cell naturally endogenously produces.

Nucleic Acids Encoding the PKS

The present invention provides for a recombinant nucleic acid that encodes a polyketide synthase (PKS) of the present invention. The recombinant nucleic acid can be a double-stranded or single-stranded DNA, or RNA. The recombinant nucleic acid can encode an open reading frame (ORF) of the PKS of the present invention. The recombinant nucleic acid can also comprise promoter sequences for transcribing the ORF in a suitable host cell. The recombinant nucleic acid can also comprise sequences sufficient for having the recombinant nucleic acid stably replicate in a host cell. The recombinant nucleic acid can be replicon capable of stable maintenance in a host cell. In some embodiments, the replicon is a plasmid. The present invention also provides for a vector or expression vector comprising a recombinant nucleic acid of the present invention. The present invention provides for a host cell comprising any of the recombinant nucleic acid and/or PKS of the present invention. In some embodiments, the host cell, when cultured under a suitable condition, is capable of producing the 3-hydroxycarboxylic acid or ketone.

It will be apparent to one of skill in the art that a variety of recombinant vectors can be utilized in the practice of aspects of the invention. As used herein, "vector" refers to polynucleotide elements that are used to introduce recombinant nucleic acid into cells for either expression or replication. Selection and use of such vehicles is routine in the art. An "expression vector" includes vectors capable of expressing DNAs that are operatively linked with regulatory sequences, such as promoter regions. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those that integrate into the host cell genome.

The vectors may be chosen to contain control sequences operably linked to the resulting coding sequences in a manner that expression of the coding sequences may be effected in an appropriate host. Suitable control sequences include those that function in eukaryotic and prokaryotic host cells. If the cloning vectors employed to obtain PKS genes encoding derived PKS lack control sequences for expression operably linked to the encoding nucleotide sequences, the nucleotide sequences are inserted into appropriate expression vectors. This can be done individually, or using a pool of isolated encoding nucleotide sequences, which can be inserted into host vectors, the resulting vectors transformed or transfected into host cells, and the resulting cells plated out into individual colonies. Suitable control sequences for single cell cultures of various types of organisms are well known in the art. Control systems for expression in yeast are widely available and are routinely used. Control elements include promoters, optionally containing operator sequences, and other elements depending on the nature of the host, such as ribosome binding sites. Particularly useful promoters for prokaryotic hosts include those from PKS gene clusters that result in the production of polyketides as secondary metabolites, including those from Type I or aromatic (Type II) PKS gene clusters. Examples are act promoters, tcm promoters, spiramycin promoters, and the like. However, other bacterial promoters, such as those derived from sugar metabolizing enzymes, such as galactose, lactose (lac) and maltose, are also useful. Additional examples include promoters derived from biosynthetic enzymes such as for tryptophan (trp), the β-lactamase (bla), bacteriophage lambda PL, and T5. In addition, synthetic promoters, such as the tac promoter (U.S. Pat. No. 4,551,433; hereby incorporated by reference), can be used.

As noted, particularly useful control sequences are those which themselves, or with suitable regulatory systems, activate expression during transition from growth to stationary phase in the vegetative mycelium. Illustrative control sequences, vectors, and host cells of these types include the modified *Streptomyces coelicolor* CH999 and vectors described in PCT publication no. WO 96/40968 and similar strains of *Streptomyces lividans*. See U.S. Pat. Nos. 5,672,491; 5,830,750; 5,843,718; and 6,177,262, each of which is hereby incorporated by reference. Other regulatory sequences may also be desirable which allow for regulation of expression of the PKS sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes that confer antibiotic resistance or sensitivity to the plasmid.

The various PKS nucleotide sequences, or a mixture of such sequences, can be cloned into one or more recombinant vectors as individual cassettes, with separate control elements or under the control of a single promoter. The PKS subunits or components can include flanking restriction sites to allow for the easy deletion and insertion of other PKS subunits. The design of such restriction sites is known to those of skill in the art and can be accomplished using the techniques described above, such as site-directed mutagenesis and PCR. Methods for introducing the recombinant vectors of the present invention into suitable hosts are known to those of skill in the art and typically include the use of $CaCl_2$ or other agents, such as divalent cations, lipofection, DMSO, protoplast transformation, conjugation, and electroporation.

Host Cells Comprising the PKS

The present invention provides for a host cell comprising any of the recombinant nucleic acid and/or PKS of the present invention. In some embodiments, the host cell, when cultured, is capable of producing a 3-hydroxycarboxylic acid or ketone. The host cell can be a eukaryotic or a prokaryotic cell. Suitable eukaryotic cells include yeast cells, such as from the genus *Saccharomyces* or *Schizosaccharomyces*. A suitable species from the genus *Saccharomyces* is *Saccharomyces cerevisiae*. A suitable species from the genus *Schizosaccharomyces* is *Schizosaccharomyces pombe*. Suitable prokaryotic cells include *Escherichia coli* or *Streptomyces* species, such as *S. coelicolor* and *S. lividans*.

The PKS can be in a host cell, or isolated or purified. The PKS can synthesize the 3-hydroxycarboxylic acid or ketone in vivo (in a host cell) or in vitro (in a cell extract or where all necessary chemical components or starting materials are provided). The present invention provides methods of producing the 3-hydroxycarboxylic acid or ketone using any of these in vivo or in vitro means.

The amino acid sequence of LipPks1 of *Streptomyces aureofaciens* Tü117 (GenBank accession no. Q30CS2) comprises:

```
                                                        (SEQ ID NO: 10)
        10         20         30         40         50         60
MAGPPPFPRR RGPSGRRRCG GRATPGSVRD RTGRRPAAVP SRAVCAADLC EENDDGSKNV

        70         80         90        100        110        120
SEHRGSAGGS VLFPRTGTVL PWVLTGPGAA AVRARSEALR THLRASTEWS PAGVGQALLA
```

-continued

```
        130        140        150        160        170        180
GTGAGADTHR AVVLAGDRAQ TLNALAALSA GADHPAVFTS TRADASPAGP VFVFPGQGSQ

        190        200        210        220        230        240
WTGMARELLD SAPVFARKLH DCADAFAPYL GHSLLDSVTG AAGGPEPVGA DVVQPALFAV

        250        260        270        280        290        300
MVALTDLWNA AGVAPGALLG HSLGELAAAH VAGVLSLDDS ARVVARWSQA QATLAGRGDM

        310        320        330        340        350        360
VSVLLPADEL ADLLDRRWPG RLVVAVENGP GSAVASGDLD AAAELVAHLT AEGIHARRVD

        370        380        390        400        410        420
VGLAAHSPHI DAILPRIRAD IAPIRAHTPS IPVYSALHGG ALDGTPMDAA YWCRNLRSTV

        430        440        450        460        470        480
RFADATRAAL EAGHTTFVEV SPHPVLTTAM EVSATRAAHA ATVLGTLRRG EGGPSRFLAS

        490        500        510        520        530        540
LAELHVSGGD ADLRTVLPAS QAAGLPETVL TAGPRGESAD GDSRHEVLCA RLAPLDPAER

        550        560        570        580        590        600
RAQLLTVVRE SAAAALDGDD QGSIDGRRTF RDLGITSLAA VGIRDRLHSA TGLRLSPTVV

        610        620        630        640        650        660
FDHPTPDALA AHLDTELFGT GADAEPAPAA GGRAVPHDEP MAIVGMACRY PGGVGAPADL

        670        680        690        700        710        720
WRTVLAGVDA VGPLPADRGW NIADGYDPEL AGPGRFSQRE GGFLHDAAEF DAEFFGISPR

        730        740        750        760        770        780
EALAMDPQQR LALESAWEAI EDAGLDAHSL RGSRTGVFLG LITQDYGPRA GEPTTRAGAV

        790        800        810        820        830        840
EGHLFLGSTG SVASGRLSYT LGLEGPSLTI DTACSSSLVA LHEACQALRT GDCDMALTGG

        850        860        870        880        890        900
VTVMPSTGML VEFSRQRGLS PDGRCKAFSA SADGFGLAEG VGMLVVERLS DARRLGHRVL

        910        920        930        940        950        960
AVVRGSAVNQ DGASNGLSAP SGPAQQRVIR QALVNAGVQA SQVDVVEAHG TGTKLGDPIE

        970        980        990       1000       1010       1020
AQALQATYGQ GRPAERPLWL GSLKSNIGHA QAAAGVGGVI KMVMALREGV LPPTLHADEP

       1030       1040       1050       1060       1070       1080
SPHIDWSAGQ VRLLTEEREW PEAGHPRRAA VSSFGVSGTN AHVILEAAPG TGGAPEVSDG

       1090       1100       1110       1120       1130       1140
VLGSAPETVP WVLSAASPDA LRAQAERLRG HVAERPGLAS ADVAFALATR RTALEYRAVA

       1150       1160       1170       1180       1190       1200
VGAERDELLD TLDALSAGRP APRAVPGDAA AHSRRPVFVF PGQGSQWAGM AVELLDSSPV

       1210       1220       1230       1240       1250       1260
FADSMHACSE ALNEFVDWNL LEVLRSGDEE LSNRVDVVQP VLWAVMVSLA ALWQACGVRP

       1270       1280       1290       1300       1310       1320
AAVVGHSQGE IAAAVVAGAL SLRDGARVVA LRSAVIARLL AGKGAMASVA LASDTVRERL

       1330       1340       1350       1360       1370       1380
TPWEGRLSLA AVNGPSSSVV CGHLDALDEF VSALEHDGVR VRRIAVDYAS HSVFVEQAEE

       1390       1400       1410       1420       1430       1440
ELRNVLTEVS PLPGQVPFYS TVTGAVLDTT TLDAGYWYRN LRQTVRFEET VRELTRRGHD

       1450       1460       1470       1480       1490       1500
AFIEVSAHPV LTVGIQDTLE ATGTRHAVCG TLRRGEGGAQ RLLTSLGEAW VAGIAVDWSR

       1510       1520       1530       1540       1550       1560
LTPTTTAVQL PTYAFQHQRY WLDSTTANTG DRPAADRDTA FWEAVQHTDL DAFAAELDIA

       1570       1580       1590       1600       1610       1620
PDAPLGTVLP ALADWRQRLR TAAAVDAWRY RTAFKRLPDA PGAPVLTGSW LAVVPVRHLD

       1630       1640       1650       1660       1670       1680
DPSVTTSLDA VAKAGAEVVQ LAIEDADADV DRLTERLRGL VAGLGAAPAG IMSFLGLDEE

       1690       1700       1710       1720       1730       1740
RHRDHPAMPS GLATSLALVR ALGRAGIGAP LWMVTREAVA AGQDTHPHAP LGSLIWGLGQ
```

-continued

```
      1750       1760       1770       1780       1790       1800
VTALEHADRW GGLIDLPGVC DARVARMLCA GLSGRGAEDQ LALRPSGTFV RRLAHIPGEQ

      1810       1820       1830       1840       1850       1860
RAARRSWQPR GTVIVTGGTG ALGAVLARWL ATEDAEHLVL TGRRGADAPG AERLRDELVA

      1870       1880       1890       1900       1910       1920
TGARVTLAAC DVADRKAVAA LLDELAADGE TVRAVLHAAG VADLTSLENT GPEAFAAGVA

      1930       1940       1950       1960       1970       1980
AKVDGALHLT ELLDHDSLDA FVLFSSIAGV WGSGDHGAYA AANAFLNALA EYNRARGIPT

      1990       2000       2010       2020       2030       2040
TSIAWGVWNA FGVEGAGGIS EAVDLDQLHR RGLPLIEPEL GLTALRRALD RDETVLTVAP

      2050       2060       2070       2080       2090       2100
VAWERFFPLF SAARPRPLFE DLPQVRALSA PVPTTAGPAV EPGRRGSGLG DLPLTDRDSA

      2110       2120       2130       2140       2150       2160
LLALVRGESA SVLGYERPDR LDPDRALRDV GFDSLTAMEL RNRLATATGL TLPAALVFDH

      2170       2180       2190       2200       2210       2220
PTPLAIAAYL KAELYGPDPG DDSSVLTELD GLSQRLAAID PDTNTRLEIT LRLRSLLTQW

      2230       2240       2250
SEPDGGRTTA ETATATSTTA LESASADEVL AFIDTELGI
```

Methods of Using the PKS

The present invention provides a method of producing a 3-hydroxycarboxylic acid or ketone, comprising: providing a host cell of the present invention, and culturing said host cell in a suitable culture medium such that the 3-hydroxycarboxylic acid or ketone is produced. The method can further comprise isolating said 3-hydroxycarboxylic acid or ketone from the host cell and the culture medium. A variety of methods for heterologous expression of PKS genes and host cells suitable for expression of these genes and production of polyketides are described, for example, in U.S. Pat. Nos. 5,843,718; 5,830,750 and 6,262,340; WO 01/31035, WO 01/27306, and WO 02/068613; and U.S. Patent Application Pub. Nos. 20020192767 and 20020045220; hereby incorporated by reference.

The present invention provides for a composition comprising a 3-hydroxycarboxylic acid or ketone isolated from a host cell from which the 3-hydroxycarboxylic acid or ketone is produced, and trace residues and/or contaminants of the host cell. Such trace residues and/or contaminants include cellular material produced by the lysis of the host cell.

References Cited:

(1) Khosla, C., Tang, Y., Chen, A. Y., Schnarr, N. A., and Cane, D. E. (2007) *Annu. Rev. Biochem*. 76, 195-221.

(2) Bihlmaier, C., Welle, E., Hofmann, C., Welzel, K., Vente, A., Breitling, E., Muller, M., Glaser, S., and Bechthold, A. (2006) *Antinticrob. Agents Chemother*. 50, 2113-2121.

(3) Schulman, M. D., Valentino, D., and Hensens, O. (1986) *J. Antibiot*. 39, 541-549.

(4) Chen, T. S., Arison, B. H., Gullo, V. P., and Inamine, E. S. (1989) *J. Ind. Microbiol*. 4, 231-238.

(5) Cane, D. E., Liang, T.-C., Kaplan, L. K., Nallin, M. K., Schulman, M. D., Hensens, O. D., Douglas, A. W., and Albers-Schonberg, G. (1983) *J. Am. Chemn. Soc*. 105, 4.110-4112.

(6) Murli, S., Kennedy, J., Dayem, L. C., Carney, J. R., and Kealey, J. T. (2003) *J. Ind. Microbiol*. Biotechnol. 30, 500-509.

(7) Staunton, J., Caffrey, P., Aparicio, J. F., Roberts, G. A., Bethell, S. S., and Leadlay, P. F. (1996) *Nat. Struct Biol*. 3, 188-192.

(8) Tsai, S. C., Miercke, L. J., Krucinski, J., Gokhale, R, Chen, J. C., Foster, P. G., Cane, D. E., Khosla, C., and Stroud, R. M. (2001) *Proc. Natl. Acad. Sci. U.S.A*. 98, 14808-14813.

(9) Tang, Y., Kim, C. Y., Mathews, I. I., Cane, D. E., and Khosla, C. (2006) *Proc. Natl. Acad. Sci. U.S.A*. 103, 11124-11129.

(10) Van Draanen, N. A., Arseniyadis, S., Crimmins, M. T., and Heathcock, C. H. (1991) *J. Org. Chem*. 56, 2499-2506.

(11) Pieper, R., Ebert-Khosla, S., Cane, D., and Khosla, C. (1996) *Biochemistry* 35, 2054-2060.

(12) Jacobsen, J. R., Cane, D. E., and Khosla, C. (1998) *Biochemistry* 37, 4928-4934.

(13) Weissman, K. J., Bycroft, M., Staunton, J., and Leadlay, P. F. (1998) *Biochemistry* 37, 11012-11017.

(14) Hafner, E. W., Holley, B. W., Holdom, K. S., Lee, S. E., Wax, R. G., Beck, D., McArthur, H. A., and Wernau, W. C. (1991) *J. Antibiot*. 44, 349-356.

(15) Dutton, C. J., Gibson, S. P., Goudie, A. C., Holdom, K. S., Pacey, M. S., Ruddock, J. C., Bu'Lock, J. D., and Richards, M. K. (1991) *J. Antibiot* 44, 357-365.

(16) Kunze, B., Schabach, K., Zeeck, A., and Zahner, H. (1972) *Arch. Mikrobiol*. 86, 147-174.

(17) Liou, G. F., Lau, J., Cane, D. E., and Khosla, C. (2003) *Biochemistry* 42, 200-207.

The invention having been described, the following examples are offered to illustrate the subject invention by way of illustration, not by way of limitation.

EXAMPLE 1

Broad Substrate Specificity of the Loading Didomain of the Lipomycin Polyketide Synthase Multimodular polyketide synthases (PKSs) are among the largest (2-7 MDa) and most complex enzymes known. They conduct a programmed, stepwise catalysis that leads to the generation of poly-β-ketones with varying degrees of reductions at the β-carbonyl centers. Polyketides are widely used as antibiotics and other pharmaceutical agents.

Multimodular PKSs are composed of several large polypeptides. Each polypeptide contains one or more modules, each of which minimally consists of a ketosynthase (KS) domain, an acyltransferase (AT) domain, and an acyl carrier protein (ACP) domain that are together responsible for a single round of decarboxylative condensation (polyketide chain elongation reaction). The module may contain a loading AT ($AT_L$) and a loading ACP ($ACP_L$) to catalyze the polyketide chain initiation reaction. It may also contain a ketoreductase (KR) domain, a dehydratase (DH) domain, and an enoyl reductase (ER) domain to reduce the newly generated β-ketone on the growing polyketide chain tethered to the ACP domain. The extended polyketide chain is then translocated to the KS domain in the next module in the same polypeptide or to the KS in another protein for subsequent condensation. Alternatively, chain growth is terminated by a thioesterase (TE) domain. Understanding the mechanism for this orderly process represents a fundamental challenge in assembly line enzymology.(1)

The fidelity and efficiency of the entire process are dictated by two levels of molecular recognition: protein-protein recognition and substrate specificity. To address the issue of intrinsic substrate specificity, we studied LipPks1, a PKS subunit of the lipomycin synthase from *Streptomyces aureofaciens* Tü117, which is a PKS nonribosomal peptide synthase hybrid that catalyzes the biosynthesis of β-lipomycin, the aglycone of acyclic polyene antibiotic α-lipomycin (FIG. 4A).(2) LipPks1 is composed of an $AT_L$ domain, an $ACP_L$ domain, a KS domain, an AT domain, a KR domain, and an ACP domain, a simple PKS that catalyzes polyketide chain initiation and elongation reactions. Bihlmaier, Bechthold, and co-workers have described a model in which LipPks1 initiates the synthesis using isobutyryl-CoA and elongates once with methylmalonyl-CoA.(2) The model was based on the structure of the corresponding segment of α-lipomycin and the amino acid sequence similarity between the $AT_L$ domain of LipPks1 and the $AT_L$ domain of the avermectin PKS, which is believed to initiate polyketide synthesis using 2-methylbutyryl-CoA or isobutyryl-CoA as the starter substrate.(3-5)

Figure 4:
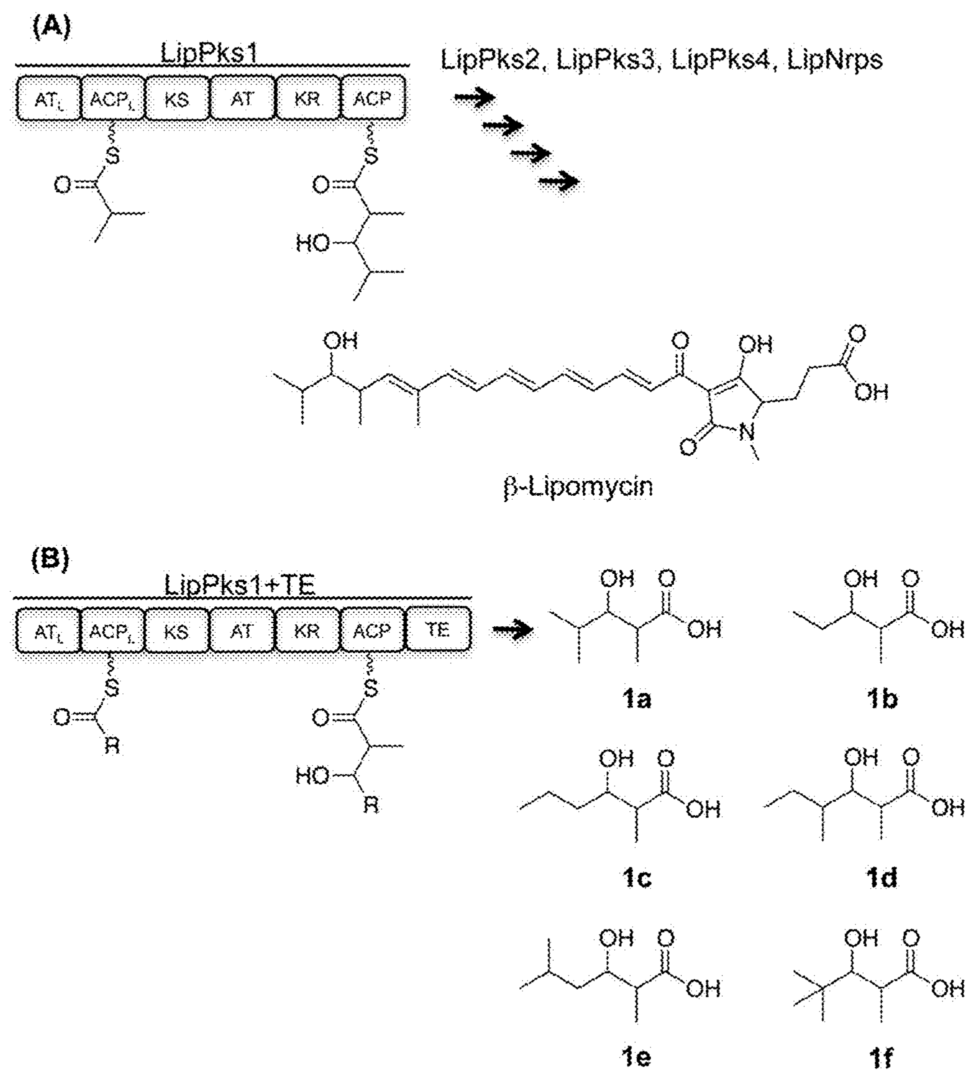
FIG. 4 shows (A) Polyketide chain initiation and elongation reactions catalyzed by LipPks1. LipPks1 consists of an $AT_L$ domain, an $ACP_L$ domain, a KS domain, an AT domain, a KR domain, and an ACP domain. The phosphopantetheine prosthetic arm is shown as a wavy line. The extended polyketide chain tethered to the ACP domain is translocated to the downstream LipPks2 to complete the β-lipomycin biosynthesis. (B) Broad substrate specificity of LipPks1+TE. Enzymatic production of 1a-f was confirmed by liquid chromatography-mass spectrometry analysis.

To test the model biochemically, we constructed an expression vector that encodes N-terminal hexahistidine tagged LipPks1 with the TE domain from the 6-deoxyerythronolide B synthase (DEBS) from *Saccharopolyspora erythraea* (LipPks1+TE) to release intermediates tethered to the ACP domain (FIG. 4B). We also constructed expression vectors encoding the protein that lacks the proline and arginine-rich N-terminal linker [(−NL)LipPks1+TE] and the TE-truncated version, which is essentially LipPks1. We used *Escherichia coli* K207-3 as a host for expression of the different PKS gene sets. *E. coli* K207-3 is an engineered strain whose genome encodes sfp from *Bacillus subtilis* that encodes the substrate promiscuous surfactin phosphopantetheinyl transferase that converts the expressed PKS apoproteins to their corresponding holo forms.(6) *E. coli* K207-3 is described in Pfeifer, et al. ((2001) *Science* 291, 1790-1792, and Murli, et al. ((2003) *J Ind Microbiol Biotechnol* 30, 500-509).

Protein production was analyzed by sodium dodecyl sulfatepolyacrylamide gel electrophoresis. LipPks1+TE was almost exclusively produced in the soluble fraction (FIG. 6A). (−NL)LipPks1+TE was also produced in the soluble fraction, although a significant amount was insoluble. In addition, the lysate displayed a large amount of soluble protein running in the gel between 160 and 260 kDa, suggesting that the proline and arginine-rich linker is contributing to stable protein folding, at least in *E. coli*. Surprisingly, a relatively low level of production was observed for LipPks1. This protein corresponds to a natural LipPks1 but lacks the C-terminal linker that is proposed to bind the N-terminal linker of the LipPks2 subunit. This result may suggest that the linker itself stabilizes the LipPks1 structure. Structural studies of DEBS, which is the most extensively studied multimodular PKS, demonstrated that each module forms a homodimer and that homodimerization is driven by the KS domains and the TE domain.(7-9) One possible explanation of the soluble and relatively stable production of LipPks1+TE is that adding a TE domain stabilized the homodimeric structure of LipPks1. LipPks1+TE was purified by Ni affinity chromatography followed by anion exchange chromatography to yield 2 mg of protein from 1 L of *E. coli* culture (FIG. 6C).

Figure 5:
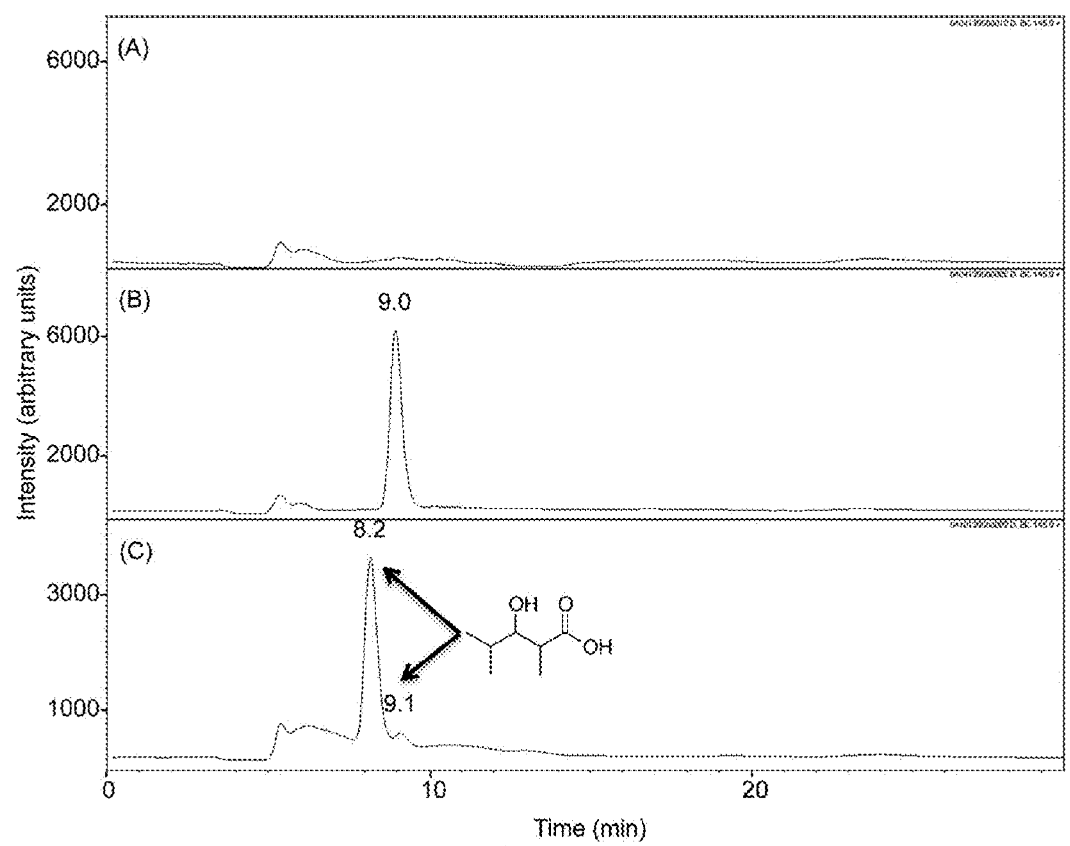
FIG. 5 shows LC-MS analysis of the in vitro biosynthesis of 1a. Isobutyryl-CoA (320 μM) and methylmalonyl-CoA (200 μM) were incubated for 17 h at 23° C. with 500 μM NADPH in the absence (A) or presence (B) of LipPks1+TE (0.5 μM). The resulting reaction mixtures were analyzed by LCMS in the selected ion monitoring mode (m/z 145). (C) LC-MS analysis of the chemically synthesized authentic standard (16 μM). The two peaks indicated by arrows are diastereomers of 1a. Retention times are shown atop the peaks.
Figures 6, 7:
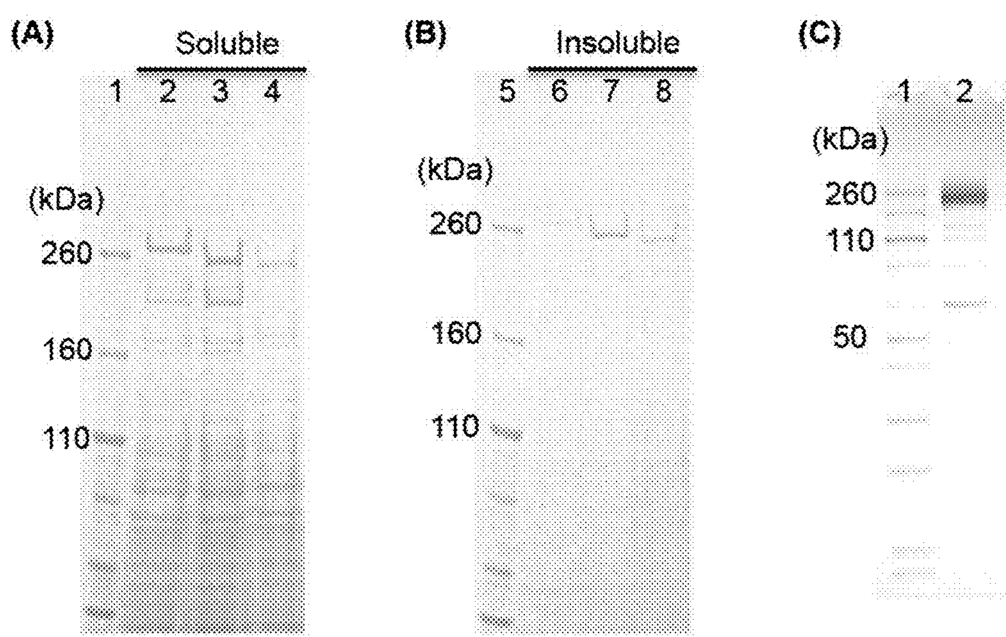
FIG. 6 shows SDS-PAGE analysis of recombinant LipPks1+TE (259 kDa), (−NL)LipPks1+TE (239 kDa), and LipPks1 (229 kDa). Proteins were resolved by 3-8% tris-acetate gel and stained with Coomassie blue. (A) Soluble fractions. (B) Insoluble fractions. Lanes 1 and 5, molecular weight markers; 2 and 6, His-LipPks1+TE; 3 and 7, His-(−NL)LipPks1+TE; 4 and 8, His-LipPks1. (C) Purity of recombinant LipPks1+TE. The protein purified from *E. coli* K207-3 was analyzed by SDS-PAGE (4-20% tris-glycine gel) and stained with Coomasie blue. Lane 1, molecular weight markers; 2, His-LipPks1+TE.
FIG. 7 shows the sequence comparison between A2-type KR domains. A-2 type KR domains yield the corresponding (2S,3S) products[6]. The conserved tryptophan and histidine residues of A-2 type KR domains are highlighted.

Isobutyryl-CoA, methylmalonyl-CoA, and NADPH were incubated with or without LipPks1+TE, and the production of 3-hydroxy-2,4-dimethylpentanoate (1a) was monitored by liquid chromatography and mass spectroscopy (LC-MS). The MS measurements were taken in the selected ion monitoring mode (m/z 145). As shown in FIG. 5B, a strong signal was observed in the presence of LipPks1+TE at 9.0 min. To confirm the production, we chemically synthesized 1a. The $^1H$ NMR data indicated that the compound was a mixture of diastereomers (26:1 syn:anti).(10) We analyzed the authentic standard by LC-MS and observed two peaks at 8.2 and 9.1 min (FIG. 5C). The product generated by LipPks1+TE appears to have the same stereochemistry as the second peak, which is (2S,3S)-1a and/or (2R,3R)-1a. The amino acid sequence of the KR domain suggests the 2S,3S product (FIG. 7). We also monitored the β-keto product of 1a by LCMS (m/z 143). No product was observed in the presence of NADPH (data not shown). The steady-state kinetic parameters for the reaction were determined: $k_{cat}$=0.053 $min^{-1}$; $K_M$(isobutyryl-CoA)=2.9 μM; and $K_M$(methylmalonyl-CoA)=1.3 μM (Table 2).

Figure 8:
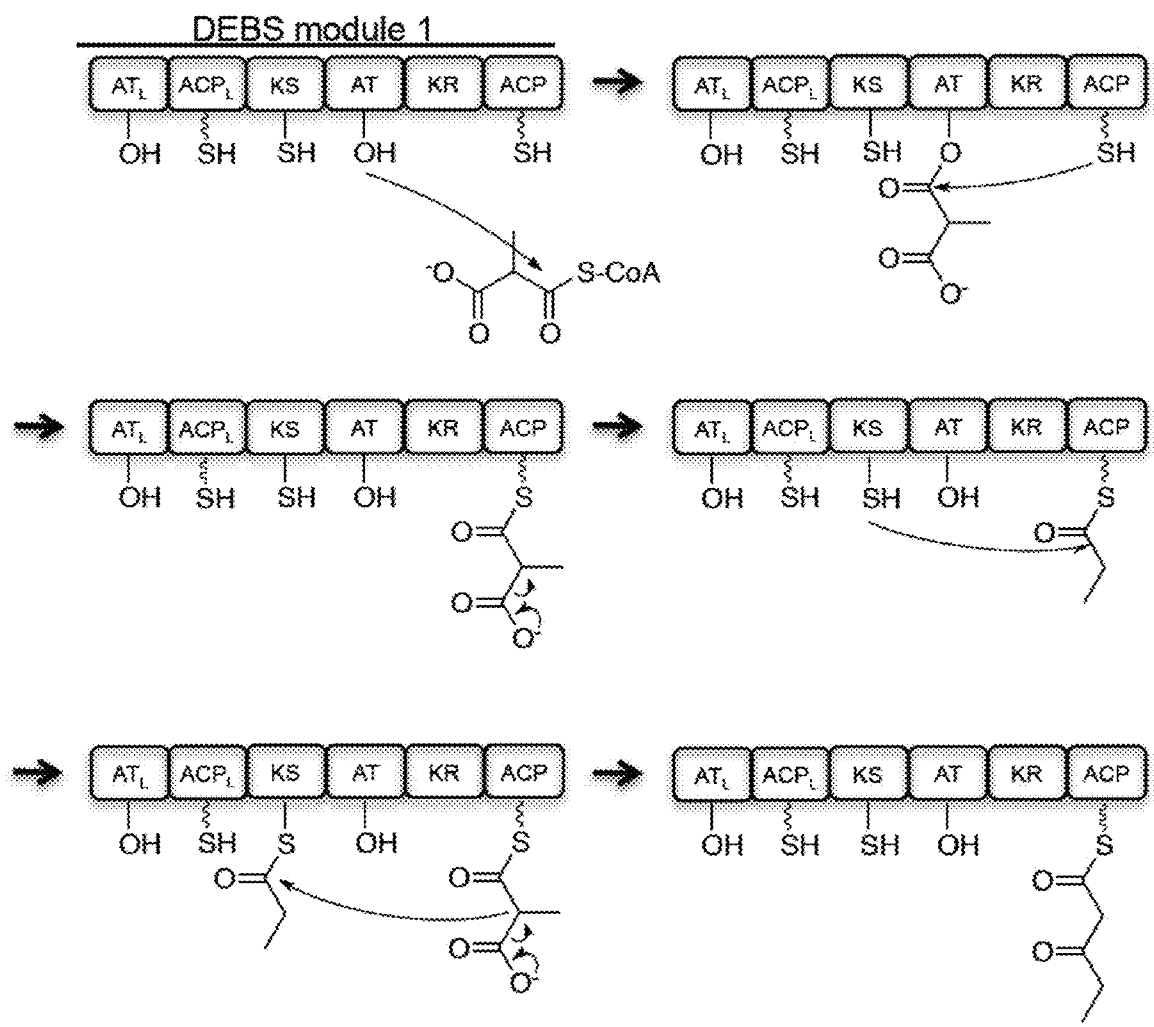
FIG. 8 shows chain elongation reaction catalyzed by the module 1 of DEBS1 using methylmalonyl-CoA as a sole substrate. The module 1 consists of an ATL, an ACPL, a KS, an AT, a KR, and an ACP domain. The phosphopantetheine prosthetic arm is shown as a wavy line. In the absence of propionyl-CoA, the KS can be primed by the propionyl group on the ACP generated by decarboxylation of the methylmalonyl extender unit. Decarboxylative condensation then occurs between the propionyl group on the KS and the newly generated methylmalonyl extender unit on the ACP.
Figure 9:
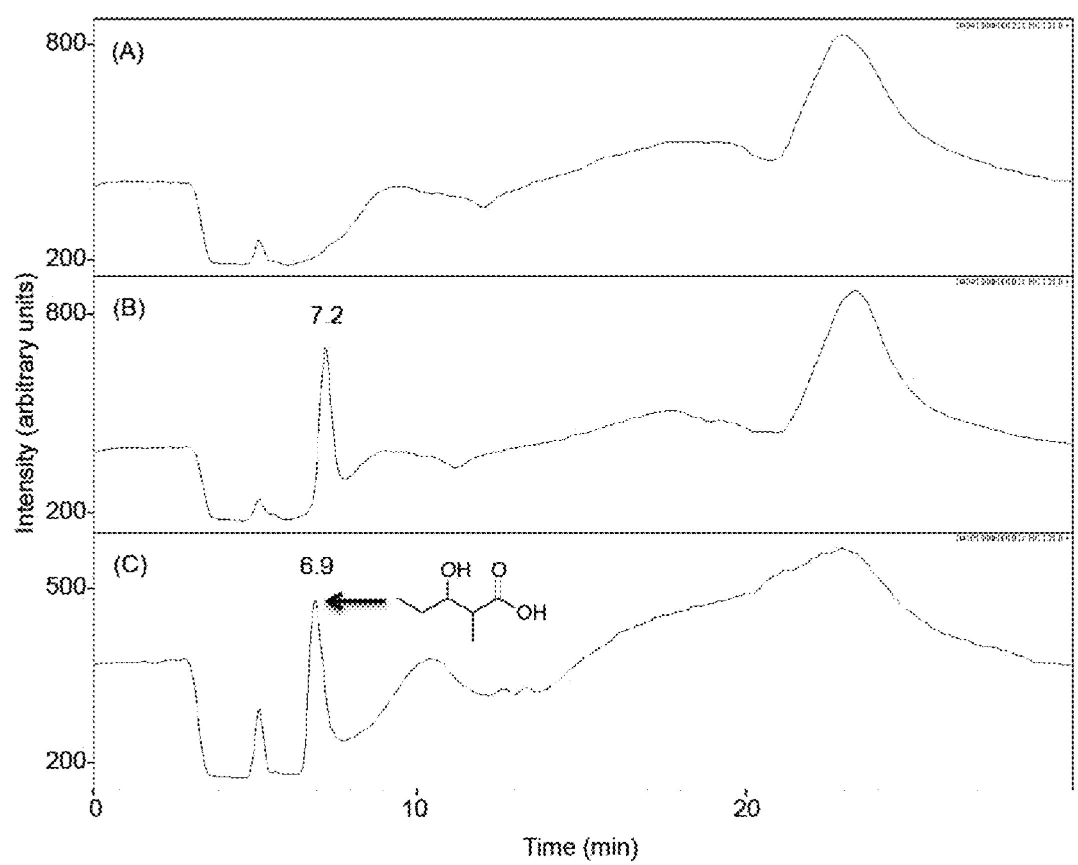
FIG. 9 shows LC-MS analysis of in vitro biosynthesis of 1b. Propionyl-CoA (320 μM) and methylmalonyl-CoA (200 μM) were incubated for 17 h at 23° C. with 500 mM NADPH in the absence (A) or the presence (B) of LipPks1+TE (0.5 μM). The resulting reaction mixtures were analyzed by LC-MS in the selected ion-monitoring mode (m/z=131). (C) LC-MS analysis of the chemically synthesized authentic standard (16 μM). Retention times are shown on the top of the peaks.
Figure 10:
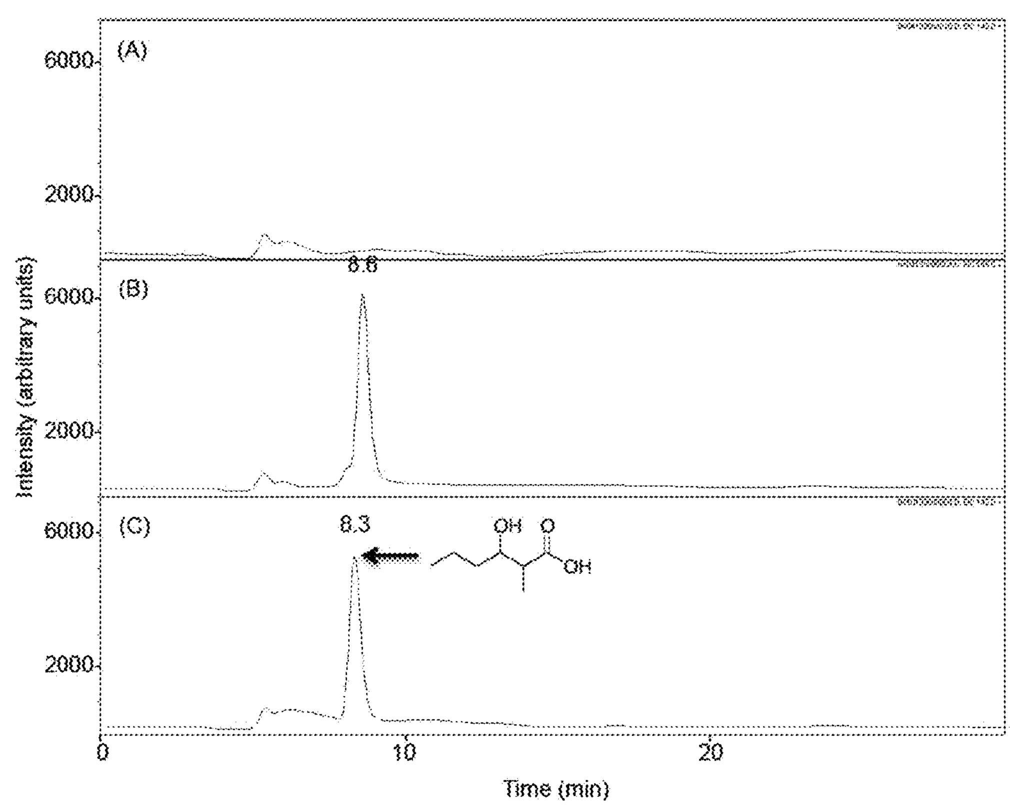
FIG. 10 shows LC-MS analysis of in vitro biosynthesis of 1c. n-Butyryl-CoA (320 μM) and methylmalonyl-CoA (200 μM) were incubated for 17 h at 23° C. with 500 mM NADPH in the absence (A) or the presence (B) of LipPks1+TE (0.5 μM). The resulting reaction mixtures were analyzed by LC-MS in the selected ion-monitoring mode (m/z=145). (C) LC-MS analysis of the chemically synthesized authentic standard (16 μM). Retention times are shown on the top of the peaks.
Figure 11:
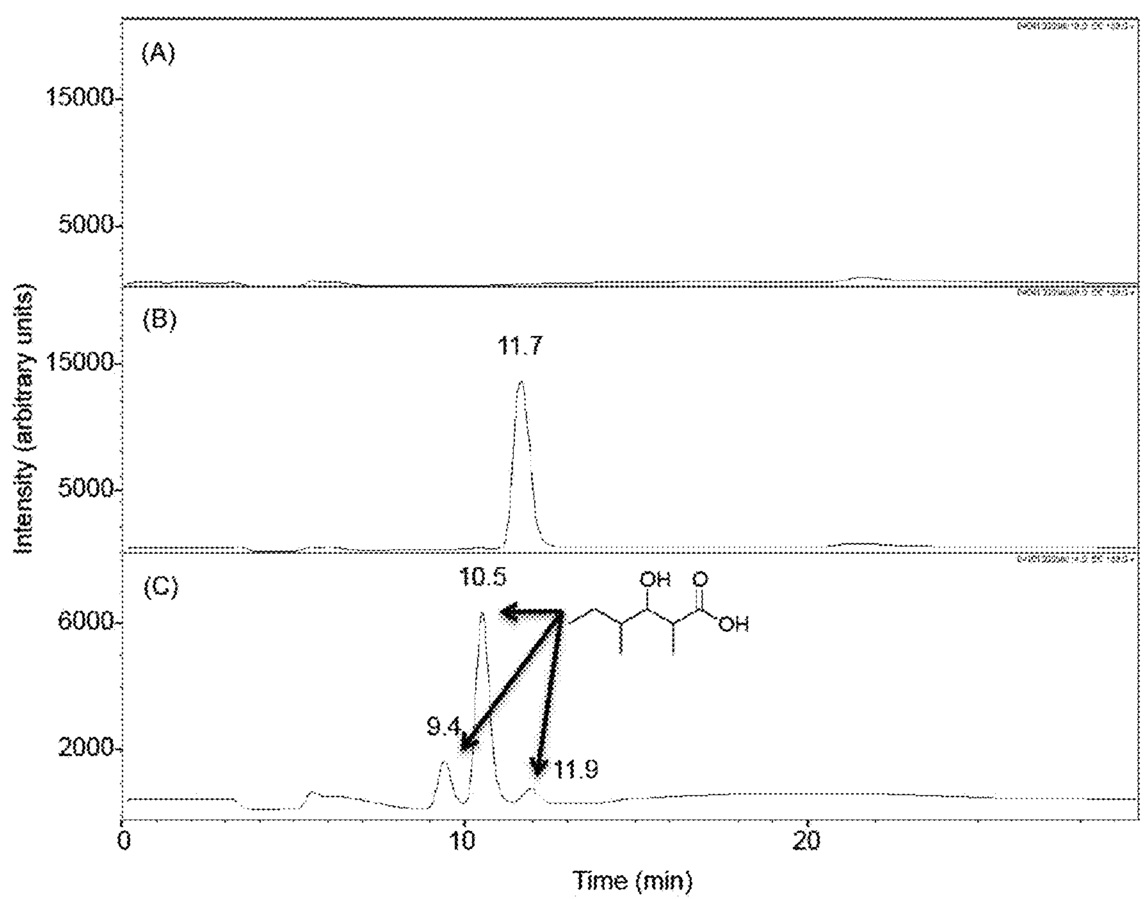
FIG. 11 shows LC-MS analysis of in vitro biosynthesis of 1d. 2-Methylbutyryl-CoA (320 μM) and methylmalonyl-CoA (200 μM) were incubated for 17 h at 23° C. with 500 mM NADPH in the absence (A) or the presence (B) of LipPks1+TE (0.5 μM). The resulting reaction mixtures were analyzed by LC-MS in the selected ion-monitoring mode (m/z=159). (C) LC-MS analysis of the chemically synthesized authentic standard (16 μM). The three peaks indicated by arrows are diastereomers of 1d. Retention times are shown on the top of the peaks.
Figure 12:
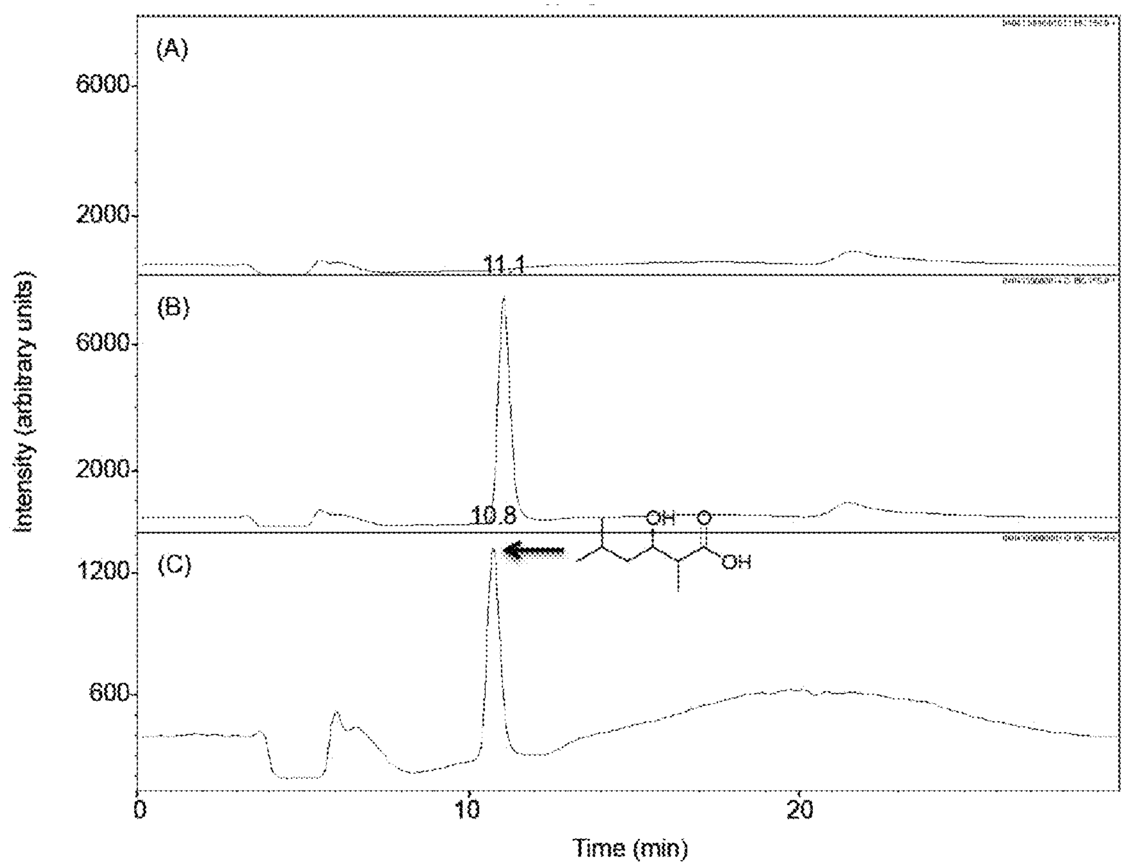
FIG. 12 shows LC-MS analysis of in vitro biosynthesis of 1e. Isovaleryl-CoA (320 μM) and methylmalonyl-CoA (200 μM) were incubated for 17 h at 23° C. with 500 mM NADPH in the absence (A) or the presence (B) of LipPks1+TE (0.5 μM). The resulting reaction mixtures were analyzed by LC-MS in the selected ion-monitoring mode (m/z=159). (C) LC-MS analysis of the chemically synthesized authentic standard (16 μM). Retention times are shown on the top of the peaks.
Figure 13:
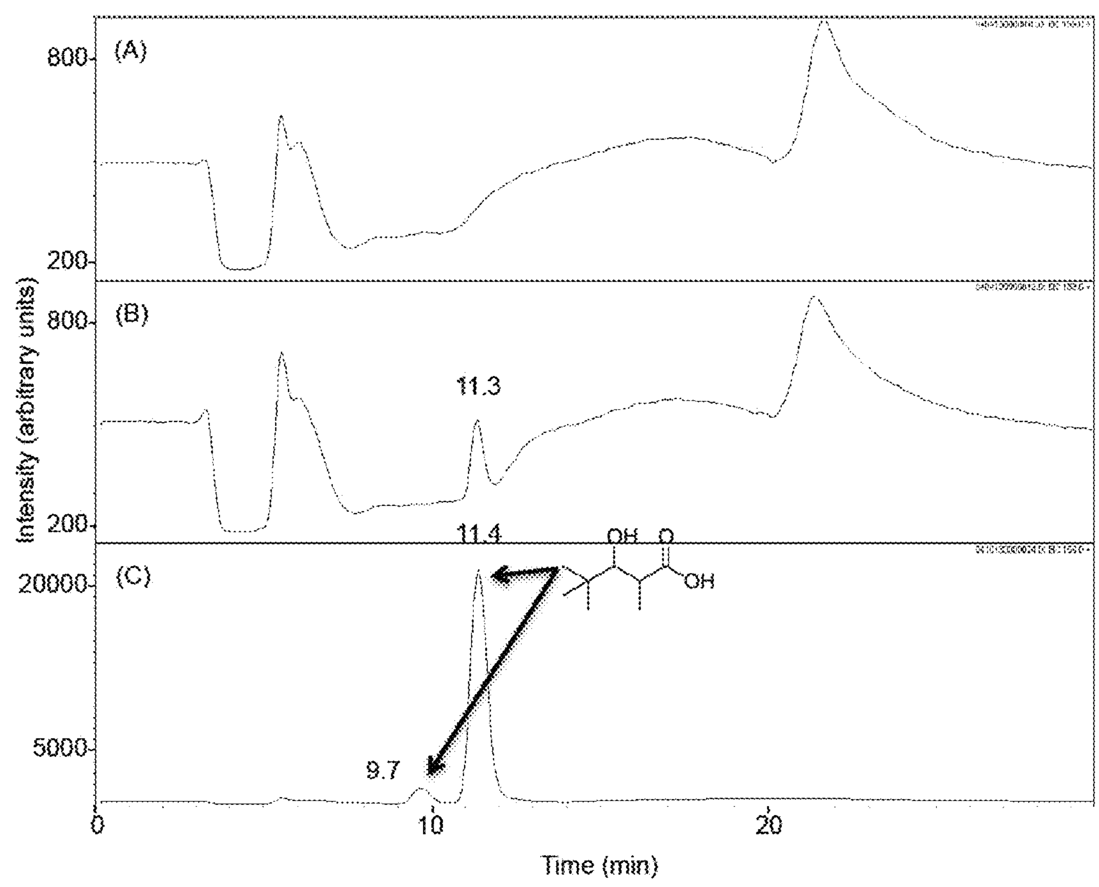
FIG. 13 shows LC-MS analysis of in vitro biosynthesis of 1f. Pivaloyl-CoA (320 μM) and methylmalonyl-CoA (200 μM) were incubated for 17 h at 23° C. with 500 mM NADPH in the absence (A) or the presence (B) of LipPks1+TE (0.5 μM). The resulting reaction mixtures were analyzed by LC-MS in the selected ion-monitoring mode (m/z=159). (C) LC-MS analysis of the chemically synthesized authentic standard (16 μM). The two peaks indicated by arrows are diastereomers of 1f. Retention times are shown on the top of the peaks.
Figure 14:
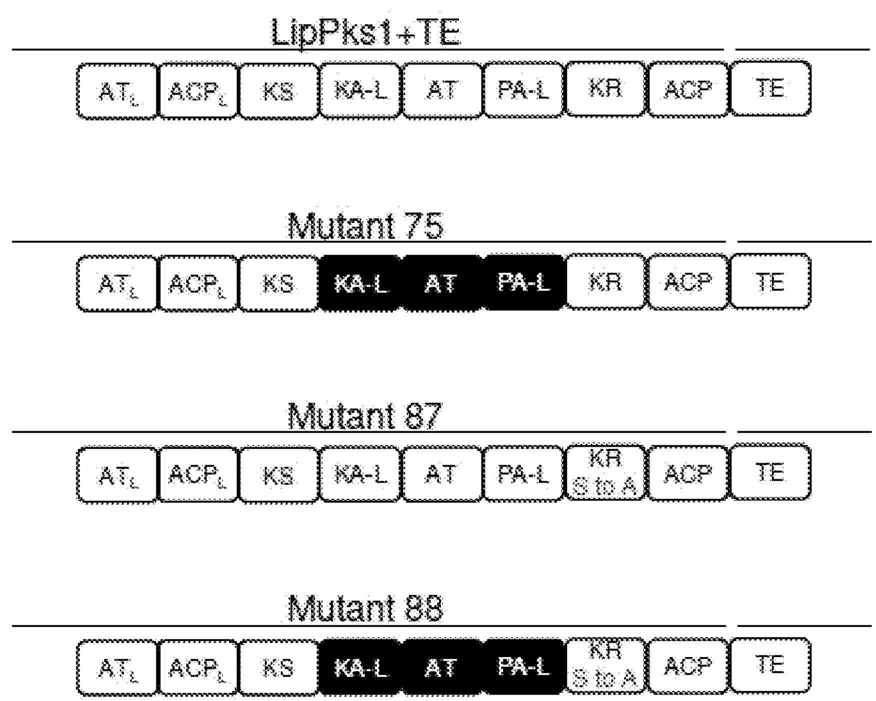
FIG. 14 shows engineered polyketide synthase (PKS) designs. Mutant 75: the KA-L-AT-PA-L of LipPks1+TE (starts from GTNAHVI and ends with PTTTAVQ (SEQ ID NO:5)) was replaced with KA-L-AT-PA-L from module 1 of the borrelidin PKS (starts from GTNAHVI and ends with PRARTVD (SEQ ID NO:6)). Mutant 87: the active site serine residue of KR domain (LFSSIAG, SEQ ID NO:7) of LipPks1+TE was mutated to alanine residue (LFSAIAG, SEQ ID NO:8). Mutant 88: the active site serine residue of KR domain (LFSSIAG, SEQ ID NO:7) of mutant 75 was mutated to alanine residue (LFSAIAG, SEQ ID NO:9). Abbreviations: ACP, acyl carrier protein; $ACP_L$, loading acyl carrier protein; AT, acyltransferase; $AT_L$, loading acyltransferase; KA-L, KS-AT linker; KR, ketoreductase; KS, ketosynthase; PA-L, post AT linker; TE, thioesterase.

To analyze the substrate specificity of the AT domain, we tested malonyl-CoA as a potential extender substrate. Malonyl-CoA was not accepted (data not shown), indicating the AT domain is specific for methylmalonyl-CoA. We also monitored production of 3-hydroxy-2-methylpentanoate (1b) by LC-MS (m/z 131) because DEBS1 was previously shown to start the catalytic cycle using methylmalonyl-CoA as a sole substrate where the methylmalonyl moiety on the ACP is decarboxylated by the KS domain, followed by transfer of the resulting propionyl group back to the KS domain where it could act as a primer for condensation with a new methylmalonyl-ACP extender (FIG. 8).(11-13) Production of 1b was not observed (data not shown), indicating that either the backtransfer reaction is slower than the rate-limiting step for 1a production or the KS does not accept a propionyl group. However, as descried below, the KS domain can accept the propionyl group as a starter, which refutes the latter hypothesis.

The amino acid sequence of the $AT_L$ domain of LipPks1 is 50% identical to that of the $AT_L$ domain of the avermectin PKS, which is known to accept a variety of starter substrates.(2) Previous studies showed that an engineered *Streptomyces avermitilis* produced more than 40 avermectin analogues when the culture was fed different carboxylic acids.(14, 15) To analyze the substrate tolerance of the $AT_L$ domain of LipPks1, we incubated the enzyme with acetyl-CoA, propionyl-CoA, n-butyryl-CoA, 2-methylbutyryl-CoA, isovaleryl-CoA, or pivaloyl-CoA at the saturation concentration of methylmalonyl-CoA (200 μM) with NADPH. No product was observed when acetyl-CoA was used as a starter substrate (data not shown). The other acyl-CoAs, however, gave the corresponding products, which are 3-hydroxy-2-methylpentanoate (1b), 3-hydroxy-2-methylhexanoate (1c), 3-hydroxy-2,4-dimethylhexanoate (1d), 3-hydroxy-2,5-dimethylhexanoate (1e), and 3-hydroxy-2,4,4-trimethylpentanoate (1f), which were confirmed by LC-MS analysis (m/z 131 for 1b, m/z 145 for 1c, and m/z 159 for 1d-f) with chemically synthesized authentic standards (FIGS. 9-13). The steady-state kinetic parameters for the reactions are listed in Table 2. The $k_{cat}/K_M$ values for isobutyryl-CoA and 2-methylbutyryl-CoA were comparable, which correlates well with avermectin biosynthesis in *S. avermitilis* in which isobutyryl- and 2-methylbutyryl-started products were isolated.(3, 5) Interestingly, the α-lipomycin analogue that would use 2-methylbutyryl-CoA as a starter was not observed in *S. aureofaciens* Tü117.(2, 16) One possibility is that the intracellular concentration of 2-methylbutyryl-CoA is far below the $K_M$ for LipPks1. The $k_{cat}$ values for all substrates investigated, except pivaloyl-CoA, were similar; the $k_{cat}$ value for pivaloyl-CoA was substantially lower than the others. The basis for the relatively low $k_{cat}$ with pivaloyl-CoA is not understood but may be related to the different rates of nucleophilic attack of the carbanion on the KS-linked substrates in the chain elongation reactions. These data suggest that production of α-lipomycin is tightly controlled by regulation of intracellular acyl-CoA concentrations.

The substrate specificity of the loading didomains of multimodular PKSs is usually assumed from the structure of the corresponding segment of polyketide products. However, this methodology depends on the products isolated under particular culture conditions, which might not reflect the actual substrate preference. The intrinsic substrate specificity can be determined by only in vitro kinetic analysis.(17) Our kinetic studies revealed broad substrate specificity of the loading didomain of LipPks1, highlighting the importance of using biochemistry to determine substrate flexibility.

TABLE 2

Steady-State Kinetic Parameters for the Formation of 1a-f by LipPks1 + TE

| substrate | product | $k_{cat}$ ($min^{-1}$) | $K_M$ (μM) | $k_{cat}/K_M$ ($M^{-1}$ $s^{-1}$) |
|---|---|---|---|---|
| isobutyryl-CoA | 1a | 0.053 | 2.9 | 304.1 |
| propionyl-CoA | 1b | 0.056 | 13.4 | 70.3 |
| n-butyryl-CoA | 1c | 0.036 | 26.4 | 22.7 |
| 2-methylbutyryl-CoA | 1d | 0.126 | 8.8 | 237.0 |
| isovaleryl-CoA | 1e | 0.290 | 128.1 | 38.0 |
| pivaloyl-CoA | 1f | 0.002 | 8.8 | 4.1 |

In summary, analyzing substrate specificity is crucial to our understanding of polyketide biosynthesis by multimodular PKSs and to the design of hybrid PKSs. In this work, we focus on the LipPks1 subunit of the lipomycin synthase and provide the first insights into substrate specificity. We have uncovered broad substrate specificity of the loading didomain, which was not anticipated from the study of the PKS in its native host and led us to speculate that novel lipomycin analogues can be produced by increasing intracellular acyl-CoA concentrations.

EXPERIMENTAL PROCEDURES

Chemicals

All chemicals were purchased from Sigma-Aldrich unless otherwise described.

Authentic Standard Synthesis

All NMR spectra were obtained on either a 400 MHz or a 600 MHz Bruker spectrometer. Chemical shifts (in ppm) were referenced to CDCl3 or D2O at room temperature (δ 1H=7.26 and δ 13C=77.16 for CDCl3, δ 1H=4.79 for D2O). A synthetic procedure analogous to that described for the synthesis of S2 and 1a was also used to obtain each of the final products 1b-f.

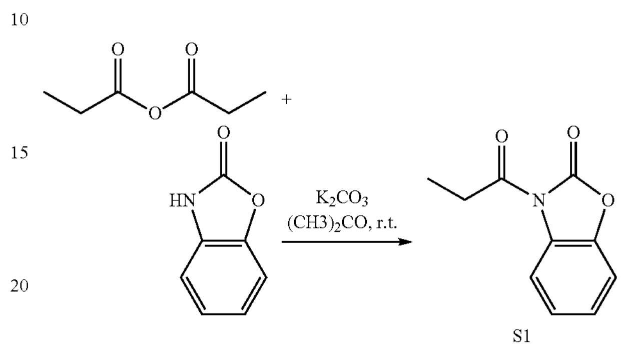

3-Propionylbenzo[d]oxazol-2(3H)-one (S1)

Following a reported procedure (Burlingame, M. A., Mendoza, E., and Ashley, G. W. (2004) Tetrahedron Lett 45, 2961-2964), a stirred solution of 2-benzoxazolonine (1 equiv, 102 mmol) in (CH3)2CO (90 mL) was treated with K2CO3 (1.15 equiv, 117 mmol) before addition of propionic anhydride (1 equiv, 102 mmol). The resulting mixture was stirred at room temperature (r.t.) for 3 h. The precipitated product was collected under filtration and dried in vacuo. Recrystallization in Et2O afforded a light tan solid, S1 (81.8 mmol, 80% yield). 1H NMR (CDCl3, 400 MHz) δ 8.09 (m, 1H), 7.24 (m, 3H), 3.15 (q, 2H), 1.29 (t, 3H).

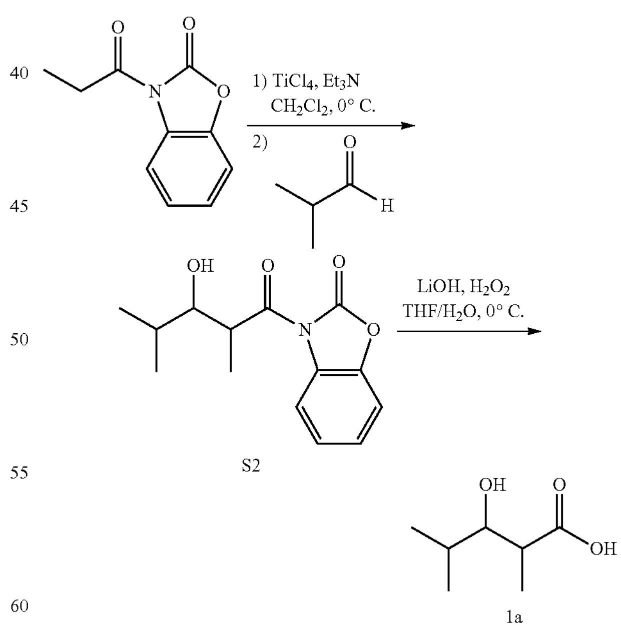

3-(3-Hydroxy-2,4-dimethylpentanoyl)benzo[d]oxazol-2(3H)-one (S2)

Following a modified reported procedure, 1 to a solution of S1 (1 equiv, 5.23 mmol) in anhydrous CH2Cl2 (8 mL) at 0° C. under N2 was added TiCl4 (1.1 equiv, 5.75 mmol) over 5 min, and the resulting bright yellow slurry stirred vigorously for 15 min. Triethylamine (1.1 equiv, 5.75 mmol) was then added to the solution over 5 min, and the consequent blood red solution stirred for an additional 50 min. Isobutyraldehyde (2 equiv, 10.46 mmol) was added slowly over 1 h, and the mixture was stirred for a further 1.5 h before quenching with one volume 1M HCl. The aqueous phase was extracted with EtOAc. The combined organic layers were then washed with 1 M HCl followed by saturated NaHCO3, and finally concentrated by rotary evaporation. Column chromatography followed by recrystallization in Et20/hexanes (1:1) afforded a white solid, S2 (2.54 mmol, 49% yield), which was used directly in the next step of the reaction procedure.

3-Hydroxy-2,4-dimethylpentanoic acid (1a)

Following a modified previously reported procedure (Evans, D. A., Britton, T. C., and Ellman, J. A. (1987) *Tetrahedron Lett* 28, 6141-6144), to a solution of S2 (1 equiv, 1.07 mmol) in THF (3 mL) at 0° C. was added a solution of LiOH (2 equiv, 2.14 mmol) and H2O2 (7 equiv, 7.49 mmol) in water (1 mL). The reaction was stirred at 0° C. for 4 h, and then quenched with one volume Na2SO4. The organic layer was removed via rotary evaporation. The aqueous layer was then washed with CH2Cl2, acidified with one volume 1 M HCl, and extracted with EtOAc. The combined organic layers were washed with 1 M HCl and then concentrated using a rotary evaporator. Column chromatography afforded a mixture of diastereomers as a tan/white solid, 1a (0.919 mmol, 86% yield). 1H NMR (400 MHz, CDCl3) δ 3.64 (dd, 1H), 2.72 (qd, 1H), 1.73 (m, 1H), [1.24, 1.21; 1:25] (d, 3H), [1.03, 0.99; 23:1] (d, 3H), [0.94, 0.89; 1:30] (d, 3H). 13C NMR (100 MHz, CDCl3) δ 182.03, 76.84, 41.92, 30.80, 19.20, 18.83, 9.93. ESI-MS (1a−H) C7H13O3−Mw=145.18, Observed=145.1.

3-Hydroxy-2-methylpentanoic acid (1b)

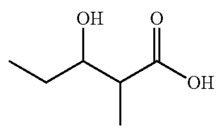

Yellow oil; 1H NMR (400 MHz, CDCl3) δ 6.93 (s br, 2H), 3.88 (ddd, 1H), 2.60 (qd, 1H), 1.50 (m, 2H), 1.18 (d, 3H), 0.96 (t, 3H). 13C NMR (150 MHz, CDCl3) δ 181.13, 73.53, 43.93, 26.75, 10.46, 10.39. ESI-MS (1b−H) C6H11O3−Mw=131.16, Observed=131.2.

3-Hydroxy-2-methylhexanoic acid (1c)

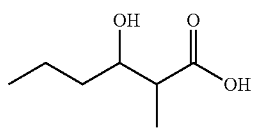

Brown oil; 1H NMR (400 MHz, CDCl3) δ 4.01 (ddd, 1H), 2.64 (qd, 1H), 1.55 (m, 2H), 1.47 (m, 2H), 1.25 (d, 3H), 0.99 (t, 3H). 13C NMR (150 MHz, CDCl3) δ 180.93, 71.67, 44.30, 35.96, 19.32, 14.06, 10.56. ESI-MS (1c−H) C7H13O3−Mw=145.18, Observed=145.1.

3-Hydroxy-2,4-dimethylhexanoic acid (1d)

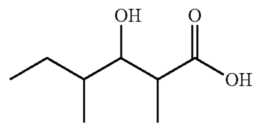

Brown oil, mixture of diastereomers; 1H NMR (400 MHz, CDCl3) δ 3.73 (dd, 1H), 2.71 (dq, 1H), 1.76 (m, 1H), 1.48 (m, 1H), [1.26 (d), 1.22 (d), 1.18 (d); 1:6:24 (3H)], 1.18 (m, 1H), [0.96 (d), 0.84 (d); 1:4 (3H)], 0.90 (t, 3H). 13C NMR (100 MHz, CDCl3) 6 [182.09, 191.73; 4:1], 75.32, [42.30, 41.66; 1:4], [37.12, 37.00; 1:4], [25.96, 25.02; 1:4], [15.04, 14.20; 4:1], [11.22, 11.00; 1:4], 9.35. ESI-MS (1d−H) C8H15O3−Mw=159.21, Observed=159.2.

3-Hydroxy-2,5-dimethylhexanoic acid (1e)

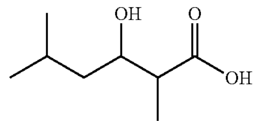

Tan/white solid, mixture of diastereomeres; 1H NMR (400 MHz, CDCl3) δ 4.05 (ddd, 1H), 2.59 (qd, 1H), 1.78 (m, 1H), 1.48 (m, 1H), 1.21 (d, 3H), 1.19 (m, 1H), [0.95 (d), 0.93 (d); 1:1, 6H]. 13C NMR (150 MHz, CDCl3) δ 179.43, 70.03, 44.46, 42.76, 24.83, 23.57, 22.00, 10.72. ESI-MS (1e−H) C8H15O3−Mw=159.21, Observed=159.2.

3-Hydroxy-2,4,4-trimethylpentanoic acid (1f)

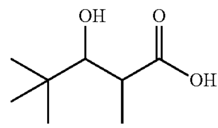

White solid, mixture of diastereomers; 1H NMR (400 MHz, CDCl3) δ 3.68 (d, 1H), 2.75 (qd, 1H), [1.38 (d), 1.25 (d); 5:3 (3H)], [0.96 (s), 0.94 (s); 3:2 (9H)]. 13C NMR (150 MHz, CDCl3) δ 180.35, [82.76, 78.27; 18:5], 39.28, [36.14; 35.86; 18:5], [26.76, 26.26; 18:5], [18.52, 12.41; 18:5]. ESI-MS (1f−H) C8H15O3−Mw=159.21, Observed=159.2.

Substrate Synthesis

2-Methylbutyryl-CoA (2a)

Following a previously reported procedure (Wu, N., Tsuji, S. Y., Cane, D. E., and Khosla, C. (2001) *J Am Chem Soc* 123, 6465-6474), 2-methylbutyryc acid (1 equiv, 26 μmol), CoA (lithium salt, 1.1 equiv, 29 μmol), and PyBOP (1.5 equiv, 39 μmol) were dissolved in a solution of THF (0.39 mL) and 4% K2CO3 (0.39 mL) and stirred under N2 for 40 min. The reaction mixture was diluted by addition of 2 mL water and injected onto ZORBAX SB-C18 column (50 mm length, 9.4 mm internal diameter, 5 μM particle size). The mobile phase was composed of 50 mM NaH2PO4 (pH=4.2) in water (solvent A) and methanol (solvent B). The acyl-CoA product was separated using the following gradient: 2.5% to 31% B for 12 min, 31% to 95% B for 1 min, held at 95% B for 2 min, 95% to 2.5% B for 2 min, held at 2.5% B for 2 min. A flow rate of 5 mL/min was used throughout. After removal of methanol, the eluted product was lyophilized and desalted by reinjection onto the same column. For desalting, the mobile phase was composed of water (solvent A) and methanol (solvent B). The product was separated using the following gradient: 2.5% to 31% B for 12 min, 31% to 95% B for 1 min, held at 95% B for 2 min, 95% to 2.5% B for 2 min, held at 2.5% B for 2 min. Lyophilization of the eluted product facilitated isolation of a white solid, 2a (6.5 μmol, 25% yield). 1H NMR (600 MHz, D2O) δ 8.66 (s, 1H), 8.39 (s, 1H), 6.27 (d, 1H), 4.94 (m, 2H), 4.68 (t, 1H), 4.2 (t, 2H), 4.11 (s, 1H), 3.92 (dd, 1H), 3.65 (dd, 1H), 3.53 (t, 2H), 3.41 (t, 2H), 3.07 (t, 2H), 2.71 (h, 1H), 2.51 (t, 2H), 1.68 (m, 1H), 1.53 (m, 1H), 1.18 (d, 3H), 0.98 (s, 3H), 0.92 (t, 3H), 0.86 (s, 3H). ESI-MS (2a+H) C26H45N7O17P3S+Mw=852.17, Observed=852.2.

Pivaloyl-CoA (2b)

Pivalic acid (1 equiv, 26 μmol) was used instead of 2-methylbutyryc acid in the experimental procedure described above to obtain a white solid, 2b (10.0 μmol, 38% yield). 1H NMR (600 MHz, D2O) δ 8.75 (s, 1H), 8.50 (s, 1H), 6.30 (d, 1H), 4.96 (m, 2H), 4.69 (t, 1H), 4.34 (t, 1H), 4,13 (s, 1H), 3.95 (dd, 1H), 3.68 (dd, 1H), 3.55 (t, 2H), 3.42 (t, 2H), 3.06 (t, 2H), 2.52 (t, 2H), 1.28 (s, 9H), 1.02 (s, 3H), 0.89 (s, 3H). ESI-MS (2b+H) C26H45N7O17P3S+ Mw=852.17, Observed=852.2.

Synthetic Gene

The gene encoding *Streptomyces aureofaciens* Tü117 LipPks1+*Saccharopolyspoera erythraea* 6-deoxyerythronolide B synthase thioesterase domain (LipPks1+TE) with codons optimized for expression in *Escherichia coli* was ordered from DNA2.0.

A codon-optimized gene sequence of His-LipPks1+TE is as follows:

(SEQ ID NO: 11)

```
ATGGGCAGCAGCCACCACCACCACCACCACAGCAGCGGCCTGGTCCCGCG
TGGTTCCCACATGGCAGGTCCACCGCCGTTCCCGCGTCGTCGTGGCCCGA
GCGGCCGTCGTCGTTGCGGCGGTCGTGCTACCCCGGGTAGCGTCCGTGAC
CGTACGGGTCGTCGTCCGGCAGCCGTTCCGAGCCGTGCAGTTTGCGCAGC
GGATCTGTGCGAAGAAAATGACGACGGCTCGAAGAATGTTTCTGAACATC
GCGGTAGCGCAGGTGGTTCCGTGCTGTTTCCACGTACCGGCACCGTCCTG
CCGTGGGTACTGACCGGTCCTGGCGCAGCGGCGGTTCGCGCACGCTCCGA
AGCACTGCGCACGCACCTGCGTGCGAGCACCGAGTGGTCCCCTGCGGGCG
TCGGTCAGGCGCTGCTGGCCGGTACGGGTGCGGGTGCCGATACCCACCGT
GCCGTTGTTCTGGCAGGCGACCGTGCCCAGACCCTGAACGCATTGGCAGC
GCTGAGCGCAGGCGCAGACCACCCGGCAGTTTTCACCAGCACTCGTGCGG
ATGCAAGCCCGGCTGGCCCGGTGTTTGTGTTCCCGGGTCAAGGCTCGCAG
TGGACCGGTATGGCTCGTGAACTGCTGGACTCCGCACCGGTTTTCGCGCG
TAAGCTGCACGACTGTGCAGACGCGTTTGCCCCGTACCTGGGCCACAGCC
TGCTGGATAGCGTCACCGGTGCAGCAGGTGGTCCAGAGCCTGTTGGCGCG
GACGTCGTCCAACCGGCGCTGTTCGCCGTTATGGTTGCGCTGACTGATCT
GTGGAACGCGGCTGGCGTTGCACCGGGTGCACTGCTGGGTCACTCCCTGG
GTGAACTGGCAGCCGCGCATGTCGCGGGTGTTCTGTCCCTGGACGATTCT
GCTCGCGTCGTGGCGCGTTGGAGCCAAGCGCAGGCTACGTTGGCGGGTCG
TGGTGACATGGTCAGCGTTCTGTTGCCTGCGGATGAATTGGCGGACCTGC
TGGACCGCCGTTGGCCGGGTCGCTTGGTTGTGGCGGTTGAAAACGGTCCA
GGTAGCGCGGTCGCGAGCGGTGACCTGGACGCTGCGGCGGAACTGGTCGC
```

-continued

```
ACACCTGACCGCCGAAGGTATCCACGCGCGTCGCGTTGACGTGGGCCTGG
CGGCTCACAGCCCGCACATTGACGCGATCCTGCCACGTATTCGCGCGGAC
ATCGCGCCGATTCGTGCGCATACGCCGAGCATCCCGGTTTATTCGGCGCT
GCATGGTGGTGCACTGGATGGCACGCCAATGGACGCGGCGTACTGGTGTC
GTAATCTGCGCTCCACTGTACGTTTCGCGGACGCGACCCGTGCAGCCCTG
GAGGCAGGCCATACCACGTTTGTGGAGGTAAGCCCACATCCGGTCCTGAC
TACGGCGATGGAGGTGAGCGCAACCCGTGCCGCGCACGCAGCAACTGTCC
TGGGTACGCTGCGCCGTGGTGAGGGTGGTCCGAGCCGCTTCCTGGCGAGC
CTGGCCGAACTGCATGTCAGCGGTGGTGATGCCGATCTGCGTACGGTTCT
GCCGGCTAGCCAGGCGGCTGGCTTGCCGGAAACCGTTCTGACGGCGGGTC
CGCGTGGCGAGAGCGCGGATGGCGACTCTCGTCATGAGGTTCTGTGCGCA
CGCCTGGCACCGCTGGACCCAGCGGAGCGTCGTGCCCAGCTGCTGACTGT
TGTTCGTGAAAGCGCAGCTGCCGCGCTGGACGGCGACGATCAAGGTAGCA
TTGACGGTCGTCGCACGTTCCGTGACCTGGGTATCACGTCGCTGGCAGCG
GTGGGCATCCGTGATCGCCTGCATTCCGCAACCGGTCTGCGTCTGTCTCC
GACCGTTGTGTTTGATCATCCGACCCCGGACGCACTGGCGGCACACTTGG
ACACCGAACTGTTCGGCACGGGCGCAGATGCCGAGCCGGCACCAGCTGCG
GGTGGTCGTGCGGTGCCGCATGACGAACCAATTGCGATCGTGGGTATGGC
GTGCCGTTACCCTGGCGGCGTTGGTGCACCGGCCGACCTGTGGCGTACCG
TTCTGGCCGGTGTCGACGCAGTTGGTCCGCTGCCGGCTGATCGTGGCTGG
AATATTGCGGACGGTTACGATCCGGAGCTGGCGGGTCCTGGTCGTTTTAG
CCAGCGTGAGGGCGGCTTTCTGCACGACGCAGCTGAATTTGATGCGGAGT
TCTTTGGTATTAGCCCGCGTGAGGCATTGGCGATGGACCCGCAGCAACGT
TTGGCTCTGGAAAGCGCCTGGGAAGCGATTGAGGATGCGGGTCTGGACGC
CCATAGCCTGCGTGGCAGCCGTACTGGCGTTTTTCTGGGCTTGATTACCC
AGGATTATGGTCCTCGTGCGGGTGAGCCGACCACGCGTGCAGGTGCGGTG
GAGGGTCACCTGTTCCTGGGTAGCACTGGCAGCGTCGCAAGCGGTCGTCT
GAGCTATACCTTGGGTCTGGAAGGTCCGTCTTTGACGATTGATACGGCAT
GTTCGAGCAGCCTGGTGGCACTGCACGAAGCATGTCAAGCGCTGCGTACC
GGTGATTGCGACATGGCTCTGACTGGTGGTGTGACGGTCATGCCGAGCAC
CGGCATGTTGGTCGAGTTCAGCCGTCAGCGTGGTCTGTCGCCTGACGGCC
GTTGTAAAGCCTTTTCTGCATCTGCCGACGGTTTTGGTCTGGCGGAAGGT
GTCGGTATGCTGGTGGTTGAGCGTCTGAGCGATGCGCGTCGTCTGGGCCA
TCGTGTGCTGGCGGTGGTGCGCGGTTCTGCGGTTAACCAAGATGGCGCGA
GCAATGGCCTGTCGGCGCCTAGCGGCCCAGCACAACAGCGCGTTATTCGC
CAGGCGCTGGTCAACGCTGGCGTCCAAGCATCCCAAGTGGACGTTGTCGA
AGCACATGGCACCGGTACGAAACTGGGCGATCCGATTGAGGCTCAAGCCC
TGCAAGCGACCTATGGCCAGGGCCGTCCGGCTGAGCGCCCGTTGTGGTTG
GGTTCTCTGAAGTCCAATATCGGCCACGCGCAAGCGGCAGCGGGTGTGGG
CGGTGTTATCAAAATGGTCATGGCGTTGCGTGAAGGCGTCCTGCCACCGA
CCCTGCACGCAGACGAGCCGAGCCCGCATATTGACTGGTCGGCGGGTCAG
```

-continued

GTTCGTCTGCTGACCGAGGAACGCGAGTGGCCGGAGGCAGGTCACCCTCG
CCGTGCGGCAGTTTCGAGCTTCGGTGTTAGCGGTACCAACGCACATGTGA
TTCTGGAAGCTGCACCGGGTACGGGTGGTGCGCCAGAAGTTTCGGACGGT
GTCCTGGGTAGCGCGCCTGAAACGGTCCCGTGGGTGCTGAGCGCTGCAAG
CCCTGACGCATTGCGTGCACAAGCAGAGCGTCTGCGCGGTCATGTGGCGG
AGCGTCCGGGTCTGGCTTCCGCCGATGTCGCGTTTGCGCTGGCGACCCGT
CGTACCGCGCTGGAATATCGCGCGGTGGCGGTTGGTGCGGAGCGCGACGA
GCTGCTGGATACCTTGGACGCGCTGAGCGCCGGTCGTCCGGCACCGCGTG
CTGTACCGGGTGACGCGGCTGCGCATAGCCGTCGTCCGGTTTTCGTCTTT
CCGGGTCAGGGTAGCCAGTGGGCAGGTATGGCGGTTGAACTGCTGGACAG
CAGCCCGGTTTTTGCGGACAGCATGCACGCATGTTCCGAGGCCCTGAATG
AATTTGTTGACTGGAACCTGCTGGAAGTTCTGCGTAGCGGTGACGAAGAG
CTGTCTAACCGTGTTGATGTCGTCCAACCGGTGCTGTGGGCAGTTATGGT
GAGCCTGGCAGCTCTGTGGCAAGCGTGTGGCGTCCGTCCTGCGGCGGTTG
TGGGTCACAGCCAAGGTGAGATTGCAGCTGCCGTTGTCGCAGGTGCACTG
AGCCTGCGTGATGGTGCCCGCGTTGTTGCATTGCGTAGCGCAGTGATCGC
GCGTCTGCTGGCAGGTAAGGGTGCGATGGCGAGCGTGGCTCTGGCGTCTG
ACACCGTTCGTGAGCGCCTGACCCCGTGGGAAGGTCGTCTGTCTCTGGCA
GCGGTCAATGGTCCGAGCAGCAGCGTTGTTTGCGGCCATCTGGATGCACT
GGACGAGTTCGTTAGCGCGTTGGAGCACGATGGCGTGCGTGTGCGTCGCA
TCGCGGTTGACTACGCAAGCCATAGCGTGTTCGTGGAGCAGGCAGAAGAA
GAGCTGCGTAATGTCCTGACCGAGGTGAGCCCTTTGCCGGGTCAAGTCCC
TTTCTACAGCACCGTGACCGGTGCGGTTCTGGATACCACGACTCTGGACG
CCGGCTACTGGTATCGTAACTTGCGTCAGACGGTTCGTTTCGAAGAAACC
GTGCGTGAGCTGACGCGCCGTGGCCACGACGCGTTCATCGAGGTGTCGGC
TCATCCGGTTCTGACCGTCGGCATTCAGGATACCTTGGAAGCCACCGGCA
CCCGCCATGCAGTCTGCGGTACGCTGCGTCGTGGTGAGGGCGGTGCGCAG
CGTTTGCTGACCAGCCTGGGTGAAGCGTGGGTTGCCGGCATTGCGGTGGA
CTGGAGCCGCTTGACGCCGACGACGACCGCTGTCCAACTGCCGACCTACG
CATTTCAGCATCAGCGTTACTGGCTGGATAGCACCACTGCAAACACTGGT
GACCGTCCGGCAGCGGACCGTGACACCGCATTTTGGGAAGCTGTGCAGCA
CACCGACCTGGACGCCTTCGCTGCAGAATTGGACATTGCCCCGGATGCGC
CGTTGGGCACCGTCTTGCCGGCTCTGGCTGACTGGCGTCAACGCCTGCGT
ACGGCAGCGGCTGTTGACGCATGGCGTTACCGCACCGCCTTTAAACGTCT
GCCAGATGCGCCAGGTGCACCAGTCCTGACGGGCAGCTGGCTGGCCGTAG
TTCCGGTGCGTCACCTGGATGATCCGAGCGTTACCACTAGCCTGGATGCA
GTTGCTAAAGCGGGTGCGGAAGTCGTTCAGTTGGCAATCGAAGATGCGGA
CGCGGACGTTGATCGTCTGACTGAGCGCTTGCGTGGCCTGGTTGCCGGTC
TGGGTGCCGCGCCGGCGGGCATTATGAGCTTCCTGGGTCTGGATGAAGAG
CGTCATCGTGACCACCCGGCGATGCCGAGCGGTCTGGCCACCAGCTTGGC

-continued

GCTGGTCCGCGCCTTGGGTCGTGCGGGCATCGGTGCACCGCTGTGGATGG
TTACGCGTGAGGCAGTGGCAGCGGGTCAAGACACGCACCCGCATGCGCCT
CTGGGTAGCCTGATCTGGGGTCTGGGCCAAGTGACGGCTCTGGAGCACGC
AGATCGCTGGGGTGGTCTGATCGATCTGCCGGGTGTGTGTGATGCGCGCG
TTGCCCGCATGCTGTGCGCGGGTCTGAGCGGCCGTGGTGCCGAAGATCAG
CTGGCCCTGCGTCCGAGCGGCACTTTCGTCCGCCGTCTGGCGCATATCCC
TGGCGAGCAACGTGCAGCACGTCGTAGCTGGCAACCACGTGGTACGGTGA
TTGTCACCGGTGGTACGGGTGCGCTGGGTGCAGTCCTGGCCCGCTGGTTG
GCTACCGAGGACGCGGAGCACCTGGTGCTGACCGGCCGTCGTGGCGCGGA
CGCCCCTGGCGCGGAGCGTTTGCGTGACGAGCTGGTCGCTACGGGCGCTC
GTGTCACGCTGGCGGCGTGCGACGTGGCAGATCGCAAAGCCGTCGCCGCA
TTGCTGGACGAACTGGCTGCGGACGGCGAGACTGTTCGCGCAGTTCTGCA
CGCTGCGGGTGTCGCCGATCTGACGTCGCTGGAGAATACCGGTCCAGAAG
CGTTCGCGGCAGGCGTGGCCGCGAAGGTCGATGGTGCACTGCACCTGACC
GAACTGTTGGATCACGATTCGCTGGATGCGTTTGTGTTGTTCAGCAGCAT
TGCGGGTGTTTGGGGTTCCGGCGACCACGGCGCGTATGCGGCTGCGAACG
CATTTCTGAATGCGTTGGCAGAGTACAATCGTGCACGCGGTATCCCGACC
ACGAGCATCGCATGGGGCGTTTGGAACGCGTTTGGCGTCGAGGGTGCAGG
CGGTATCAGCGAGGCGGTTGATTTGGACCAGCTGCATCGTCGCGGCCTGC
CGCTGATTGAACCAGAGCTGGGTCTGACTGCACTGCGTCGCGCTCTAGAC
CGTGACGAAACGGTGCTGACGGTTGCTCCGGTTGCCTGGGAGCGCTTCTT
TCCGCTGTTCTCCGCTGCACGTCCGCGTCCGTTGTTTGAGGACTTGCCGC
AAGTGCGTGCCCTGAGCGCACCTGTCCCGACGACGGCGGGTCCGGCCGTG
GAACCAGGTCGCCGTGGTAGCGGCCTGGGCGATTTGCCTCTGACGGATCG
CGATAGCGCGCTGCTGGCCTTGGTCCGCGGTGAGAGCGCATCCGTGCTGG
GTTACGAGCGTCCAGATCGCCTGGACCCGGACCGTGCGCTGCGTGATGTG
GGTTTCGATAGCCTGACGGCGATGGAACTGCGTAACCGTCTGGCTACCGC
GACCGGCCTGACGCTGCCTGCGGCCCTGGTGTTTGATCACCCGACCCCAC
TGGCGATCGCGGCGTATCTGAAAGCCGAGCTGACGAGCCAGCTGGACTCC
GGTACGCCTGCACGTGAAGCTAGCTCTGCACTGCGTGACGGCTACCGCCA
AGCGGGTGTGAGCGGCCGTGTTCGTAGCTACCTGGATCTGTTGGCAGGTC
TGTCGGATTTCCGCGAACATTTTGATGGTAGCGATGGTTTTAGCCTGGAT
CTGGTTGATATGGCAGATGGTCCGGGTGAGGTGACCGTTATTTGCTGCGC
GGGTACGGCTGCGATCTCTGGTCCGCATGAGTTCACCCGTCTGGCAGGTG
CCCTGCGCGGCATTGCACCTGTTCGTGCGGTGCCGCAGCCGGGTTACGAA
GAAGGCGAACCGCTGCCTTCTAGCATGGCGGCTGTTGCAGCTGTGCAGGC
TGATGCTGTCATTCGTACGCAAGGCGATAAGCCGTTCGTGGTTGCGGGTC
ACTCGGCAGGCGCGCTGATGGCGTACGCGCTGGCGACCGAACTGCTGGAT
CGTGGTCACCCGCCTCGCGGTGTTGTCCTGATTGATGTGTACCCGCCTGG
TCATCAGGACGCGATGAACGCGTGGCTGGAGGAACTGACGGCAACGTTGT
TCGACCGTGAAACTGTTCGTATGGACGACACCCGTCTGACCGCGTTGGGT

-continued

```
GCTTACGACCGCCTGACGGGTCAATGGCGTCCTCGCGAAACCGGTTTGCC

GACCCTGTTGGTTAGCGCGGGTGAACCAATGGGCCCGTGGCCGGACGATA

GCTGGAAACCGACCTGGCCTTTCGAGCACGACACCGTTGCGGTCCCGGGT

GATCATTTCACGATGGTTCAAGAACATGCTGATGCGATTGCCCGTCACAT

TGACGCCTGGCTGGGTGGCGGCAACAGCTGA
```

Plasmid Construction pSY044

The synthetic gene was designed to have a NdeI site and a BamHI site at the 5' and 3' ends, respectively. These restriction sites were used to subclone the gene into the NdeI and BamHI sites in pET30b to construct pSY044.

pSY066

A PCR amplified NdeI-HindIII fragment corresponding to the (−NL)lipPks1+TE gene, which encodes a N-terminally truncated version of the protein that begins with the amino acid sequence VFVFPGQG (SEQ ID NO:12), was ligated into NdeI-HindIII-digested pET28b to construct pSY066.

pSY065

A PCR amplified NdeI-EcoRI fragment corresponding to the lipPks1 gene, which encodes a Cterminally truncated version of the protein that ends with the amino acid sequence AYLKAEL (SEQ ID NO:13), was ligated into NdeI-EcoRI-digested pET28b to construct pSY065.

Protein Production and Purification

An *E. coli* K207-3 strain harboring pSY044 was grown in LB medium supplemented with appropriate antibiotics at 37° C. until the OD600 reached 0.4-0.5. The cultures were then cooled to 18° C. and induced with 250 μM isopropyl-β-D-galactopyranoside for 16 h. The cells were harvested by centrifugation (4000 g, 5 min) and resuspended in lysis/wash buffer (50 mM phosphate, pH 7.6, 300 mM NaCl, 10 mM imidazole, 4° C.). The cells were lysed by sonication (8 ×30 sec) and cellular debris was removed by two subsequent centrifugations (4000 g, 30 min, 4° C.). Nickel-NTA agarose resin (Qiagen) was added directly to the supernatant (1 mL of resin per L of culture) and mixed for 1 h at 4° C. The resulting mixture was poured into a fritted column, washed with 10 resin volumes of lysis/wash buffer (4° C.), and eluted with 2 resin volumes of elution buffer (150 mM phosphate, pH 7.6, 50 mM NaCl, 150 mM imidazole, 4° C.). The eluted protein was then applied to a HiTRAP Q anion exchange column (GE Healthcare), washed with 10 resin volumes of wash buffer (50 mM phosphate, pH 7.6, 200 mM NaCl, 8% Glycerol, 4° C.), and eluted at approximately 375 mM NaCl. The buffer was exchanged into stock buffer (50 mM phosphate, pH 7.6, 8% glycerol, 4° C.) by dialysis using an Amicon Ultra-15 Centrifugal Filter, 100K device (Millipore). The resulting purified protein was stored at −80° C.

Kinetic Analysis

Starter Substrates

A Bradford protein assay was used to measure the concentration of LipPks1+TE. The concentrations of solutions containing various acyl-CoA compounds (acetyl-CoA, propionyl-CoA, n-butyryl-CoA, isobutyryl-CoA, 2-methylbutyryl-CoA, isovaleryl-CoA, or pivaloyl-CoA) were determined using the absorbance at 260 nm and calibration against known CoA concentration standards. Each time point was set up in a reaction volume of 75 μL. Samples containing 20 μM, 40 μM, 80 μM, 160 μM, or 320 μM of acyl-CoA were individually incubated with 200 μM methymalonyl-CoA and 500 μM NADPH in the presence of 0.5 μM LipPks1+TE in 100 mM phosphate buffer, pH 7.2, containing 2.5 mM TCEP at 23° C. The reactions were quenched at different time points by adding 75 μL of methanol and subsequently filtered with an Amicon Ultra-0.5 mL Centrifugal Filter, 3K device (Millipore) at 23° C. 10 μL of the resulting solutions were analyzed by liquid chromatography-mass spectrometry (LC-MS). Authentic standards (1a, 1b, 1c, 1d, 1e, and 1f) were used to quantify the products in the LC-MS analysis. We assumed that ionization efficiencies of diastereomers were identical.

Extension Substrate

Each time point was set up in a reaction volume of 75 μL. Samples containing 10 μM, 20 μM, or 40 μM methylmalonyl-CoA were individually incubated with 500 μM isovaleryl-CoA and 500 μM NADPH in the presence of 0.5 μM LipPks1+TE in 100 mM phosphate buffer, pH 7.2, containing 2.5 mM TCEP at 23° C. The reactions were quenched at different time points by adding 75 μL of methanol and subsequently filtered with an Amicon Ultra-0.5 mL Centrifugal Filter, 3K device (Millipore) at 23° C. 10 μL of the resulting solutions were analyzed by LC-MS. Authentic standard 1e was used to quantify the products in the LC-MS analysis. We assumed that ionization efficiencies of diastereomers were identical.

LC Analysis

LC separation of the enzymatically generated products conducted at 50° C. with an Inertsil ODS-3 reverse-phase column (250 mm length, 2.1 mm internal diameter, 3 μM particle size; GL Sciences) using a 1100 series high-performance liquid chromatography system (Agilent Technologies). The mobile phase was composed of 0.2% formic acid in water (solvent A) and 0.2% formic acid in methanol (solvent B). Products were separated using the following gradient: 60% to 100% B for 10 min, held at 100% B for 2 mM, 100% to 60% B for 1 min, held at 60% B for 17 min. A flow rate of 0.14 mL/min was used throughout.

MS Analysis

The LC system was coupled to an Agilent Technologies LC-MSD SL electrospray ionization mass (ESI MS) spectrometer. Nitrogen gas was used as both the nebulizing and drying gas to facilitate the production of gas-phase ions. The drying and nebulizing gases were set to 10 L/min and 20 lb/in2, respectively, and a drying gas temperature of 300° C. was used throughout. ESI was conducted in the negative-ion mode with a capillary voltage of 4 kV. Mass measurements were carried out in the selected ion monitoring mode (1a, m/z 145; 1b, m/z 131; 1c, m/z 145; 1d, m/z 159; 1e, m/z 159; 1f, m/z 159) at 1.01 s/cycle with a dwell time of 1 s for the detection of [M-H]− ions. The instrument was tuned for a range of m/z 50 to 3000 via the Agilent ES tuning mix. Data acquisition and processing were performed by an Agilent Chemstation (Agilent Technologies; Santa Clara, Calif.).

TABLE 3

| Plasmids | | | |
|---|---|---|---|
| Plasmid | Gene | Parent Vector | Resistance |
| pSY044 | His-LipPks1 + TE | pET30b | Kanamycin |
| pSY066 | His-(-NL)LipPks1 + TE | pET28b | Kanamycin |
| pSY065 | His-LipPks1 | pET28b | Kanamycin |

EXAMPLE 2

Structurally Diverse Ketone Production by an Engineered Polyketide Synthase

Type I polyketide synthases (PKSs) are multi-subunit megaenzymes that carry out a programmed, step-wise process resulting in the generation of poly-β-ketones with varying degrees of reduction at the β-carbonyl centers. Here, we report engineered biosynthesis of structurally diverse β-keto-carboxylic acids by PKSs in vitro, which are then decarboxylated to produce the corresponding ketones. Short/branched-chain ketones such as methyl ethyl ketone (MEK) are industrially important solvents and are used in a variety of applications. We also report heterologous production of MEK in *Escherichia coli*. This technology could allow us to produce a variety of ketones in microbes from renewable carbon sources.

Type I polyketide synthases (PKSs) are multi-subunit megaenzymes that catalyze successive rounds of decarboxylative condensation in a fashion similar to fatty acid synthases (FASs). However, in contrast to FAS, each elongation step and subsequent processing of the newly generated β-carbonyl group is carried out in a separate subunit called a module. Diversity of modules not only can generate a huge diversity in the product structures but also offers a wealth of engineering opportunities[1].

Each module minimally consists of a ketosynthase (KS) domain, an acyltransferase (AT) domain, and an acyl carrier protein (ACP) domain that are together responsible for a single round of chain elongation reaction. Individual modules may also contain a specific subset of β-carbon-processing enzymes, including a ketoreductase (KR) domain, a dehydratase (DH) domain, and/or an enoylreductase (ER) domain. The extended polyketide chain is translocated to the KS of the next module for another round of condensation and β-carbon modification. The chain elongation reaction is initiated by a loading di-or tri-domain located at the N-terminus of the first module. Finally, the chain growth is terminated by a thioesterase (TE) domain located at the C-terminus of the last module which often gives a macrolactone.

Although TE-mediated macrocyclization is the best understood system and regarded as the canonical release mechanism for type I PKSs, several other types of chain release have been reported, including TE-mediated hydrolysis, and reductase domain catalyzed 2- or 4-electron reduction, which give a linear carboxylic acids, aldehydes or alcohols[2], respectively. However, to our knowledge, no natural PKS has been uncovered that releases its product as a ketone.

Two decades ago, ketone production was observed by McDaniel, Khosla, and co-workers where they introduced a PKS that was designed to produce a β-keto-carboxylic acid into *Streptomyces coelicolor*[3,4]. They assumed that formation of the ketone resulted from non-enzymatic decarboxylation of β-keto-carboxylic acid. To further interrogate ketone release mechanisms and to demonstrate the potential of PKS as a platform to synthesize a variety of ketone compounds, we engineered a single PKS to produce 10 different β-keto-carboxylic acids and biochemically analyzed the corresponding ketone produced in vitro (FIG. 15). We also report heterologous production of some of these ketones in *Escherichia coli*, which includes the industrially important methyl ethyl ketone (MEK).

Figure 16:
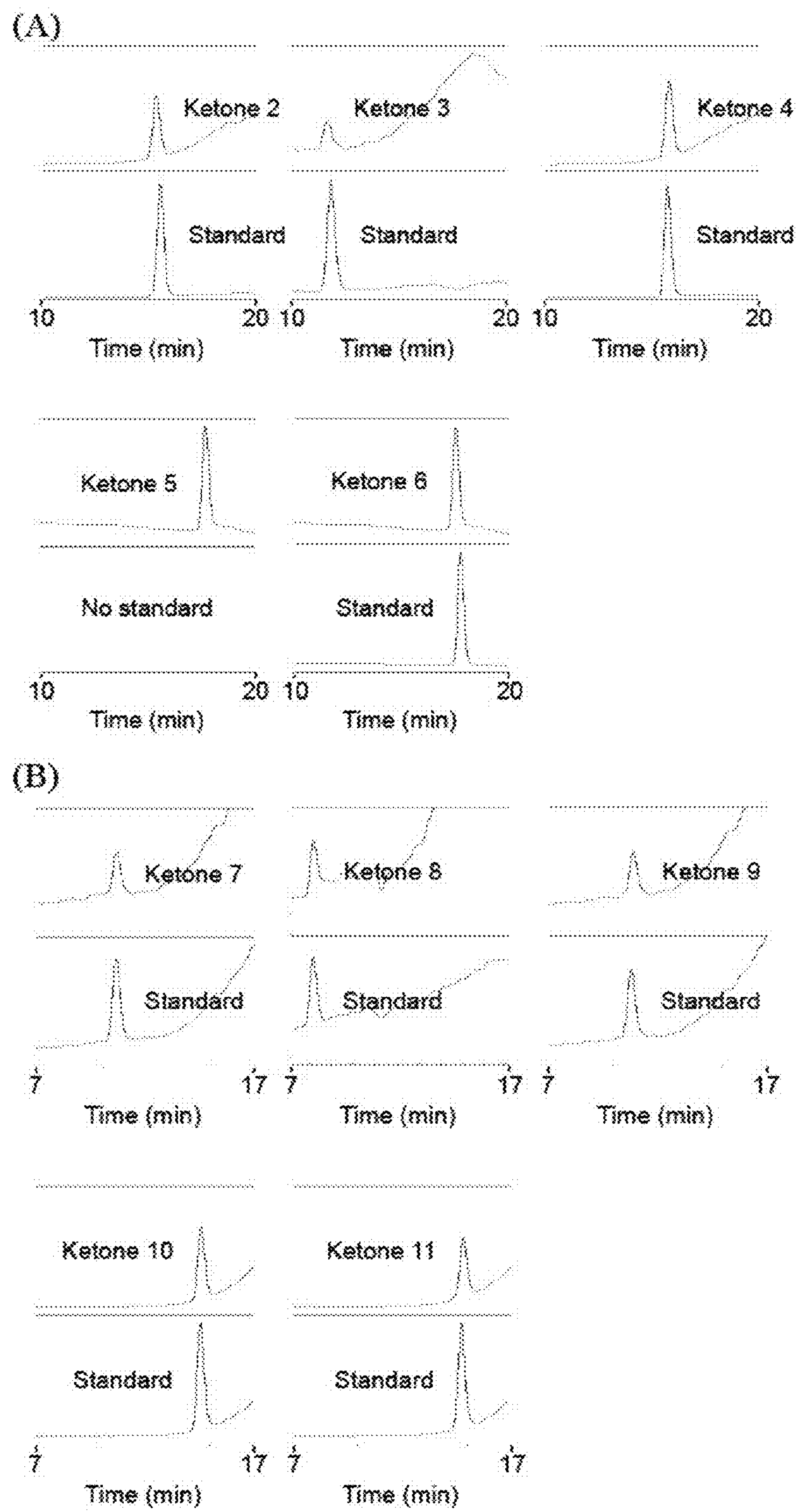
FIG. 16 shows LC-MS analysis of the in vitro production of 2-11. (A) Products 2-6: Propionyl-CoA, n-butyryl-CoA, isobutyryl-CoA, 2-methylbutyryl-CoA, or isovaleryl-CoA was incubated with methylmalonyl-CoA for 17 h at 23° C. in the presence of LipPks1+TE. (B) Products 7-11: Propionyl-CoA, n-butyryl-CoA, isobutyryl-CoA, 2-methylbutyryl-CoA, or isovaleryl-CoA was incubated with malonyl-CoA for 17 h at 23° C. in the presence of mutant 75. The resulting reaction mixtures were quenched and heated form ketones. The supernatants (top) and the corresponding authentic standards (bottom) were analyzed by LC-MS.

We recently showed that an engineered derivative of the lipomycin PKS produced a 3-hydroxy carboxylic acid in vitro in a multiple turnover fashion[5]. This PKS, LipPks1+TE, composed of a loading di-domain, a KS domain, an AT domain, a KR domain, an ACP domain, and the TE domain from 6-deoxyerythronolide B synthase (DEBS), catalyzes polyketide chain initiation, a single round of chain elongation, β-keto reduction with NADPH, and hydrolytic release of the product. To demonstrate the capability of producing β-keto-carboxylic acids, we simply removed NADPH from the in vitro reaction mixture and monitored production of 3-oxo-2,4-dimethylpentanoate (1) from isobutyryl-CoA and methylmalonyl-CoA by liquid chromatography and mass spectroscopy (LC-MS). The expected product 1 was not observed, however. We reasoned that spontaneous decarboxylation occurred during the reaction to give the corresponding ketone (2). MS measurement was then taken in the selected ion-monitoring mode for 2. Interestingly, we observed a strong peak but the elution time was not matched with the authentic ketone standard. When the reaction mixture was heated, the peak was gone and we observed a new peak, which was confirmed as the expected ketone product 2 (FIG. 16A). We also confirmed that the enzymatic reaction was catalyzed in a multiple turnover fashion and the production kinetics was basically the same as that of producing the 3-hydroxy carboxylic acid when NADPH was included in the incubation mixture. These data suggest that LipPks1+TE produces a β-keto-carboxylic acid in the absence of NADPH at 23° C. and that heating is necessary for decarboxylation. To study temperature dependence of decarboxylation of the β-keto-carboxylic acid, we incubated the reaction mixture at 23° C., 37° C., or 50° C. after quenching. Decarboxylation occurred even at 23° C. but with much lower efficiency than 37° C.

The loading di-domain of LipPks1 was shown previously to be substrate promiscuous and can process a wide variety of starter substrates with reasonable $k_{cat}/K_M$ values, including propionyl-CoA, n-butyryl-CoA, isobutyryl-CoA, 2-methylbutyryl-CoA, and isovaleryl-CoA[5]. Hence, we incubated these starters with methylmalonyl-CoA to produce ketones 3-6; each ketone was verified against the authentic standard (FIG. 16A), except for ketone 5, which was not purchased. Because this product showed the correct molecular weight and the elution time was basically the same as the one for ketone 6, an isomer of 5, we concluded that ketone 5 was also produced.

The modular nature of type I PKS presents an attractive framework for engineering to generate diverse compounds. AT domains act as gatekeepers to building block incorporation, which makes them the primary target of PKS engineering efforts[6]. The most common approach for altering AT substrate specificity is the swapping of an entire AT domain for a homologue with different specificity. However, AT-swapped constructs generally exhibit decreased product titers[7]. In the accompanying paper, we describe an improved method for AT domain swapping that results in constructs that maintain product titer. Using this method, we created mutant 75 where the lipAT1 domain was exchanged with the one from module 1 of the borrelidin PKS, which is specific to malonyl-CoA. This mutant maintained the wild-type kinetics to produce the corresponding methyl ketones, which includes the industrially important MEK (ketone 8) and methyl isobutyl ketone, MIBK (ketone 11) when the corresponding starter units, propionyl-CoA and isovaleryl-CoA, respectively, were added to the reaction mixtures in vitro (FIG. 16B).

Short/branched-chain ketones such as acetone, MEK, MIBK and di-isobutyl ketone are industrially important solvents and are used in a variety of applications, including in paints, coatings, adhesives, magnetic tapes, and inks, or for cleaning, and extraction. These ketones are currently derived from petroleum sources. Toward sustainable production, we sought to engineer LipPks1+TE and mutant 75 to produce short/branched-chain ketones from renewable carbon sources in *Escherichia coli*. Specifically, we mutated the active site serine residues of KR domain (LFSS̲IAG, SEQ ID NO:7) of both LipPks1+TE and mutant 75 to alanine residues to produce ketones even in the presence of NADPH. These engineered PKSs were designated as mutant 87 and 88, respectively. The mutant proteins were purified and we confirmed that they were able to produce ketones in vitro in the presence of NAPDH, employed at concentrations equivalent to its intracellular level in *E. coli*[8].

*E. coli* K207-3 is an engineered strain whose genome encodes propionyl-CoA carboxylase from *Streptomyces coelicolor* that converts propionyl-CoA to methylmalonyl-CoA[9]. This strain can also convert exogenously fed propionate into propionyl-CoA by overexpressing the native propionyl-CoA ligase[10]. In addition, the genome encodes the substrate promiscuous phosphopantetheinyl transferase Sfp from *Bacillus subtilis* that converts the expressed apo-PKSs to their corresponding holo forms[11].

Figure 17:
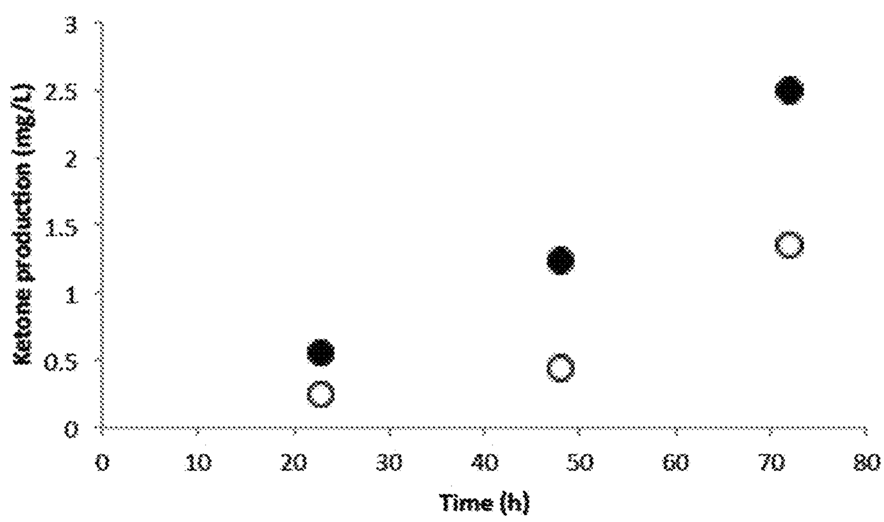
FIG. 17 shows LC-MS analysis of the in vivo production of 3 and MEK. Closed circles: Production of 3 by overexpressing mutant 87 in *E. coli* K207-3 in the presence of propionate. Open circles: Production of MEK by overexpressing mutant 88 in *E. coli* K207-3 in the presence of propionate. The resulting cultures were quenched and heated to form ketones. The supernatants were analyzed by LC-MS.

We transformed *E. coli* K207-3 with a plasmid encoding PKS mutant 87 or mutant 88 and cultured the two strains at 18° C. for three days in the presence of propionate. LC-MS analysis of the culture supernatants revealed the presence of the expected ketone products 3 and 8 (MEK), respectively (FIG. 17).

In summary, we have designed a number of PKSs to produce 10 different β-keto-carboxylic acids to investigate ketone production mechanisms and exploit the knowledge gained to produce short/branched-chain ketones in *E. coli* cultures. In vitro kinetic analysis of the engineered PKSs indicated that the KS domain of LipPks1 can process both malonyl-ACP and methylmalonyl-ACP with similar efficiency, and that the thioesterase domain of DEBS can hydrolyze β-keto-α-desmethylacyl-ACP, which is not the native substrate both for the α and β positions, without affecting the overall kinetics. For the AT swapping experiments, we used the improved methodology we recently developed. This method would also allow us to design PKSs that use other substrates such as ethylmalonyl-CoA and allylmalonyl-CoA to produce novel ketones in an efficient manner. In vitro ketone production analysis suggests that decarboxylation of β-keto-carboxylic acids is spontaneous but the reaction is very slow at temperatures where *E. coli* can produce functional type I PKSs (18° C.-22° C.)[10]. In fact, heating was required to detect ketones from *E. coli* cultures overexpressing engineered PKSs at 18° C. However, additional experiments are required to exactly measure the amount of MEK produced because the boiling point is lower than that of water and more than 75% of MEK actually evaporated during the culture in a control experiment (data not shown).

The present study shows the first rationally designed pathways to produce short/branched-chain ketones such as MEK and MIBK in microbes. Importantly, this PKS-based technology can be extended to produce longer ketones by introducing additional modules. We previously developed a pathway to produce propionyl-CoA from renewable carbon sources such as sugars [12]. Together with branched-chain keto acid dyhydrogenase from *Bacillus subtilis* or *Streptomyces avermitilis* that can produce isobutyryl-CoA, 2-methylbutyryl-CoA, and isovaleryl-CoA from the corresponding amino acids, we might be able to produce the full spectrum of ketones described here from renewable carbon sources.

REFERENCES CITE IN EXAMPLE 2

(1) Khosla, C.; Tang, Y.; Chen, A. Y.; Schnarr, N. A.; Cane, D. E. *Annual review of biochemistry* 2007, 76, 195.

(2) Du, L.; Lou, L. *Natural product reports* 2010, 27, 255.

(3) McDaniel, R. e. a. *J Am Chem Soc* 1997.

(4) Kao, C. M.; McPherson, M.; McDaniel, R. N.; Fu, H.; Cane, D. E.; Khosla, C. *J Am Chem Soc* 1997, 119, 11339.

(5) Yuzawa, S.; Eng, C. H.; Katz, L.; Keasling, J. D. *Biochemistry* 2013, 52, 3791.

(6) Dunn, B. J.; Khosla, C. *J R Soc Interface* 2013, 10.

(7) Hans, M.; Hornung, A.; Dziarnowski, A.; Cane, D. E.; Khosla, C. *J Am Chem Soc* 2003, 125, 5366.

(8) Bennett, B. D.; Kimball, E. H.; Gao, M.; Osterhout, R.; Van Dien, S. J.; Rabinowitz, J. D. *Nat Chem Biol* 2009, 5, 593.

(9) Murli, S.; Kennedy, J.; Dayem, L. C.; Carney, J. R.; Kealey, J. T. *Journal of industrial microbiology & biotechnology* 2003, 30, 500.

(10) Pfeifer, B. A.; Admiraal, S. J.; Gramajo, H.; Cane, D. E.; Khosla, C. *Science* 2001, 291, 1790.

(11) Lambalot, R. H.; Gehring, A. M.; Flugel, R. S.; Zuber, P.; LaCelle, M.; Marahiel, M. A.; Reid, R.; Khosla, C.; Walsh, C. T. *Chemistry & biology* 1996, 3, 923.

(12) Yuzawa, S.; Chiba, N.; Katz, L.; Keasling, J. D. *Biochemistry* 2012, 51, 9779.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What we claim is:

1. A hybrid polyketide synthase (PKS) comprising modules, domains, and/or portions thereof from two or more PKSs capable of synthesizing a 3-hydroxycarboxylic acid or ketone; wherein the PKS comprises a loading acyltransferase ($AT_L$) domain and a loading ACP ($ACP_L$) domain, both of LipPks1 of a lipomycin synthase of *Streptomyces* aureofaciens Tü117, a ketosynthase (KS) domain, an acyltransferase (AT) domain, a ketoreductase (KR) domain, an ACP domain of LipPks1 of a lipomycin synthase of *Streptomyces* aureofaciens Tü117, and a thioesterase (TE) domain appended to the C-terminus of the ACP domain of LipPks1; wherein the hybrid PKS has a broad substrate specificity; the 3-hydroxycarboxylic acid has the following chemical structure:

(I)

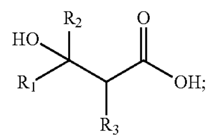

wherein $R_1$ is —H, $R_2$ is —H, $—CH_3$, $—CH_2CH_3$, $—CH_2CH_2CH_3$, $—CH(CH_3)_2$, $—CH(CH_3)CH_2CH_3$, $—CH_2CH(CH_3)_2$, $—C_6H_{11}$, or $—C_6H_5$, and $R_3$ is —H, $—CH_3$, $—CH_2CH_3$, $—CH_2CH_2Cl$, $—CH_2CH{=}CH_2$, or $—CH_2CH_2COCH_3$; and, the ketone has the following chemical structure:

(II)

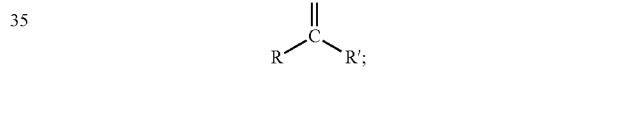

wherein R is $—CH_3$, $—CH_2CH_3$, $—CH_2CH_2CH_3$, $—CH(CH_3)_2$, $—CH(CH_3)CH_2CH_3$, $—CH_2CH(CH_3)_2$, $—C_6H_{11}$, or $—C_6H_5$, and R' is $—CH_3$, $—CH_2CH_3$, $—CH_2CH_2Cl$, $—CH_2CH{=}CH_2$, or $—CH_2CH_2COCH_3$.

2. The hybrid PKS of claim 1, wherein the hybrid PKS is capable of synthesizing the 3-hydroxycarboxylic acid.

3. The hybrid PKS of claim 2, wherein the hybrid PKS is capable of synthesizing:

1a

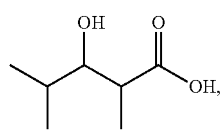

1b

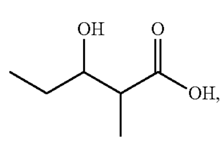

1c

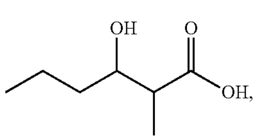

-continued 1d, 1e, 1f

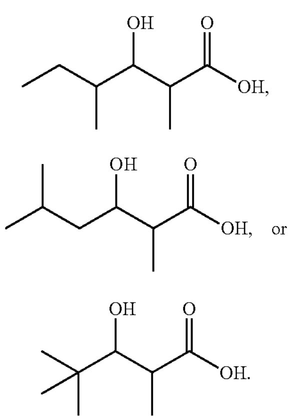

4. The hybrid PKS of claim 1, wherein the hybrid PKS is capable of synthesizing the ketone.

5. The hybrid PKS of claim 4, wherein the hybrid PKS is capable of synthesizing:

2, 3

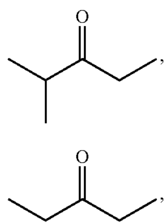

-continued 4, 5, 6

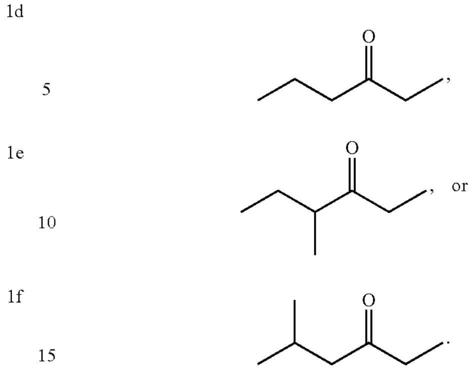

6. A recombinant nucleic acid encoding the polyketide synthase (PKS) of claim 1.

7. A replicon comprising the recombinant nucleic acid 6, wherein the replicon is capable of stable maintenance in a host cell.

8. The replicon of claim 7, wherein the replicon is a plasmid or vector.

9. The replicon of claim 8, wherein the vector is an expression vector.

10. A host cell comprising the replicon of claim 7.

11. A host cell comprising the recombinant nucleic acid of claim 6.

12. The host cell of claim 11, wherein the host cell when cultured produces the 3-hydroxycarboxylic acid or ketone.

* * * * *

SEQUENCE LISTING

<160> NUMBER OF SEQ ID NOS: 13

<210> SEQ ID NO 1
<211> LENGTH: 19
<212> TYPE: PRT
<213> ORGANISM: Streptomyces nodosus

<400> SEQUENCE: 1

Ser Ser Thr Ala Gly Met Trp Gly Ser Gly Val His Ala Ala Tyr Val
1 5 10 15

Ala Gly Asn

<210> SEQ ID NO 2

<211> LENGTH: 19
<212> TYPE: PRT
<213> ORGANISM: Streptomyces noursei

<400> SEQUENCE: 2

```
Ser Ser Thr Ala Gly Met Trp Gly Ser Gly Val His Ala Ala Tyr Val
1               5                   10                  15

Ala Gly Asn
```

<210> SEQ ID NO 3
<211> LENGTH: 19
<212> TYPE: PRT
<213> ORGANISM: Streptomyces nodosus

<400> SEQUENCE: 3

```
Ser Ser Thr Ala Gly Met Trp Gly Ser Gly Ala His Ala Ala Tyr Val
1               5                   10                  15

Ala Gly Asn
```

<210> SEQ ID NO 4
<211> LENGTH: 19
<212> TYPE: PRT
<213> ORGANISM: Streptomyces aureofaciens

<400> SEQUENCE: 4

```
Ser Ser Ile Ala Gly Val Trp Gly Ser Gly Asp His Gly Ala Tyr Ala
1               5                   10                  15

Ala Ala Asn
```

<210> SEQ ID NO 5
<211> LENGTH: 452
<212> TYPE: PRT
<213> ORGANISM: Streptomyces aureofaciens

<400> SEQUENCE: 5

```
Gly Thr Asn Ala His Val Ile Leu Glu Ala Ala Pro Gly Thr Gly Gly
1               5                   10                  15

Ala Pro Glu Val Ser Asp Gly Val Leu Gly Ser Ala Pro Glu Thr Val
            20                  25                  30

Pro Trp Val Leu Ser Ala Ala Ser Pro Asp Ala Leu Arg Ala Gln Ala
        35                  40                  45

Glu Arg Leu Arg Gly His Val Ala Glu Arg Pro Gly Leu Ala Ser Ala
    50                  55                  60

Asp Val Ala Phe Ala Leu Ala Thr Arg Arg Thr Ala Leu Glu Tyr Arg
65                  70                  75                  80

Ala Val Ala Val Gly Ala Glu Arg Asp Glu Leu Leu Asp Thr Leu Asp
                85                  90                  95

Ala Leu Ser Ala Gly Arg Pro Ala Pro Arg Ala Val Pro Gly Asp Ala
            100                 105                 110

Ala Ala His Ser Arg Arg Pro Val Phe Val Phe Pro Gly Gln Gly Ser
        115                 120                 125

Gln Trp Ala Gly Met Ala Val Glu Leu Leu Asp Ser Ser Pro Val Phe
    130                 135                 140

Ala Asp Ser Met His Ala Cys Ser Glu Ala Leu Asn Glu Phe Val Asp
145                 150                 155                 160

Trp Asn Leu Leu Glu Val Leu Arg Ser Gly Asp Glu Glu Leu Ser Asn
                165                 170                 175

Arg Val Asp Val Val Gln Pro Val Leu Trp Ala Val Met Val Ser Leu
```

```
            180                 185                 190

Ala Ala Leu Trp Gln Ala Cys Gly Val Arg Pro Ala Ala Val Val Gly
        195                 200                 205

His Ser Gln Gly Glu Ile Ala Ala Ala Val Val Ala Gly Ala Leu Ser
    210                 215                 220

Leu Arg Asp Gly Ala Arg Val Val Ala Leu Arg Ser Ala Val Ile Ala
225                 230                 235                 240

Arg Leu Leu Ala Gly Lys Gly Ala Met Ala Ser Val Ala Leu Ala Ser
                245                 250                 255

Asp Thr Val Arg Glu Arg Leu Thr Pro Trp Glu Gly Arg Leu Ser Leu
            260                 265                 270

Ala Ala Val Asn Gly Pro Ser Ser Ser Val Val Cys Gly His Leu Asp
        275                 280                 285

Ala Leu Asp Glu Phe Val Ser Ala Leu Glu His Asp Gly Val Arg Val
    290                 295                 300

Arg Arg Ile Ala Val Asp Tyr Ala Ser His Ser Val Phe Val Glu Gln
305                 310                 315                 320

Ala Glu Glu Glu Leu Arg Asn Val Leu Thr Glu Val Ser Pro Leu Pro
                325                 330                 335

Gly Gln Val Pro Phe Tyr Ser Thr Val Thr Gly Ala Val Leu Asp Thr
            340                 345                 350

Thr Thr Leu Asp Ala Gly Tyr Trp Tyr Arg Asn Leu Arg Gln Thr Val
        355                 360                 365

Arg Phe Glu Glu Thr Val Arg Glu Leu Thr Arg Arg Gly His Asp Ala
    370                 375                 380

Phe Ile Glu Val Ser Ala His Pro Val Leu Thr Val Gly Ile Gln Asp
385                 390                 395                 400

Thr Leu Glu Ala Thr Gly Thr Arg His Ala Val Cys Gly Thr Leu Arg
                405                 410                 415

Arg Gly Glu Gly Gly Ala Gln Arg Leu Leu Thr Ser Leu Gly Glu Ala
            420                 425                 430

Trp Val Ala Gly Ile Ala Val Asp Trp Ser Arg Leu Thr Pro Thr Thr
        435                 440                 445

Thr Ala Val Gln
    450


<210> SEQ ID NO 6
<211> LENGTH: 7
<212> TYPE: PRT
<213> ORGANISM: Streptomyces parvulus

<400> SEQUENCE: 6

Pro Arg Ala Arg Thr Val Asp
1               5


<210> SEQ ID NO 7
<211> LENGTH: 7
<212> TYPE: PRT
<213> ORGANISM: Streptomyces aureofaciens

<400> SEQUENCE: 7

Leu Phe Ser Ser Ile Ala Gly
1               5


<210> SEQ ID NO 8
<211> LENGTH: 7
<212> TYPE: PRT
```

```
<213> ORGANISM: Streptomyces aureofaciens

<400> SEQUENCE: 8

Leu Phe Ser Ala Ile Ala Gly
1               5


<210> SEQ ID NO 9
<211> LENGTH: 7
<212> TYPE: PRT
<213> ORGANISM: Streptomyces aureofaciens

<400> SEQUENCE: 9

Leu Phe Ser Ala Ile Ala Gly
1               5


<210> SEQ ID NO 10
<211> LENGTH: 2259
<212> TYPE: PRT
<213> ORGANISM: Streptomyces aureofaciens

<400> SEQUENCE: 10

Met Ala Gly Pro Pro Pro Phe Pro Arg Arg Arg Gly Pro Ser Gly Arg
1               5                   10                  15

Arg Arg Cys Gly Gly Arg Ala Thr Pro Gly Ser Val Arg Asp Arg Thr
            20                  25                  30

Gly Arg Arg Pro Ala Ala Val Pro Ser Arg Ala Val Cys Ala Ala Asp
        35                  40                  45

Leu Cys Glu Glu Asn Asp Asp Gly Ser Lys Asn Val Ser Glu His Arg
    50                  55                  60

Gly Ser Ala Gly Gly Ser Val Leu Phe Pro Arg Thr Gly Thr Val Leu
65                  70                  75                  80

Pro Trp Val Leu Thr Gly Pro Gly Ala Ala Ala Val Arg Ala Arg Ser
                85                  90                  95

Glu Ala Leu Arg Thr His Leu Arg Ala Ser Thr Glu Trp Ser Pro Ala
            100                 105                 110

Gly Val Gly Gln Ala Leu Leu Ala Gly Thr Gly Ala Gly Ala Asp Thr
        115                 120                 125

His Arg Ala Val Val Leu Ala Gly Asp Arg Ala Gln Thr Leu Asn Ala
    130                 135                 140

Leu Ala Ala Leu Ser Ala Gly Ala Asp His Pro Ala Val Phe Thr Ser
145                 150                 155                 160

Thr Arg Ala Asp Ala Ser Pro Ala Gly Pro Val Phe Val Phe Pro Gly
                165                 170                 175

Gln Gly Ser Gln Trp Thr Gly Met Ala Arg Glu Leu Leu Asp Ser Ala
            180                 185                 190

Pro Val Phe Ala Arg Lys Leu His Asp Cys Ala Asp Ala Phe Ala Pro
        195                 200                 205

Tyr Leu Gly His Ser Leu Leu Asp Ser Val Thr Gly Ala Ala Gly Gly
    210                 215                 220

Pro Glu Pro Val Gly Ala Asp Val Val Gln Pro Ala Leu Phe Ala Val
225                 230                 235                 240

Met Val Ala Leu Thr Asp Leu Trp Asn Ala Ala Gly Val Ala Pro Gly
                245                 250                 255

Ala Leu Leu Gly His Ser Leu Gly Glu Leu Ala Ala Ala His Val Ala
            260                 265                 270

Gly Val Leu Ser Leu Asp Asp Ser Ala Arg Val Val Ala Arg Trp Ser
        275                 280                 285
```

-continued

```
Gln Ala Gln Ala Thr Leu Ala Gly Arg Gly Asp Met Val Ser Val Leu
    290                 295                 300

Leu Pro Ala Asp Glu Leu Ala Asp Leu Leu Asp Arg Arg Trp Pro Gly
305                 310                 315                 320

Arg Leu Val Val Ala Val Glu Asn Gly Pro Gly Ser Ala Val Ala Ser
                325                 330                 335

Gly Asp Leu Asp Ala Ala Ala Glu Leu Val Ala His Leu Thr Ala Glu
            340                 345                 350

Gly Ile His Ala Arg Arg Val Asp Val Gly Leu Ala Ala His Ser Pro
        355                 360                 365

His Ile Asp Ala Ile Leu Pro Arg Ile Arg Ala Asp Ile Ala Pro Ile
    370                 375                 380

Arg Ala His Thr Pro Ser Ile Pro Val Tyr Ser Ala Leu His Gly Gly
385                 390                 395                 400

Ala Leu Asp Gly Thr Pro Met Asp Ala Ala Tyr Trp Cys Arg Asn Leu
                405                 410                 415

Arg Ser Thr Val Arg Phe Ala Asp Ala Thr Arg Ala Ala Leu Glu Ala
            420                 425                 430

Gly His Thr Thr Phe Val Glu Val Ser Pro His Pro Val Leu Thr Thr
        435                 440                 445

Ala Met Glu Val Ser Ala Thr Arg Ala Ala His Ala Ala Thr Val Leu
    450                 455                 460

Gly Thr Leu Arg Arg Gly Glu Gly Gly Pro Ser Arg Phe Leu Ala Ser
465                 470                 475                 480

Leu Ala Glu Leu His Val Ser Gly Gly Asp Ala Asp Leu Arg Thr Val
                485                 490                 495

Leu Pro Ala Ser Gln Ala Ala Gly Leu Pro Glu Thr Val Leu Thr Ala
            500                 505                 510

Gly Pro Arg Gly Glu Ser Ala Asp Gly Asp Ser Arg His Glu Val Leu
        515                 520                 525

Cys Ala Arg Leu Ala Pro Leu Asp Pro Ala Glu Arg Arg Ala Gln Leu
    530                 535                 540

Leu Thr Val Val Arg Glu Ser Ala Ala Ala Ala Leu Asp Gly Asp Asp
545                 550                 555                 560

Gln Gly Ser Ile Asp Gly Arg Arg Thr Phe Arg Asp Leu Gly Ile Thr
                565                 570                 575

Ser Leu Ala Ala Val Gly Ile Arg Asp Arg Leu His Ser Ala Thr Gly
            580                 585                 590

Leu Arg Leu Ser Pro Thr Val Val Phe Asp His Pro Thr Pro Asp Ala
        595                 600                 605

Leu Ala Ala His Leu Asp Thr Glu Leu Phe Gly Thr Gly Ala Asp Ala
    610                 615                 620

Glu Pro Ala Pro Ala Ala Gly Gly Arg Ala Val Pro His Asp Glu Pro
625                 630                 635                 640

Met Ala Ile Val Gly Met Ala Cys Arg Tyr Pro Gly Gly Val Gly Ala
                645                 650                 655

Pro Ala Asp Leu Trp Arg Thr Val Leu Ala Gly Val Asp Ala Val Gly
            660                 665                 670

Pro Leu Pro Ala Asp Arg Gly Trp Asn Ile Ala Asp Gly Tyr Asp Pro
        675                 680                 685

Glu Leu Ala Gly Pro Gly Arg Phe Ser Gln Arg Glu Gly Gly Phe Leu
    690                 695                 700
```

-continued

```
His Asp Ala Ala Glu Phe Asp Ala Glu Phe Phe Gly Ile Ser Pro Arg
705                 710                 715                 720

Glu Ala Leu Ala Met Asp Pro Gln Gln Arg Leu Ala Leu Glu Ser Ala
                725                 730                 735

Trp Glu Ala Ile Glu Asp Ala Gly Leu Asp Ala His Ser Leu Arg Gly
            740                 745                 750

Ser Arg Thr Gly Val Phe Leu Gly Leu Ile Thr Gln Asp Tyr Gly Pro
        755                 760                 765

Arg Ala Gly Glu Pro Thr Thr Arg Ala Gly Ala Val Glu Gly His Leu
    770                 775                 780

Phe Leu Gly Ser Thr Gly Ser Val Ala Ser Gly Arg Leu Ser Tyr Thr
785                 790                 795                 800

Leu Gly Leu Glu Gly Pro Ser Leu Thr Ile Asp Thr Ala Cys Ser Ser
                805                 810                 815

Ser Leu Val Ala Leu His Glu Ala Cys Gln Ala Leu Arg Thr Gly Asp
            820                 825                 830

Cys Asp Met Ala Leu Thr Gly Gly Val Thr Val Met Pro Ser Thr Gly
        835                 840                 845

Met Leu Val Glu Phe Ser Arg Gln Arg Gly Leu Ser Pro Asp Gly Arg
    850                 855                 860

Cys Lys Ala Phe Ser Ala Ser Ala Asp Gly Phe Gly Leu Ala Glu Gly
865                 870                 875                 880

Val Gly Met Leu Val Val Glu Arg Leu Ser Asp Ala Arg Arg Leu Gly
                885                 890                 895

His Arg Val Leu Ala Val Val Arg Gly Ser Ala Val Asn Gln Asp Gly
            900                 905                 910

Ala Ser Asn Gly Leu Ser Ala Pro Ser Gly Pro Ala Gln Gln Arg Val
        915                 920                 925

Ile Arg Gln Ala Leu Val Asn Ala Gly Val Gln Ala Ser Gln Val Asp
    930                 935                 940

Val Val Glu Ala His Gly Thr Gly Thr Lys Leu Gly Asp Pro Ile Glu
945                 950                 955                 960

Ala Gln Ala Leu Gln Ala Thr Tyr Gly Gln Gly Arg Pro Ala Glu Arg
                965                 970                 975

Pro Leu Trp Leu Gly Ser Leu Lys Ser Asn Ile Gly His Ala Gln Ala
            980                 985                 990

Ala Ala Gly Val Gly Gly Val Ile  Lys Met Val Met Ala  Leu Arg Glu
        995                 1000                1005

Gly Val  Leu Pro Pro Thr Leu  His Ala Asp Glu Pro  Ser Pro His
    1010                1015                1020

Ile Asp  Trp Ser Ala Gly Gln  Val Arg Leu Leu Thr  Glu Glu Arg
    1025                1030                1035

Glu Trp  Pro Glu Ala Gly His  Pro Arg Arg Ala Ala  Val Ser Ser
    1040                1045                1050

Phe Gly  Val Ser Gly Thr Asn  Ala His Val Ile Leu  Glu Ala Ala
    1055                1060                1065

Pro Gly  Thr Gly Gly Ala Pro  Glu Val Ser Asp Gly  Val Leu Gly
    1070                1075                1080

Ser Ala  Pro Glu Thr Val Pro  Trp Val Leu Ser Ala  Ala Ser Pro
    1085                1090                1095

Asp Ala  Leu Arg Ala Gln Ala  Glu Arg Leu Arg Gly  His Val Ala
    1100                1105                1110

Glu Arg  Pro Gly Leu Ala Ser  Ala Asp Val Ala Phe  Ala Leu Ala
```

-continued

```
    1115                1120                1125

Thr Arg  Arg Thr Ala Leu Glu  Tyr Arg Ala Val Ala  Val Gly Ala
    1130                1135                1140

Glu Arg  Asp Glu Leu Leu Asp  Thr Leu Asp Ala Leu  Ser Ala Gly
    1145                1150                1155

Arg Pro  Ala Pro Arg Ala Val  Pro Gly Asp Ala Ala  Ala His Ser
    1160                1165                1170

Arg Arg  Pro Val Phe Val Phe  Pro Gly Gln Gly Ser  Gln Trp Ala
    1175                1180                1185

Gly Met  Ala Val Glu Leu Leu  Asp Ser Ser Pro Val  Phe Ala Asp
    1190                1195                1200

Ser Met  His Ala Cys Ser Glu  Ala Leu Asn Glu Phe  Val Asp Trp
    1205                1210                1215

Asn Leu  Leu Glu Val Leu Arg  Ser Gly Asp Glu Glu  Leu Ser Asn
    1220                1225                1230

Arg Val  Asp Val Val Gln Pro  Val Leu Trp Ala Val  Met Val Ser
    1235                1240                1245

Leu Ala  Ala Leu Trp Gln Ala  Cys Gly Val Arg Pro  Ala Ala Val
    1250                1255                1260

Val Gly  His Ser Gln Gly Glu  Ile Ala Ala Ala Val  Val Ala Gly
    1265                1270                1275

Ala Leu  Ser Leu Arg Asp Gly  Ala Arg Val Val Ala  Leu Arg Ser
    1280                1285                1290

Ala Val  Ile Ala Arg Leu Leu  Ala Gly Lys Gly Ala  Met Ala Ser
    1295                1300                1305

Val Ala  Leu Ala Ser Asp Thr  Val Arg Glu Arg Leu  Thr Pro Trp
    1310                1315                1320

Glu Gly  Arg Leu Ser Leu Ala  Ala Val Asn Gly Pro  Ser Ser Ser
    1325                1330                1335

Val Val  Cys Gly His Leu Asp  Ala Leu Asp Glu Phe  Val Ser Ala
    1340                1345                1350

Leu Glu  His Asp Gly Val Arg  Val Arg Arg Ile Ala  Val Asp Tyr
    1355                1360                1365

Ala Ser  His Ser Val Phe Val  Glu Gln Ala Glu Glu  Glu Leu Arg
    1370                1375                1380

Asn Val  Leu Thr Glu Val Ser  Pro Leu Pro Gly Gln  Val Pro Phe
    1385                1390                1395

Tyr Ser  Thr Val Thr Gly Ala  Val Leu Asp Thr Thr  Thr Leu Asp
    1400                1405                1410

Ala Gly  Tyr Trp Tyr Arg Asn  Leu Arg Gln Thr Val  Arg Phe Glu
    1415                1420                1425

Glu Thr  Val Arg Glu Leu Thr  Arg Arg Gly His Asp  Ala Phe Ile
    1430                1435                1440

Glu Val  Ser Ala His Pro Val  Leu Thr Val Gly Ile  Gln Asp Thr
    1445                1450                1455

Leu Glu  Ala Thr Gly Thr Arg  His Ala Val Cys Gly  Thr Leu Arg
    1460                1465                1470

Arg Gly  Glu Gly Gly Ala Gln  Arg Leu Leu Thr Ser  Leu Gly Glu
    1475                1480                1485

Ala Trp  Val Ala Gly Ile Ala  Val Asp Trp Ser Arg  Leu Thr Pro
    1490                1495                1500

Thr Thr  Thr Ala Val Gln Leu  Pro Thr Tyr Ala Phe  Gln His Gln
    1505                1510                1515
```

-continued

```
Arg Tyr  Trp Leu Asp Ser Thr  Thr Ala Asn Thr Gly  Asp Arg Pro
    1520                 1525                 1530

Ala Ala  Asp Arg Asp Thr Ala  Phe Trp Glu Ala Val  Gln His Thr
    1535                 1540                 1545

Asp Leu  Asp Ala Phe Ala Ala  Glu Leu Asp Ile Ala  Pro Asp Ala
    1550                 1555                 1560

Pro Leu  Gly Thr Val Leu Pro  Ala Leu Ala Asp Trp  Arg Gln Arg
    1565                 1570                 1575

Leu Arg  Thr Ala Ala Ala Val  Asp Ala Trp Arg Tyr  Arg Thr Ala
    1580                 1585                 1590

Phe Lys  Arg Leu Pro Asp Ala  Pro Gly Ala Pro Val  Leu Thr Gly
    1595                 1600                 1605

Ser Trp  Leu Ala Val Val Pro  Val Arg His Leu Asp  Asp Pro Ser
    1610                 1615                 1620

Val Thr  Thr Ser Leu Asp Ala  Val Ala Lys Ala Gly  Ala Glu Val
    1625                 1630                 1635

Val Gln  Leu Ala Ile Glu Asp  Ala Asp Ala Asp Val  Asp Arg Leu
    1640                 1645                 1650

Thr Glu  Arg Leu Arg Gly Leu  Val Ala Gly Leu Gly  Ala Ala Pro
    1655                 1660                 1665

Ala Gly  Ile Met Ser Phe Leu  Gly Leu Asp Glu Glu  Arg His Arg
    1670                 1675                 1680

Asp His  Pro Ala Met Pro Ser  Gly Leu Ala Thr Ser  Leu Ala Leu
    1685                 1690                 1695

Val Arg  Ala Leu Gly Arg Ala  Gly Ile Gly Ala Pro  Leu Trp Met
    1700                 1705                 1710

Val Thr  Arg Glu Ala Val Ala  Ala Gly Gln Asp Thr  His Pro His
    1715                 1720                 1725

Ala Pro  Leu Gly Ser Leu Ile  Trp Gly Leu Gly Gln  Val Thr Ala
    1730                 1735                 1740

Leu Glu  His Ala Asp Arg Trp  Gly Gly Leu Ile Asp  Leu Pro Gly
    1745                 1750                 1755

Val Cys  Asp Ala Arg Val Ala  Arg Met Leu Cys Ala  Gly Leu Ser
    1760                 1765                 1770

Gly Arg  Gly Ala Glu Asp Gln  Leu Ala Leu Arg Pro  Ser Gly Thr
    1775                 1780                 1785

Phe Val  Arg Arg Leu Ala His  Ile Pro Gly Glu Gln  Arg Ala Ala
    1790                 1795                 1800

Arg Arg  Ser Trp Gln Pro Arg  Gly Thr Val Ile Val  Thr Gly Gly
    1805                 1810                 1815

Thr Gly  Ala Leu Gly Ala Val  Leu Ala Arg Trp Leu  Ala Thr Glu
    1820                 1825                 1830

Asp Ala  Glu His Leu Val Leu  Thr Gly Arg Arg Gly  Ala Asp Ala
    1835                 1840                 1845

Pro Gly  Ala Glu Arg Leu Arg  Asp Glu Leu Val Ala  Thr Gly Ala
    1850                 1855                 1860

Arg Val  Thr Leu Ala Ala Cys  Asp Val Ala Asp Arg  Lys Ala Val
    1865                 1870                 1875

Ala Ala  Leu Leu Asp Glu Leu  Ala Ala Asp Gly Glu  Thr Val Arg
    1880                 1885                 1890

Ala Val  Leu His Ala Ala Gly  Val Ala Asp Leu Thr  Ser Leu Glu
    1895                 1900                 1905
```

```
Asn Thr  Gly Pro Glu Ala Phe  Ala Ala Gly Val Ala  Ala Lys Val
    1910                 1915                 1920

Asp Gly  Ala Leu His Leu Thr  Glu Leu Leu Asp His  Asp Ser Leu
    1925                 1930                 1935

Asp Ala  Phe Val Leu Phe Ser  Ser Ile Ala Gly Val  Trp Gly Ser
    1940                 1945                 1950

Gly Asp  His Gly Ala Tyr Ala  Ala Ala Asn Ala Phe  Leu Asn Ala
    1955                 1960                 1965

Leu Ala  Glu Tyr Asn Arg Ala  Arg Gly Ile Pro Thr  Thr Ser Ile
    1970                 1975                 1980

Ala Trp  Gly Val Trp Asn Ala  Phe Gly Val Glu Gly  Ala Gly Gly
    1985                 1990                 1995

Ile Ser  Glu Ala Val Asp Leu  Asp Gln Leu His Arg  Arg Gly Leu
    2000                 2005                 2010

Pro Leu  Ile Glu Pro Glu Leu  Gly Leu Thr Ala Leu  Arg Arg Ala
    2015                 2020                 2025

Leu Asp  Arg Asp Glu Thr Val  Leu Thr Val Ala Pro  Val Ala Trp
    2030                 2035                 2040

Glu Arg  Phe Phe Pro Leu Phe  Ser Ala Ala Arg Pro  Arg Pro Leu
    2045                 2050                 2055

Phe Glu  Asp Leu Pro Gln Val  Arg Ala Leu Ser Ala  Pro Val Pro
    2060                 2065                 2070

Thr Thr  Ala Gly Pro Ala Val  Glu Pro Gly Arg Arg  Gly Ser Gly
    2075                 2080                 2085

Leu Gly  Asp Leu Pro Leu Thr  Asp Arg Asp Ser Ala  Leu Leu Ala
    2090                 2095                 2100

Leu Val  Arg Gly Glu Ser Ala  Ser Val Leu Gly Tyr  Glu Arg Pro
    2105                 2110                 2115

Asp Arg  Leu Asp Pro Asp Arg  Ala Leu Arg Asp Val  Gly Phe Asp
    2120                 2125                 2130

Ser Leu  Thr Ala Met Glu Leu  Arg Asn Arg Leu Ala  Thr Ala Thr
    2135                 2140                 2145

Gly Leu  Thr Leu Pro Ala Ala  Leu Val Phe Asp His  Pro Thr Pro
    2150                 2155                 2160

Leu Ala  Ile Ala Ala Tyr Leu  Lys Ala Glu Leu Tyr  Gly Pro Asp
    2165                 2170                 2175

Pro Gly  Asp Asp Ser Ser Val  Leu Thr Glu Leu Asp  Gly Leu Ser
    2180                 2185                 2190

Gln Arg  Leu Ala Ala Ile Asp  Pro Asp Thr Asn Thr  Arg Leu Glu
    2195                 2200                 2205

Ile Thr  Leu Arg Leu Arg Ser  Leu Leu Thr Gln Trp  Ser Glu Pro
    2210                 2215                 2220

Asp Gly  Gly Arg Thr Thr Ala  Glu Thr Ala Thr Ala  Thr Ser Thr
    2225                 2230                 2235

Thr Ala  Leu Glu Ser Ala Ser  Ala Asp Glu Val Leu  Ala Phe Ile
    2240                 2245                 2250

Asp Thr  Glu Leu Gly Ile
    2255
```

<210> SEQ ID NO 11
<211> LENGTH: 7431
<212> TYPE: DNA
<213> ORGANISM: Streptomyces aureofaciens

<400> SEQUENCE: 11

```
atgggcagca gccaccacca ccaccaccac agcagcggcc tggtcccgcg tggttcccac     60
atggcaggtc caccgccgtt cccgcgtcgt cgtggcccga gcggccgtcg tcgttgcggc    120
ggtcgtgcta ccccgggtag cgtccgtgac cgtacgggtc gtcgtccggc agccgttccg    180
agccgtgcag tttgcgcagc ggatctgtgc gaagaaaatg acgacggctc gaagaatgtt    240
tctgaacatc gcggtagcgc aggtggttcc gtgctgtttc cacgtaccgg caccgtcctg    300
ccgtgggtac tgaccggtcc tggcgcagcg gcggttcgcg cacgctccga agcactgcgc    360
acgcacctgc gtgcgagcac cgagtggtcc cctgcgggcg tcggtcaggc gctgctggcc    420
ggtacgggtg cgggtgccga tacccaccgt gccgttgttc tggcaggcga ccgtgcccag    480
accctgaacg cattggcagc gctgagcgca ggcgcagacc acccggcagt tttcaccagc    540
actcgtgcgg atgcaagccc ggctggcccg gtgtttgtgt tcccgggtca aggctcgcag    600
tggaccggta tggctcgtga actgctggac tccgcaccgg ttttcgcgcg taagctgcac    660
gactgtgcag acgcgtttgc cccgtacctg ggccacagcc tgctggatag cgtcaccggt    720
gcagcaggtg gtccagagcc tgttggcgcg gacgtcgtcc aaccggcgct gttcgccgtt    780
atggttgcgc tgactgatct gtggaacgcg gctggcgttg caccgggtgc actgctgggt    840
cactccctgg gtgaactggc agccgcgcat gtcgcgggtg ttctgtccct ggacgattct    900
gctcgcgtcg tggcgcgttg gagccaagcg caggctacgt tggcgggtcg tggtgacatg    960
gtcagcgttc tgttgcctgc ggatgaattg gcggacctgc tggaccgccg ttggccgggt   1020
cgcttggttg tggcggttga aaacggtcca ggtagcgcgg tcgcgagcgg tgacctggac   1080
gctgcggcgg aactggtcgc acacctgacc gccgaaggta tccacgcgcg tcgcgttgac   1140
gtgggcctgg cggctcacag cccgcacatt gacgcgatcc tgccacgtat tcgcgcggac   1200
atcgcgccga ttcgtgcgca tacgccgagc atcccggttt attcggcgct gcatggtggt   1260
gcactggatg gcacgccaat ggacgcggcg tactggtgtc gtaatctgcg ctccactgta   1320
cgtttcgcgg acgcgacccg tgcagccctg gaggcaggcc ataccacgtt tgtggaggta   1380
agcccacatc cggtcctgac tacggcgatg gaggtgagcg caacccgtgc cgcgcacgca   1440
gcaactgtcc tgggtacgct gcgccgtggt gagggtggtc cgagccgctt cctggcgagc   1500
ctggccgaac tgcatgtcag cggtggtgat gccgatctgc gtacggttct gccggctagc   1560
caggcggctg gcttgccgga aaccgttctg acggcgggtc cgcgtggcga gagcgcggat   1620
ggcgactctc gtcatgaggt tctgtgcgca cgcctggcac cgctggaccc agcggagcgt   1680
cgtgcccagc tgctgactgt tgttcgtgaa agcgcagctg ccgcgctgga cggcgacgat   1740
caaggtagca ttgacggtcg tcgcacgttc cgtgacctgg gtatcacgtc gctggcagcg   1800
gtgggcatcc gtgatcgcct gcattccgca accggtctgc gtctgtctcc gaccgttgtg   1860
tttgatcatc cgaccccgga cgcactggcg gcacacttgg acaccgaact gttcggcacg   1920
ggcgcagatg ccgagccggc accagctgcg ggtggtcgtg cggtgccgca tgacgaacca   1980
attgcgatcg tgggtatggc gtgccgttac cctggcggcg ttggtgcacc ggccgacctg   2040
tggcgtaccg ttctggccgg tgtcgacgca gttggtccgc tgccggctga tcgtggctgg   2100
aatattgcgg acggttacga tccggagctg gcgggtcctg gtcgttttag ccagcgtgag   2160
ggcggctttc tgcacgacgc agctgaattt gatgcggagt tctttggtat tagcccgcgt   2220
gaggcattgg cgatggaccc gcagcaacgt ttggctctgg aaagcgcctg ggaagcgatt   2280
gaggatgcgg gtctggacgc ccatagcctg cgtggcagcc gtactggcgt tttctgggc    2340
```

```
ttgattaccc aggattatgg tcctcgtgcg ggtgagccga ccacgcgtgc aggtgcggtg   2400
gagggtcacc tgttcctggg tagcactggc agcgtcgcaa gcggtcgtct gagctatacc   2460
ttgggtctgg aaggtccgtc tttgacgatt gatacggcat gttcgagcag cctggtggca   2520
ctgcacgaag catgtcaagc gctgcgtacc ggtgattgcg acatggctct gactggtggt   2580
gtgacggtca tgccgagcac cggcatgttg gtcgagttca gccgtcagcg tggtctgtcg   2640
cctgacggcc gttgtaaagc cttttctgca tctgccgacg gttttggtct ggcggaaggt   2700
gtcggtatgc tggtggttga gcgtctgagc gatgcgcgtc gtctgggcca tcgtgtgctg   2760
gcggtggtgc gcggttctgc ggttaaccaa gatggcgcga gcaatggcct gtcggcgcct   2820
agcggcccag cacaacagcg cgttattcgc caggcgctgg tcaacgctgg cgtccaagca   2880
tcccaagtgg acgttgtcga agcacatggc accggtacga aactgggcga tccgattgag   2940
gctcaagccc tgcaagcgac ctatggccag ggccgtccgg ctgagcgccc gttgtggttg   3000
ggttctctga agtccaatat cggccacgcg caagcggcag cgggtgtggg cggtgttatc   3060
aaaatggtca tggcgttgcg tgaaggcgtc ctgccaccga ccctgcacgc agacgagccg   3120
agcccgcata ttgactggtc ggcgggtcag gttcgtctgc tgaccgagga acgcgagtgg   3180
ccggaggcag gtcaccctcg ccgtgcggca gtttcgagct tcggtgttag cggtaccaac   3240
gcacatgtga ttctggaagc tgcaccgggt acgggtggtg cgccagaagt ttcggacggt   3300
gtcctgggta gcgcgcctga aacggtcccg tgggtgctga gcgctgcaag ccctgacgca   3360
ttgcgtgcac aagcagagcg tctgcgcggt catgtggcgg agcgtccggg tctggcttcc   3420
gccgatgtcg cgtttgcgct ggcgacccgt cgtaccgcgc tggaatatcg cgcggtggcg   3480
gttggtgcgg agcgcgacga gctgctggat accttggacg cgctgagcgc cggtcgtccg   3540
gcaccgcgtg ctgtaccggg tgacgcggct gcgcatagcc gtcgtccggt tttcgtcttt   3600
ccgggtcagg gtagccagtg ggcaggtatg gcggttgaac tgctggacag cagcccggtt   3660
tttgcggaca gcatgcacgc atgttccgag gccctgaatg aatttgttga ctggaacctg   3720
ctggaagttc tgcgtagcgg tgacgaagag ctgtctaacc gtgttgatgt cgtccaaccg   3780
gtgctgtggg cagttatggt gagcctggca gctctgtggc aagcgtgtgg cgtccgtcct   3840
gcggcggttg tgggtcacag ccaaggtgag attgcagctg ccgttgtcgc aggtgcactg   3900
agcctgcgtg atggtgcccg cgttgttgca ttgcgtagcg cagtgatcgc gcgtctgctg   3960
gcaggtaagg gtgcgatggc gagcgtggct ctggcgtctg acaccgttcg tgagcgcctg   4020
accccgtggg aaggtcgtct gtctctggca gcggtcaatg gtccgagcag cagcgttgtt   4080
tgcggccatc tggatgcact ggacgagttc gttagcgcgt tggagcacga tggcgtgcgt   4140
gtgcgtcgca tcgcggttga ctacgcaagc catagcgtgt tcgtggagca ggcagaagaa   4200
gagctgcgta atgtcctgac cgaggtgagc cctttgccgg gtcaagtccc tttctacagc   4260
accgtgaccg gtgcggttct ggataccacg actctggacg ccggctactg gtatcgtaac   4320
ttgcgtcaga cggttcgttt cgaagaaacc gtgcgtgagc tgacgcgccg tggccacgac   4380
gcgttcatcg aggtgtcggc tcatccggtt ctgaccgtcg gcattcagga taccttggaa   4440
gccaccggca cccgccatgc agtctgcggt acgctgcgtc gtggtgaggg cggtgcgcag   4500
cgtttgctga ccagcctggg tgaagcgtgg gttgccggca ttgcggtgga ctggagccgc   4560
ttgacgccga cgacgaccgc tgtccaactg ccgacctacg catttcagca tcagcgttac   4620
tggctggata gcaccactgc aaacactggt gaccgtccgg cagcggaccg tgacaccgca   4680
ttttgggaag ctgtgcagca caccgacctg gacgccttcg ctgcagaatt ggacattgcc   4740
```

ccggatgcgc cgttgggcac cgtcttgccg gctctggctg actggcgtca acgcctgcgt 4800
acggcagcgg ctgttgacgc atggcgttac cgcaccgcct ttaaacgtct gccagatgcg 4860
ccaggtgcac cagtcctgac gggcagctgg ctggccgtag ttccggtgcg tcacctggat 4920
gatccgagcg ttaccactag cctggatgca gttgctaaag cgggtgcgga agtcgttcag 4980
ttggcaatcg aagatgcgga cgcggacgtt gatcgtctga ctgagcgctt gcgtggcctg 5040
gttgccggtc tgggtgccgc gccggcgggc attatgagct tcctgggtct ggatgaagag 5100
cgtcatcgtg accacccggc gatgccgagc ggtctggcca ccagcttggc gctggtccgc 5160
gccttgggtc gtgcgggcat cggtgcaccg ctgtggatgg ttacgcgtga ggcagtggca 5220
gcgggtcaag acacgcaccc gcatgcgcct ctgggtagcc tgatctgggg tctgggccaa 5280
gtgacggctc tggagcacgc agatcgctgg ggtggtctga tcgatctgcc gggtgtgtgt 5340
gatgcgcgcg ttgcccgcat gctgtgcgcg ggtctgagcg gccgtggtgc cgaagatcag 5400
ctggccctgc gtccgagcgg cactttcgtc cgccgtctgg cgcatatccc tggcgagcaa 5460
cgtgcagcac gtcgtagctg gcaaccacgt ggtacggtga ttgtcaccgg tggtacgggt 5520
gcgctgggtg cagtcctggc ccgctggttg gctaccgagg acgcggagca cctggtgctg 5580
accggccgtc gtggcgcgga cgcccctggc gcggagcgtt tgcgtgacga gctggtcgct 5640
acgggcgctc gtgtcacgct ggcggcgtgc gacgtggcag atcgcaaagc cgtcgccgca 5700
ttgctggacg aactggctgc ggacggcgag actgttcgcg cagttctgca cgctgcgggt 5760
gtcgccgatc tgacgtcgct ggagaatacc ggtccagaag cgttcgcggc aggcgtggcc 5820
gcgaaggtcg atggtgcact gcacctgacc gaactgttgg atcacgattc gctggatgcg 5880
tttgtgttgt tcagcagcat tgcgggtgtt tggggttccg gcgaccacgg cgcgtatgcg 5940
gctgcgaacg catttctgaa tgcgttggca gagtacaatc gtgcacgcgg tatcccgacc 6000
acgagcatcg catggggcgt ttggaacgcg tttggcgtcg agggtgcagg cggtatcagc 6060
gaggcggttg atttggacca gctgcatcgt cgcggcctgc cgctgattga accagagctg 6120
ggtctgactg cactgcgtcg cgctctagac cgtgacgaaa cggtgctgac ggttgctccg 6180
gttgcctggg agcgcttctt tccgctgttc tccgctgcac gtccgcgtcc gttgtttgag 6240
gacttgccgc aagtgcgtgc cctgagcgca cctgtcccga cgacggcggg tccggccgtg 6300
gaaccaggtc gccgtggtag cggcctgggc gatttgcctc tgacggatcg cgatagcgcg 6360
ctgctggcct tggtccgcgg tgagagcgca tccgtgctgg gttacgagcg tccagatcgc 6420
ctggacccgg accgtgcgct gcgtgatgtg ggtttcgata gcctgacggc gatggaactg 6480
cgtaaccgtc tggctaccgc gaccggcctg acgctgcctg cggccctggt gtttgatcac 6540
ccgaccccac tggcgatcgc ggcgtatctg aaagccgagc tgacgagcca gctggactcc 6600
ggtacgcctg cacgtgaagc tagctctgca ctgcgtgacg gctaccgcca agcgggtgtg 6660
agcggccgtg ttcgtagcta cctggatctg ttggcaggtc tgtcggattt ccgcgaacat 6720
tttgatggta gcgatggttt tagcctggat ctggttgata tggcagatgg tccgggtgag 6780
gtgaccgtta tttgctgcgc gggtacggct gcgatctctg gtccgcatga gttcacccgt 6840
ctggcaggtg ccctgcgcgg cattgcacct gttcgtgcgg tgccgcagcc gggttacgaa 6900
gaaggcgaac cgctgccttc tagcatggcg gctgttgcag ctgtgcaggc tgatgctgtc 6960
attcgtacgc aaggcgataa gccgttcgtg gttgcgggtc actcggcagg cgcgctgatg 7020
gcgtacgcgc tggcgaccga actgctggat cgtggtcacc cgcctcgcgg tgttgtcctg 7080

-continued attgatgtgt acccgcctgg tcatcaggac gcgatgaacg cgtggctgga ggaactgacg 7140
gcaacgttgt tcgaccgtga aactgttcgt atggacgaca cccgtctgac cgcgttgggt 7200
gcttacgacc gcctgacggg tcaatggcgt cctcgcgaaa ccggtttgcc gaccctgttg 7260
gttagcgcgg gtgaaccaat gggcccgtgg ccggacgata gctggaaacc gacctggcct 7320
ttcgagcacg acaccgttgc ggtcccgggt gatcatttca cgatggttca agaacatgct 7380
gatgcgattg cccgtcacat tgacgcctgg ctgggtggcg gcaacagctg a 7431

<210> SEQ ID NO 12
<211> LENGTH: 8
<212> TYPE: PRT
<213> ORGANISM: Streptomyces aureofaciens

<400> SEQUENCE: 12

Val Phe Val Phe Pro Gly Gln Gly
1 5

<210> SEQ ID NO 13
<211> LENGTH: 7
<212> TYPE: PRT
<213> ORGANISM: Streptomyces aureofaciens

<400> SEQUENCE: 13

Ala Tyr Leu Lys Ala Glu Leu
1 5